(12) United States Patent
Yodfat et al.

(10) Patent No.: US 8,615,281 B2
(45) Date of Patent: Dec. 24, 2013

(54) HYPODERMIC OPTICAL MONITORING OF BODILY ANALYTE

(75) Inventors: Ofer Yodfat, Maccabim-Reut (IL); Iddo M. Gescheit, Tel Aviv (IL); Illai Gescheit, Tel Aviv (IL); Ruthy Kaidar, St. Haifa (IL)

(73) Assignee: Medingo Ltd., Yoqneam Illit (IL)

( * ) Notice: Subject to any disclaimer, the term of this patent is extended or adjusted under 35 U.S.C. 154(b) by 667 days.

(21) Appl. No.: 12/744,260

(22) PCT Filed: Nov. 20, 2008

(86) PCT No.: PCT/IL2008/001520
§ 371 (c)(1),
(2), (4) Date: May 21, 2010

(87) PCT Pub. No.: WO2009/066287
PCT Pub. Date: May 28, 2009

(65) Prior Publication Data
US 2010/0249558 A1    Sep. 30, 2010

Related U.S. Application Data

(60) Provisional application No. 61/004,039, filed on Nov. 21, 2007.

(51) Int. Cl.
*A61B 5/1455* (2006.01)

(52) U.S. Cl.
USPC ............ 600/342; 600/310; 600/322; 600/340

(58) Field of Classification Search
USPC ......... 600/310, 316, 322, 323, 326, 327, 329, 600/332, 338, 339, 340, 341, 342, 344, 473, 600/476
See application file for complete search history.

(56) References Cited

U.S. PATENT DOCUMENTS

| | | | |
|---|---|---|---|
| 5,605,152 A | 2/1997 | Slate et al. | |
| 5,820,622 A | 10/1998 | Gross et al. | |
| 6,049,727 A | 4/2000 | Crothall | |
| 6,091,976 A | 7/2000 | Pfeiffer et al. | |
| 6,122,536 A | 9/2000 | Sun et al. | |
| 6,298,253 B1 * | 10/2001 | Buschmann | 600/338 |

(Continued)

FOREIGN PATENT DOCUMENTS

WO  WO-2008029403 A1  3/2008
WO  WO-2008122983 A1  10/2008
(Continued)

OTHER PUBLICATIONS

Arnold et al., "Noninvasive Glucose Sensing", *Anal. Chem.*, 77:5429-5439 (2005).

(Continued)

*Primary Examiner* — Eric Winakur
*Assistant Examiner* — Chu Chuan Liu
(74) *Attorney, Agent, or Firm* — Mintz Levin Cohn Ferris Glovsky and Popeo, P.C.

(57) ABSTRACT

Disclosed is a skin adherable device for monitoring analytes in interstitial fluid. The device includes an electromagnetic radiation emitting source and a transmitter for transmitting the electromagnetic radiation between the electromagnetic radiation emitting source and the interstitial fluid. The device further includes a detector, operating electronics and a power supply. The device may include a reusable part and a disposable part.

23 Claims, 58 Drawing Sheets

(56) References Cited

U.S. PATENT DOCUMENTS

| | | | |
|---|---|---|---|
| 6,391,643 | B1 | 5/2002 | Chen et al. |
| 6,584,335 | B1* | 6/2003 | Haar et al. ............. 600/322 |
| 6,862,465 | B2 | 3/2005 | Shults et al. |
| 6,881,551 | B2 | 4/2005 | Heller et al. |
| 6,892,085 | B2 | 5/2005 | McIvor et al. |
| 6,904,301 | B2* | 6/2005 | Raskas ................. 600/310 |
| 6,928,311 | B1 | 8/2005 | Pawluczyk et al. |
| 2003/0033102 | A1 | 2/2003 | Dietiker |
| 2004/0132171 | A1 | 7/2004 | Rule et al. |
| 2004/0260162 | A1* | 12/2004 | Rohleder et al. ........ 600/342 |
| 2005/0070773 | A1 | 3/2005 | Chin et al. |
| 2005/0113658 | A1* | 5/2005 | Jacobson et al. ........ 600/342 |
| 2006/0025663 | A1 | 2/2006 | Talbot et al. |
| 2006/0036145 | A1 | 2/2006 | Brister et al. |
| 2006/0083688 | A1 | 4/2006 | Singaram et al. |
| 2007/0004974 | A1 | 1/2007 | Nagar et al. |
| 2007/0106218 | A1 | 5/2007 | Yodfat et al. |
| 2007/0191702 | A1 | 8/2007 | Yodfat et al. |
| 2008/0281290 | A1 | 11/2008 | Yodfat et al. |
| 2008/0319414 | A1 | 12/2008 | Yodfat et al. |

FOREIGN PATENT DOCUMENTS

| | | | |
|---|---|---|---|
| WO | WO-2008139458 | A2 | 11/2008 |
| WO | WO-2008139460 | A2 | 11/2008 |
| WO | WO-2009004627 | A2 | 1/2009 |
| WO | WO-2009016636 | A2 | 2/2009 |
| WO | WO-2009016637 | A2 | 2/2009 |
| WO | WO-2009056981 | A2 | 5/2009 |
| WO | WO-2009125398 | A2 | 10/2009 |

OTHER PUBLICATIONS

Cote et al., "Glucose Diagnostics", in *Biomedical Photonics Handbook,*, Tuan Vo-Dinh, Ed., CRC Press, Boca Raton, Ch. 18, pp. 1-19 (2003).

Bolinder et al., "Microdialysis measurement of the absolute glucose concentration in subcutaneous adipose tissue allowing glucose monitoring in diabetic patients", *Diabetologia*, 35:1177-1180 (1992).

DCCT Trial Research Group, "The Effect of Intensive Treatment of Diabetes on the Development and Progression of Long-Term Complications in Insulin-Dependent Diabetes Mellitus", *N. E. J. Med.*, 329:977-986 (1993).

International Search Report for PCT Application No. PCT/IL2008/001520, mailed Jun. 4, 2009.

Jeon et al., "Comparison between transmittance and reflectance measurements in glucose determination using near infrared spectroscopy", Journal of Biomedical Optics 11(1): 014022-1-7 (2006).

Khalil, "Spectroscopic and Clinical Aspects of Noninvasive Glucose Measurements", Clinical Chemistry 45(2): 165-177, 1999.

Khalil, O. S., "Non-Invasive Glucose Measurement Technologies: An Update from 1999 to the Dawn of the New Millennium", *Diabetes Tech. Therapeutics*, 6(5):660-697 (2004).

Maran et al., "Continuous Subcutaneous Glucose Monitoring in Diabetic Patients", *Diabetes Care*, 25(2):347-352 (2002).

Mastrototaro, J. J., "The MiniMed Continuous Glucose Monitoring System", *Diabetes Tech. Therapeutics*, 2(Suppl. 1):13-18 (2000).

McCartney et al., "Near-infrared fluorescence lifetime assay for serum glucose based on allophycocyanin-labeled concanavalin A", *Anal. Biochem.*, 292:216-221 (2001).

McNichols et al., "Optical glucose sensing in biological fluids: an overview", *J. Biomed. Optics*, 5(1):5-16 (2000).

Nathan et al., "Intensive Diabetes Treatment and Cardiovascular Disease in Patients with Type 1 Diabetes", *N. E. J. Med.*, 353(25):2643-2653 (2005).

Rolinski et al., "A time resolved near-infrared fluorescence assay for glucose: opportunities for trans-dermal sensing", *J. Photochem. Photobiol. B.*, 54:26-34 (2000).

Suri et al., "Continuous Glucose Sensing with a Fluorescent Thin-Film Hydrogel", Angewandte Chemie International Edition, 42: 5857-59 (2003.

Tamada et al., "Noninvasive Glucose Monitoring Comprehensive Clinical Results", *J. Am. Med. Assoc.*, 282(19):1839-1844 (1999).

Thoniyot et al., "Continuous Glucose Sensing with Fluorescent Thin-Film Hydrogels. 2. Fiber Optic Sensor Fabrication and in Vitro Testing", Diabetes Technology & Therapeutics, 8(3); 279-287 (2006).

UKPDS Group Trial, "Tight blood pressure control and risk of macrovascular and microvascular complications in type 2 diabetes: UKPDS 38", *BMJ*, 317:703-713 (1998).

UKPDS Trial, "Intensive blood-glucose control with sulphonylureas or insulin compared with conventional treatment and risk of complications in patients with type 2 diabetes (UKPDS 33)", Lancet, 352:837-853 (1998).

Wentholt et al., "Comparison of a Needle-Type and a Microdialysis Continuous Glucose Monitor in Type 1 Diabetic Patients", *Diabetes Care*, 28(12):2871-2876 (2005).

Written Opinion of the International Searching Authority for PCT Application No. PCT/IL2008/001520, mailed Jun. 4, 2009.

* cited by examiner

HYPODERMIC OPTICAL MONITORING OF BODILY ANALYTE

CROSS-REFERENCE TO RELATED APPLICATIONS

The present application is a 35 U.S.C. §371 national stage entry of PCT/IL2008/001520, which has an international filing date of 20 Nov. 2008, which claims priority to U.S. Provisional Patent Application No. 61/004,039, entitled "Hypodermic Optical Monitoring of Bodily Analyte," filed on Nov. 21, 2007, the disclosures of which are incorporated herein by reference in their entireties.

FIELD

Methods and devices for continuous monitoring of bodily analyte and continuous delivery of therapeutic fluid to the body are described herein. More particularly, optics-based devices and a methods for continuously monitor hypodermic glucose levels are described herein. Such embodiments can be coupled with an insulin delivery means and can be integrated into a closed loop or semi closed loop system.

DEFINITIONS

Banana-shaped, photon trajectory: a backscattering geometry which is a function of the source-detector separation and tissue's optical characteristics, i.e. the absorption coefficient ($\mu_a$) and the reduced scattering coefficient ($\mu_s'$).

BACKGROUND

Diabetes and Glycemic Control

Diabetes mellitus is a disease of major global importance, increasing in frequency at almost epidemic rates, such that the worldwide prevalence in 2006 was 170 million people and predicted to at least double over the next 10 to 15 years. Diabetes is characterized by a chronically raised concentration of glucose in the blood (hyperglycemia), due to a relative or absolute lack of the pancreatic hormone, insulin. Within the healthy pancreas, beta cells located in the Islets of Langerhans continuously produce and secrete insulin according to the glucose levels, maintaining near-constant glucose levels in the body.

Much of the burden of the disease to the patient and to health care resources is due to long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). There is now good evidence that morbidity and mortality of diabetic patients is related to the duration and severity of hyperglycemia. (DCCT Trial, N Engl J Med 1993, 329: 977-986; UKPDS Trial, Lancet 1998; 352: 837-853; BMJ 1998; 317, (7160): 703-13; EDIC Trial, N Engl J Med 2005, 353, (25): 2643-53).

In theory, returning glucose levels to normal by hormone replacement therapy using insulin injections and/or other treatments should prevent complications, but, frustratingly, near-normal glucose concentrations are very difficult to achieve and maintain in many patients, particularly those with type I diabetes. In these patients, glucose concentration can swing between very high (hyperglycemia) and very low (hypoglycemia) levels in an unpredictable manner. Thus, tight glycemic control is required. This control can be achieved by substituting the two functions of the normal pancreas—glucose monitoring and insulin delivery—for maintaining tight glycemic control. Furthermore, a closed loop or semi closed loop system provided with a feedback mechanism connecting between both functions (often referred to as an "artificial pancreas") could theoretically maintain near-normal glucose levels.

Glucose Monitoring

Most diabetic patients currently measure their own glucose level periodically, i.e., several times during the day by obtaining finger-prick capillary samples and applying the blood to a reagent strip for analysis in a portable meter. Unfortunately, the discomfort involved leads to poor patient compliance. Testing cannot be performed while sleeping and while the subject is occupied. In addition, the results do not give information regarding the trends in glucose levels, but rather provide only discrete readings, taken at large time intervals from one another. Therefore, continuous glucose monitoring is advantageous, providing short-interval, essentially continuous glucose readings by performing discrete measurements, at a very high rate.

Glucose Monitoring Technologies

Continuous glucose monitoring can be performed by various methods and technologies, where most methods apply either non-invasive or minimally-invasive means.

Non-Invasive Continuous Glucose Monitoring

Non-invasive continuous glucose monitoring includes the sensing of glucose in blood, interstitial fluid (ISF) or other physiological fluids, primarily using optical means.

Continuous glucose monitoring based on optical methods employs various sensing methodologies for measuring glucose concentration levels. Optical sensing methods are quite prevalent among glucose sensors and include NIR, IR, Raman, Fluourescence, Polarimetry, and Photoacoustic (PA) technology.

In Near-Infrared (NIR) spectroscopy, a selected band of NIR light is transmitted through the sample, and the analyte concentration is obtained by the analysis of the resultant spectral information. The NIR absorbance bands tend to be broad and overlap, and are highly influenced by temperature, pH, and other physical factors. Nevertheless, the NIR spectrum allows for large optical path lengths to be used due to relatively easy passage through water (the light absorbance is directly proportional to the path length according to the Beer-Lambert law). U.S. Pat. No. 6,928,311 to Pawluczyk et al., assigned to NIR Diagnostics, Inc., describes a non-invasive monitor that uses NIR light. A beam of light in the NIR range is focused on the person's finger for about 30 seconds. By applying mathematical algorithms on the emerging light signal, the concentration of various blood analytes including glucose are determined and displayed to the user.

The NIR spectrum spans a wide range from 700 to 2500 nm. Absorption features throughout this spectral range primarily correspond to overtones and combinations of molecular vibrations. The absorption properties of water play a critical role in the regions of the NIR spectrum available for noninvasive measurements. Strong water absorption bands centered at approximately 1333, 1923, and 2778 nm (7500, 5200, and 3600 $cm^{-1}$) create three transmission windows through aqueous solutions and living tissue. These spectral windows are termed the short-wavelength region (700-1370 nm, 286-7300 $cm^{-1}$), the first overtone region (1538-1818 nm, 6500-5500 $cm^{-1}$), and the combination region (2000-2500nm, 5000-4000 $cm^{-1}$). Absorption features in the combination region correspond to first-order combination transitions associated with bending and stretching vibrations of C—H, N—H, and O—H functional groups. The first overtone region corresponds to the first-order overtone of C—H stretching vibrations, and the short-wavelength region includes numerous higher order combination and overtone transitions. For combination spectra, molar absorptivities are larger and bands are narrower compared to first overtone spectral features. NIR absorption features become significantly weaker and broader as the order increases, thereby greatly reducing the analytical utility of the short-wavelength region in terms of molecular vibrational information. (Anal Chem 2005 (77), pp. 5429-5439).

A relative dip in the water absorbance spectrum opens a unique window in the 2000-2500 nm wavelength region, saddled between two large water absorbance peaks. This window allows pathlengths or penetration depths on the order of millimeters and contains specific glucose peaks at 2130, 2270 and 2340 nm. This region offers the most promising results for quantifiable glucose measurements using NIR spectroscopy (Biomed Photonics Handbook, 2003, p. 18-13).

The different spectral regions permit for several sample volumes and optical path lengths: larger samples are possible for spectra collected at shorter wavelengths and longer wavelengths are restricted to smaller samples. Optimal sample thickness for the combination, first overtone, and short wavelength range are 1, 5, and 10 mm respectively. However, when the collected spectra encompass multiple spectral regions, it is not possible to match the sample thickness with each spectral region (Anal. Chem. 2005, 77, 5429-5439). Comparison between transmittance and reflectance measurements in glucose using near infrared spectroscopy shows that transmittance is preferred for glucose monitoring (Journal of Biomedical Optics 11 (1), pp. 014022-1-7, January/February 2006). FIG. 1a shows the optical absorption spectra of glucose in the NIR region for aqueous glucose after water subtraction (Journal of Biomedical Optics 5 (1), 5-16 Jan. 2000)

In mid-Infrared (mid-IR) spectroscopy, the wavelengths of glucose absorbance in the mid-IR spectrum range (2500-10000 nm) are used for the analysis of glucose concentration. Although the absorption bands tend to be sharp and specific, there is strong background absorption by water that severely limits the optical path length that may be used. FIG. 1b shows the optical absorption spectra of glucose in the mid-IR region for aqueous glucose after water subtraction (Journal of Biomedical Optics 5 (1), 5-16 Jan. 2000).

In Raman spectroscopy, Raman spectra are observed when incident light is inelastically scattered producing Stokes and anti-Stokes shifts, where the latter is the more prevalent. Raman spectra are less influenced by water compared to NIR/IR and the peaks are spectrally narrow. In addition, Raman spectroscopy requires minimal sample preparation. However, the signal is weak and therefore requires a highly sensitive detection system (e.g., CCD array).

It is possible to detect glucose by monitoring the 3448 nm (2900 $cm^{-1}$) C—H stretch band or the C—O and C—C stretch Raman bands at 8333-11111 nm (900-1200 $cm^{-1}$), which represents a fingerprint for glucose (Clinical Chemistry 45:2 165-177, 1999). FIG. 1c shows the Raman spectrum for aqueous glucose, after subtraction of the water background (Journal of Biomedical Optics 5 (1), 5-16 Jan. 2000).

In fluorescence energy transfer (FRET)-based assay for glucose measurement, concanavalin A is labeled with the highly NIR-fluorescent protein allophycocyanin as donor and dextran labeled with malachite green as the acceptor (see, J Photochem Photobiol 2000; 54: 26-34. and Anal Biochem 2001; 292: 216-221). Competitive displacement of the dextran from binding to the lectin occurs when there are increasing glucose concentrations, leading to a reduction in FRET, measured as intensity or lifetime (time-correlated single-photon counting).

Polarimetry involves the optical rotation of the polarized light by the chiral centers of glucose, which is determined by the structure of the molecule, the concentration of the molecule, and the optical path length the light traverses through the sample. Each optically active substance has its own specific rotation, as defined by Biot's law. The measurement of the optical rotation requires a very sensitive polarimeter, due to the low glucose concentrations in the cell. For example, at a wavelength of 670 nm, glucose will rotate the linear polarization of a light beam approximately 0.4 millidegrees per 10 mg/dl for a 1-cm sample pathlength (Biomedical Photonics Handbook, 2003, p. 18-14). In addition, the presence of other optically active molecules makes the accurate detection of glucose concentration complicated.

Finally, PA spectroscopy involves light which is absorbed by glucose, leading to thermal expansion and to the generation of a detectable ultrasound pressure wave. In one study, solutions of different glucose concentrations were excited by NIR laser pulses at wavelengths that corresponded to NIR absorption of glucose in the 1000-1800 nm range. There was a linear relationship between PA signal and glucose concentrations in aqueous solutions (Diabetes Technology & Therapeutics, Vol. 6, November 2004, O. S. Khalil). This method is particularly sensitive to changes in temperature.

Optical glucose measurement techniques are particularly attractive for several reasons: they utilize nonionizing radiation to interrogate the sample, are reagentless, and fast. The use of optical glucose monitoring methods is especially attractive because they are nondestructive and reagentless, thereby eliminating the risk of unsafe reactions and their by-products.

Although optical approaches for glucose sensing are attractive, they are nevertheless often plagued by a lack of sensitivity and/or specificity since variations in optical measurements depend on variations of many factors in addition to glucose concentration. Isolating those changes which are due to glucose alone and using them to predict glucose concentration is a significant challenge in itself (Journal of Biomedical Optics 5 (1), 5-16 Jan. 2000). Furthermore, non-invasive optical glucose monitors, which involve sensing of glucose levels through the skin, involve very low signal-to-noise ratio, scattering and interferences by bodily fluids and by the skin itself, causing noninvasive optical sensors to lack specificity and repeatability.

Since optics-based noninvasive applications do not produce accurate and specific results, it would be desirable to provide an immediate application of the optical methods directly to the ISF or to fluids comprising endogenous components of the ISF, thus, eliminating the attenuating effects of the skin.

Invasive Continuous Glucose Monitoring

Invasive continuous glucose monitoring involves the implantation of a sensing device in the body. As detailed in U.S. Pat. Nos. 6,122,536 to Sun et al. and 6,049,727 to Crothall, assigned to Animas Corporation, an invasive spectroscopy-based glucose sensor, designed for long-term (>5 years) internal use is under development. The Animas sensor has the advantage of being able to directly read glucose in the blood. A small, ultralight C-clamp detector is surgically implanted around a 4-5 mm (0.2 inch) diameter blood vessel. The detector has two tiny probes at the tips of the C-clamp structure which puncture each side of the vessel and allow transmission of a clean infrared light signal between them. A larger device housing a laser generator plus signal analysis is located nearby within a closed compartment under the skin. The laser IR signal is transmitted to the detector around the vessel and returns the transmitted beam back to the processing unit.

Readings are available at short time intervals. Major advantages of the implantable approach are that calibration is required only once a week and that although minor surgery is required, this sensor provides direct access to blood.

Other invasive continuous glucose monitoring (CGM) systems are often based on electrochemical techniques. U.S. Pat. No. 6,862,465 to Shults et al. and U.S. Pub. No. 2006/0036145A1 to Brister et al., assigned to DexCom, Inc., describe a long term glucose oxidase (GOX)-based CGM system. The system includes a sensor, a small implantable device that continuously measures glucose levels in the subcutaneous tissue, and a small external receiver to which the sensor transmits glucose levels at specified intervals. The receiver displays the patient's current blood glucose value, as well as 1-hour, 3-hour and 9-hour trends. The receiver also sounds an alert when an inappropriately high or low glucose excursion is detected. The DexCom™ Long Term Sensor is implanted under the skin in the abdomen by a local anesthetic short procedure carried out by a physician. This sensor is designed to function for up to one year. At the end of its life, the sensor can be removed by a physician in a short procedure, and another sensor implanted.

Implanted CGMs have several disadvantages, such as the need for a surgical procedure to implant the device, possibility of failure, the potential for sensor blockage, and biocompatibility problems.

Minimally-Invasive Glucose Monitoring

Disadvantages in the performance and operation of non-invasive and fully invasive CGMs lead to the development of various minimally-invasive CGM systems. Minimally-invasive CGMs often measure glucose levels in the ISF within the subcutaneous tissue, and are based on various sensing technologies. The strong correlation between blood and ISF glucose levels, allows for accurate ISF glucose measurements (Diabetologia 1992; 35, (12): 1177-1180).

GlucoWatch® G2® Biographer is one commercially available minimally-invasive glucose monitor. GlucoWatch® is based on reverse iontophoresis as detailed in U.S. Pat. No. 6,391,643, to Chen et al., assigned to Cygnus, Inc. A small current passed between two skin-surface electrodes draws ions and (by electro-endosmosis) glucose-containing ISF to the surface and into hydrogel pads provided with a GOX biosensor (JAMA 1999; 282: 1839-1844). Readings are taken every 10 minutes with a single capillary blood calibration.

Disadvantages of the GlucoWatch® include occasional sensor values differing markedly from blood values, skin rashes and irritation in those locations which are immediately underneath the device appearing in many users, a long warm up time of 3 hours, and skips in measurements due to sweating.

Two additional commercially available minimally-invasive monitors are GOX-based CGMs, based on enzyme-immobilization.

The Guardian® RT Continuous Glucose Monitoring System, developed by Medtronic MiniMed Inc. is a GOX-based sensor, as described in U.S. Pat. No. 6,892,085 to McIvor et al. The sensor consists of a subcutaneously implanted, needle-type, amperometric enzyme electrode, coupled with a portable logger (Diab Tech Ther 2000; 2: Supp. 1, 13-18). The Guardian® RT system displays updated glucose readings every five minutes, together with hypo- and hyperglycemic alarms. The sensor is based on the long-established technology of GOX immobilized at a positively charged base electrode, with electrochemical detection of hydrogen peroxide production.

U.S. Pat. No. 6,862,465 to Shults et al. and U.S. Pub. No. 2006/0036145A1 to Brister et al., assigned to DexCom, Inc., describe a short-term GOX-based CGM system. The system includes a sensor, a small insertable or implantable device that continuously measures glucose levels in the subcutaneous tissue, and a small external receiver to which the sensor transmits glucose levels at specified intervals. The receiver displays the patient's current blood glucose value, as well as 1-hour, 3-hour and 9-hour trends. The receiver also sounds an alert when an inappropriately high or low glucose excursion is detected. The DexCom™ STS™ Continuous Glucose Monitoring System is a user insertable short-term sensor that is inserted just under the skin where it is held in place by an adhesive. Once inserted the user would wear the sensor for up to three or seven days before being replaced. After three or seven days, the user removes the sensor from the skin and discards it. A new sensor can then be used with the same receiver. The DexCom™ STS™ Continuous Glucose Monitoring System has been FDA-approved.

The Freestyle Navigator™ is another GOX-based sensor, detailed in U.S. Pat. No. 6,881,551 to Heller et al., assigned to Abbott Laboratories, formerly TheraSense, Inc. This sensor is placed just under the skin by a disposable self-insertion device. Information is communicated wirelessly between the transmitter and the receiver every minute. The receiver is designed to display glucose values, directional glucose trend arrows, and rate of change. The receiver also has high and low glucose alarms, and stores glucose data for future analysis.

Numerous disadvantages inherent to glucose monitoring are present in CGMs which employ GOX-based reactions. Most GOX-based devices rely on the use of oxygen as the physiological electron acceptor, and thus, are subject to errors due to fluctuations in the oxygen tension and the stoichiometric limitation of oxygen in vivo. The amperometric measurement of hydrogen peroxide requires application of a potential at which additional electroactive species exist, e.g. ascorbic and uric acids or acetaminophen. These and other oxidizable constituents of biological fluids can compromise the selectivity and hence the overall accuracy of the glucose concentration measurement. Hydrogen peroxide deactivates the GOX molecules, limiting the time available for application of the sensor. Miniaturizing the sensing technology within the cannula, which requires high levels of enzyme loading, while keeping high measurement sensitivity, remains a challenge.

Numerous disadvantages inherent to glucose monitoring are present in CGMs which employ GOX-based reactions. Most GOX-based devices rely on the use of oxygen as the physiological electron acceptor, and thus, are subject to errors due to fluctuations in the oxygen tension and the stoichiometric limitation of oxygen in vivo. The amperometric measurement of hydrogen peroxide requires application of a potential at which additional electroactive species exist, e.g. ascorbic and uric acids or acetaminophen. These and other oxidizable constituents of biological fluids can compromise the selectivity and hence the overall accuracy of the glucose concentration measurement. Hydrogen peroxide deactivates the GOX molecules, limiting the time available for application of the sensor. Miniaturizing the sensing technology within the cannula, which requires high levels of enzyme loading, while keeping high measurement sensitivity, remains a challenge.

Microdialysis Based Glucose Monitors

Microdialysis is an additional commercially-available minimally-invasive technology (Diab Care 2002; 25: 347-352) for glucose monitoring as detailed in U.S. Pat. No. 6,091,976 to Pfeiffer et al., assigned to Roche Diagnostics GmbH, and the marketed device, GlucoDay® S, produced A. Menarini Diagnostics. A fine, semi-permeable hollow dialysis fiber is implanted in the subcutaneous tissue and perfused with isotonic fluid. Glucose diffuses across the semi-permeable fiber and is pumped outside the body via the microdialysis mechanism for measurement by a glucose oxidase-based electrochemical sensor. Initial reports (Diab Care 2002; 25: 347-352) show good agreement between sensor and blood glucose readings, and good stability with a one-point calibration over one day. Higher accuracies were found when using the microdialysis-based sensor, compared to the needle-type sensor (Diabetes Care 2005; 28, (12): 2871-6).

Disadvantages of the microdialysis-based glucose sensors stem primarily from the constant perfusion of solution through the microdialysis probe. This operational method requires the presence of a dedicated pump and reservoir, leading to large and bulky devices, and also necessitates high-energy consumption. Furthermore, the relatively large size of the microdialysis catheter often causes a wound and subsequent local tissue reactions, following its insertion into the subcutaneous tissue. Finally, the microdialysis process generates long measurement lag times, due to the essential slow perfusion rates and long tubing.

Optics Based Glucose Monitors

U.S. Pub. No. 2007/0004974 A1 to Nagar et al. describes a device for assaying an analyte in the body, comprising a light source implanted in the body, able to illuminate a tissue region with light, at a wavelength that is absorbed by the analyte and as a result generates PA waves in the tissue region. An acoustic sensing transducer is coupled to the body, receives acoustic energy from the PA waves, and generates responsive signals. A processor receives the signals and processes them to determine a concentration of the analyte in the illuminated tissue region.

U.S. Pat. No. 5,605,152 to Slate et al. describes an improved glucose sensor adapted for in vivo implantation which includes one or more optical fiber optrodes mounted within a semi-permeable probe housing designed for differential diffusion of glucose and oxygen. An enzyme optrode comprises an optical fiber with an enzyme coating such as GOX to yield an enzymatic glucose reaction. An oxygen sensitive coating such as a fluorescent dye is provided on the enzyme optrode close to the enzymatic reaction and also on a reference optrode at a position spaced substantially from the enzymatic reaction. Optical monitoring of the fluorescent activity of the optrode coatings provides an indication of oxygen depletion as a result of the enzymatic reaction and thus indicates the glucose concentration level. The semi-permeable housing is designed to ensure that the reaction proceeds with a stoichiometric excess of oxygen.

Disadvantages of optics-based glucose monitoring techniques stem primarily from the indirect optical means applied for measuring analyte concentration levels. In addition, optics-based techniques involving an electrochemical reaction possess the disadvantages inherent to glucose monitors which employ GOX-based reactions, described hereinbefore.

SUMMARY OF THE INVENTION

Methods and devices for continuous monitoring of body analytes and delivery of fluids to the body are provided. Some embodiments relate to a monitoring device that includes an optically-based monitoring patch unit for continuous measurement of bodily analyte levels. The monitoring device may contain at least one of the following units:
1. Monitoring patch unit (hereinafter "patch unit")—includes an optical monitoring apparatus, which comprises a light-emitting source, detector, electronics, and a power supply. The patch unit can be comprised of a single part or two parts as follows:
    2. Reusable part—contains relatively expensive components including light-emitting source, detector, and electronics (including processor for analyzing light spectra)
    3. Disposable part—contains inexpensive components such as reflectors and optical fibers
    4. In the two-part configuration, the power supply can reside in the disposable part, reusable part or both Cradle unit—includes a flat sheet with an adhesive layer facing the skin, connecting means for the patch unit, an opening to provide a passageway for the probe, and anchoring means for the probe. Disconnection and reconnection of the patch unit from and to the cradle unit can be carried out at a user's discretion Cartridge unit—includes the following:
1. Probe—used as a light conductive means from the patch unit to the body and from the body to the patch unit.
2. Penetrating member—sharp retractable means for probe insertion.
3. Protector—shields the probe and penetrating member.
4. The cartridge unit can be loaded onto an automatic inserter that fires the probe through the cradle unit opening into the body. After insertion (and retraction of the penetrating member into the protector), the probe is rigidly connected to the cradle unit by the anchoring means.

Remote control unit—provides programming, data acquisition and displaying.

In some embodiments, the patch unit is provided with input and output means, e.g., a display, and/or at least one operating button enabling issuance of instructions.

According to some of the embodiments, the monitoring apparatus contains a light-emitting source, detector, and optical means for directing the light between the patch unit and the user's body.

In some embodiments, the monitoring device can be attached and detached from a user's skin upon the user's discretion.

According to some of the embodiments, the monitoring apparatus is capable of monitoring analyte concentration levels by performing discrete, high-rate measurements.

In some embodiments, the monitoring device comprises a single probe for monitoring analyte levels (e.g., glucose). The probe transmits light from the light-emitting source in the patch unit to the body and back to a detector in the patch unit.

In some embodiments, the monitoring device comprises two separate probes for monitoring analyte levels (e.g., glucose) used for transmitting light from the light-emitting source in the patch unit to the body and back to a detector in the patch unit.

In some embodiments, the two-part patch unit is provided with a monitoring apparatus. Light is conducted from the light-emitting source in the reusable part via optical means, in the disposable part, to the probe and into the body. The emitted light interacts with ISF analytes and returns back through the probe, and through optical means, to a detector in the reusable part to be analyzed by the processes.

In some embodiments, the monitoring of analyte levels within the monitoring device is based on optical properties of the analyte (e.g., glucose). The optical detecting method is based on at least one optical detection method, e.g., visible, NIR reflectance, mid-IR, infrared (IR), spectroscopy, light scattering, Raman scattering, fluoroscopy, polarimetry, PA spectroscopy, or any other optical techniques. Monitoring may also be based on a combination of several optical methods.

In some embodiments, the monitoring apparatus employs optical means, combined with electrochemical means, acoustic means, or any other means known in the art.

In some embodiments, the monitoring device is capable of monitoring analyte concentration levels in the body by directly monitoring subcutaneous ISF, or fluids comprising endogenous components of the ISF, inside the body.

In some embodiments, the patch unit includes a dispensing apparatus. The monitoring apparatus continuously monitors analyte concentration levels in the body and the dispensing apparatus continuously infuses fluid into the body.

In some embodiments, the monitoring apparatus continuously monitors glucose levels in the body, and the dispensing apparatus continuously delivers insulin into the body.

In some embodiments, the monitoring device works as a closed loop system that regulates body analyte concentrations by concomitantly monitoring analyte levels and dispensing fluid. The operation of the dispensing of fluid is regulated according to the sensed analyte concentration. Alternatively, the monitoring device may work as a semi-closed loop system, where the dispensing of fluid is regulated according to the sensed analyte concentration and according to external user inputs.

In some embodiments, the monitoring apparatus and the dispensing apparatus are contained within a patch unit. The dispensing apparatus comprises a fluid reservoir, driving mechanism and pumping mechanism. The monitoring apparatus and dispensing apparatus share the same electronics including processor and power supply. In the two-part patch unit, the dispensing apparatus is divided between the reusable and disposable parts. The pumping mechanism can be any piston/plunger, peristaltic, or pumping mechanism known in the art. The power supply can be contained in the reusable part or the disposable part. The patch unit can be connected to a probe that provides optical monitoring means for the monitoring apparatus and delivery means for the dispensing apparatus.

In some embodiments, the monitoring of analyte levels and the dispensing of fluid are both done through a single probe.

In some embodiments, the monitoring device includes more than one probe, where fluid dispensing (e.g, of insulin) is carried out through a cannula and the monitoring of analyte concentration levels (e.g., glucose) is effected through at least one additional probe.

In some embodiments, the monitoring device detects analyte concentration levels by means of a subcutaneous probe, where the insertion of the probe can be done manually or automatically by a dedicated inserter.

In some embodiments, the monitoring device comprises a remote control unit for displaying monitoring information, for data acquisition, and for issuing instructions.

In some embodiments, the display, controlling and data acquisition functions of the monitoring device are included in the patch unit, eliminating the need for a remote control unit.

In some embodiments, a single monitoring device monitors glucose levels, concomitantly delivers insulin, is miniature, discreet, economical for the users and highly cost-effective.

In some embodiments, the monitoring device monitors glucose and dispenses insulin using a single subcutaneous probe and avoids repeated skin pricking.

In some embodiments, the monitoring device concomitantly monitors glucose and dispenses insulin at the same insertion site.

Thus, it is an object of some of the embodiments to provide a monitoring device that contains a miniature, skin adherable unit that continuously monitors bodily analyte levels accurately and reliably.

It is an object of some of the embodiments to monitor analyte levels by performing discrete, high-rate measurements, in an essentially continuous manner.

It is an object of some of the embodiments to continuously monitor subcutaneous ISF analyte levels by optical means.

It is an object of some of the embodiments to monitor ISF glucose levels, for use by diabetes patients.

It is an object of some of the embodiments to monitor analyte concentration levels in the body by using optical means that are capable of directly monitoring subcutaneous ISF analyte levels.

It is an object of some of the embodiments to monitor ISF glucose levels in diabetes patients.

It is an object of some of the embodiments to provide a monitoring device that has a thin profile and relatively small footprint (i.e., discreet) and contains at least one of the following units: patch unit, cradle unit, cartridge unit, or remote control unit.

It is an object of some of the embodiments to provide a patch unit that can be configured as a single unit or as a two-part unit having a reusable part and disposable part. The reusable part may contain a light-emitting source, detector, electronics, and other relatively expensive components, and the disposable part may contain optical means and other inexpensive components. Batteries can reside in the disposable part or in the reusable part. This provides a simple and low-cost product for the user and a highly profitable product for the manufacturer and payer.

It is an object of some of the embodiments to detect analyte concentration levels by means of a single subcutaneous probe, through which light is passed from the patch unit to the user's body and back to the patch unit.

It is an object of some of the embodiments to provide a monitoring device and a method for monitoring analytes (e.g., glucose) comprising a combination of at least one or more optical monitoring methods, and/or one or more non-optical physical methods and/or one or more electro-chemical methods for monitoring analytes.

It is an object of some of the embodiments to provide a monitoring device that monitors glucose levels and concomitantly dispenses insulin.

It is an object of some of the embodiments to provide a monitoring device that monitors glucose using a subcutaneous probe, and dispenses insulin, using another subcutaneous probe.

It is an object of some of the embodiments to provide a closed loop or semi-closed loop system that dispenses therapeutic fluid according to continuous, real-time monitoring of analyte levels.

BRIEF DESCRIPTION OF THE DRAWINGS

FIGS. 7a-d show probe insertion through a cradle unit. FIGS. 7e-f show an embodiment of the cartridge unit and withdrawl of the penetrating member. FIG. 7g shows probe insertion through the patch unit.

DETAILED DESCRIPTION

Figure 1A:
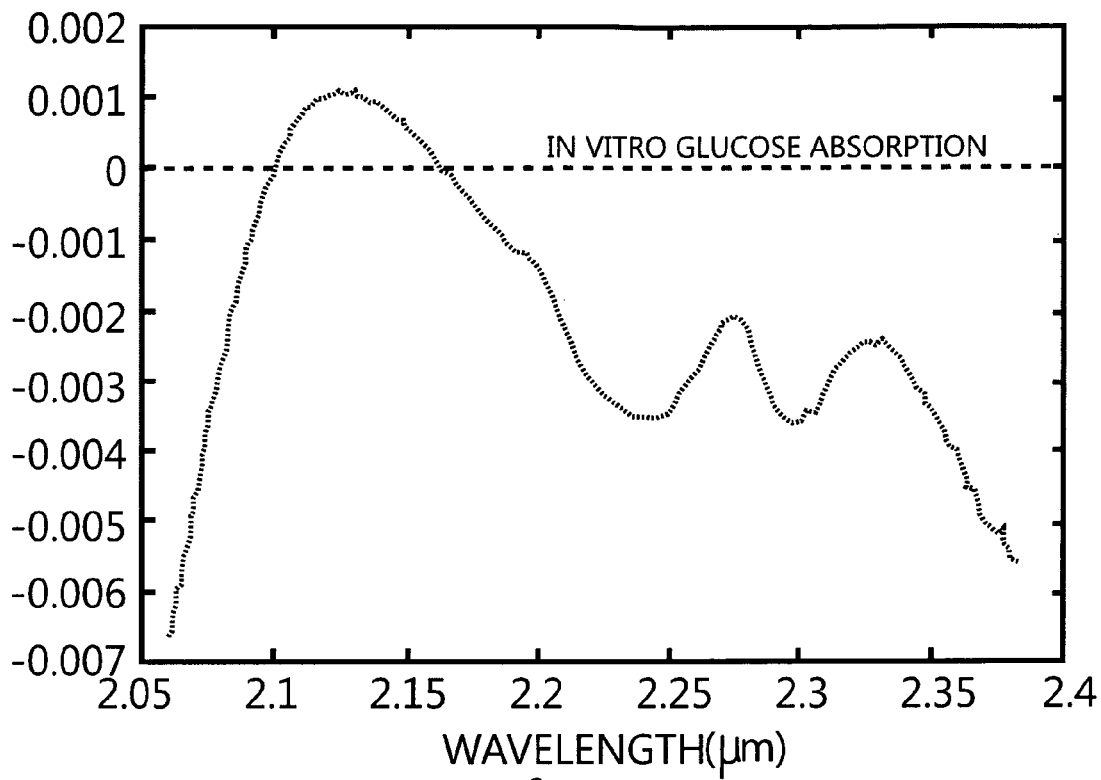
FIG. 1a shows optical absorption spectra of glucose in the NIR region for aqueous glucose after water subtraction as shown in the Journal of Biomedical Optics 5 (1), 5-16, Jan. 2000.
Figure 1B:
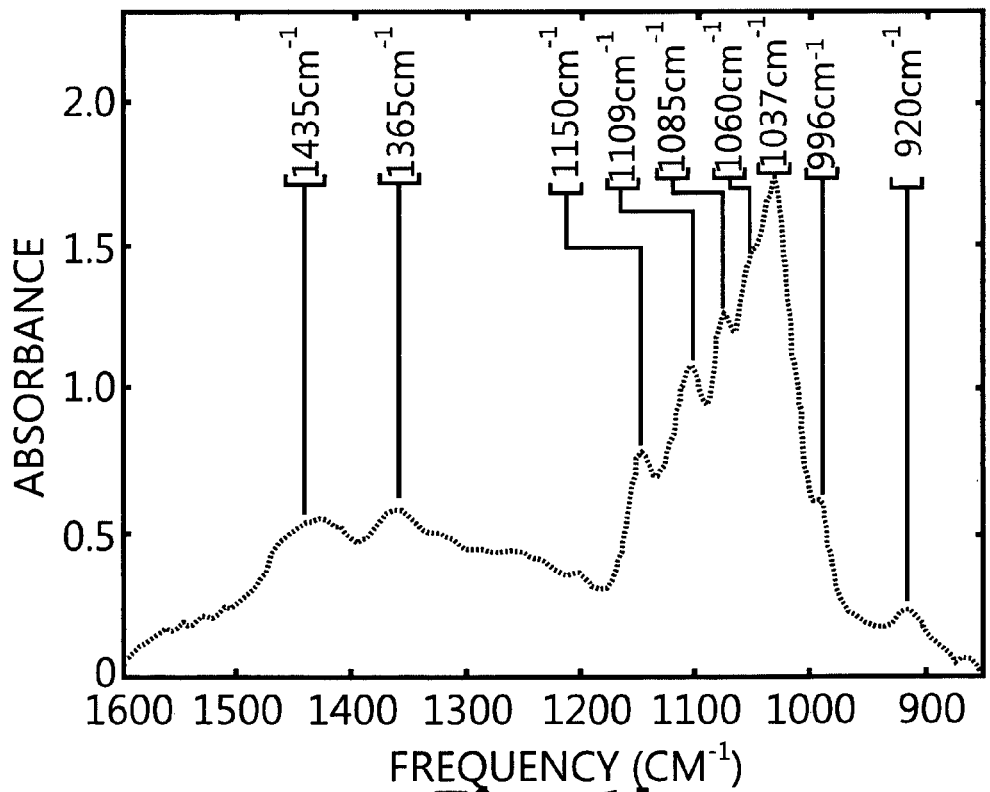
FIG. 1b shows optical absorption spectra of glucose in the mid-IR region for aqueous glucose after water subtraction as shown in the Journal of Biomedical Optics 5 (1), 5-16, Jan. 2000.
Figure 1C:
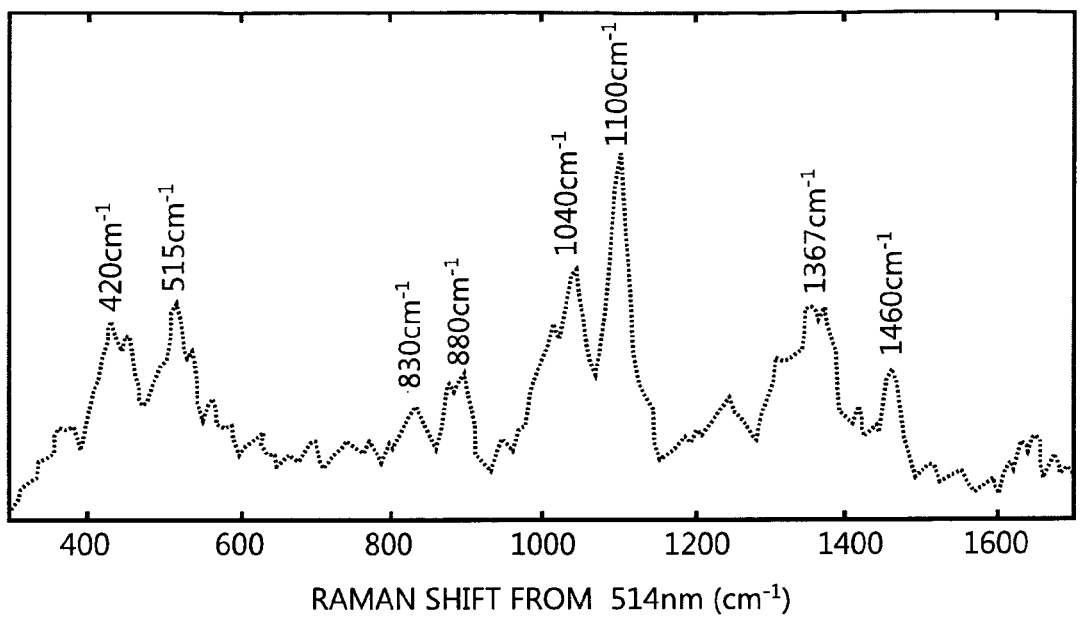
FIG. 1c shows the Raman spectrum for aqueous glucose, after subtraction of the water background as shown in the Journal of Biomedical Optics 5 (1), 5-16, Jan. 2000.

FIG. 1a shows optical absorption spectra of glucose in the NIR region for aqueous glucose after water subtraction as shown in the Journal of Biomedical Optics 5 (1), 5-16 Jan. 2000.

Figure 2A:
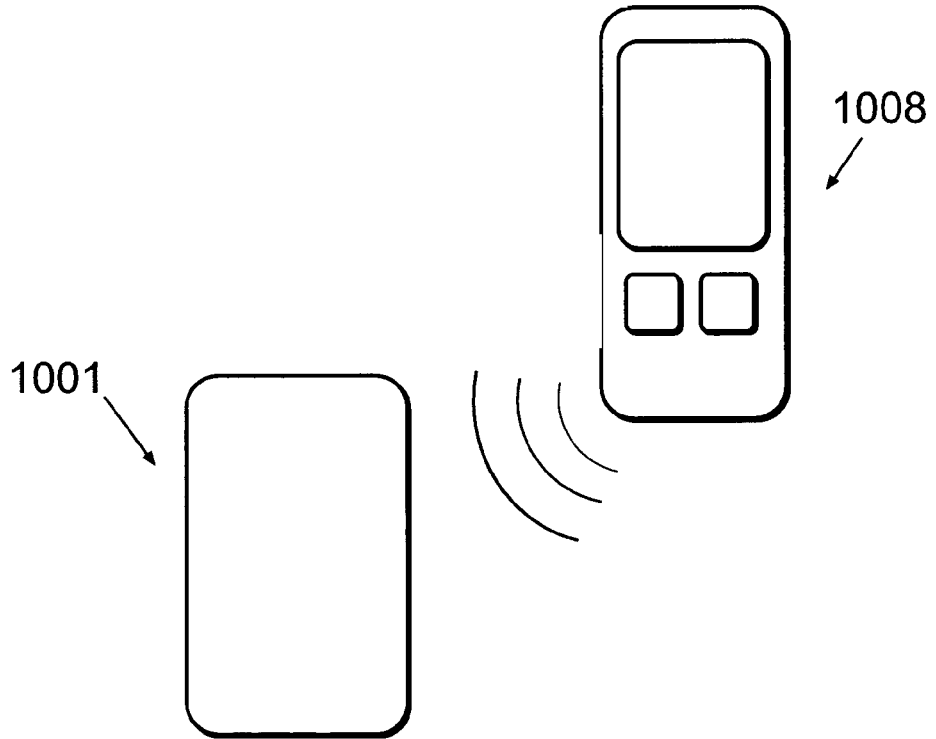
FIG. 2 shows (a) a single-part patch unit and a remote control unit (b) a single-part patch unit, and (c) a two-part patch unit.
Figure 2B:
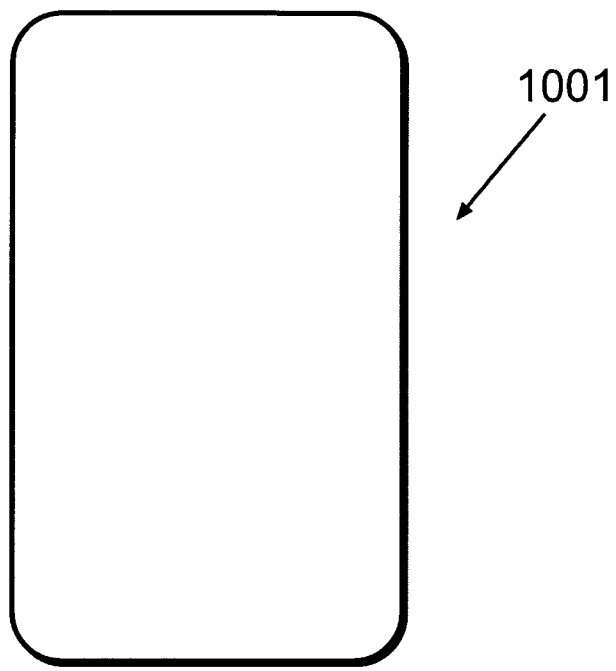
Figure 2C:
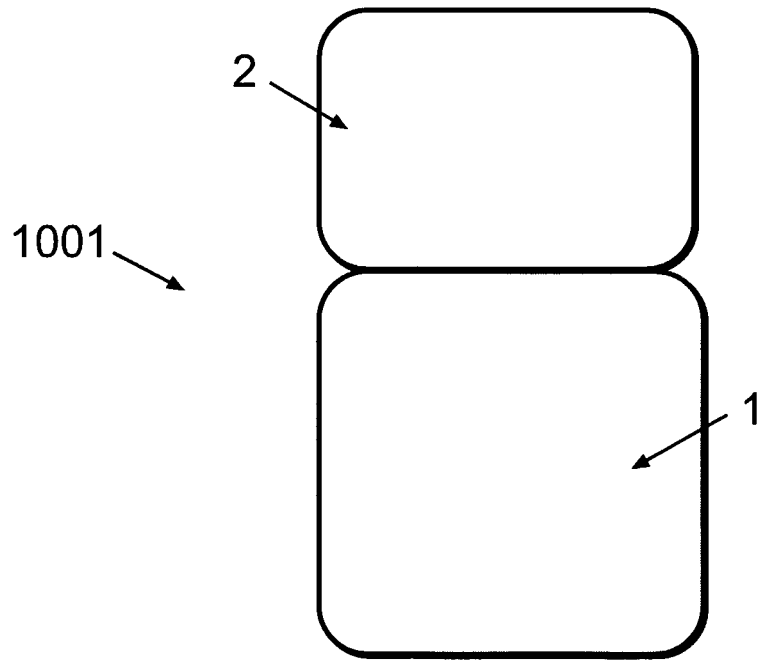

FIG. 2a shows a monitoring device composed of a patch unit (1001) and a remote control unit (1008). In accordance with one embodiment, the patch unit (1001) may be composed of a single part (FIG. 2b) or two parts (FIG. 2c): a reusable part (1) and a detachable disposable part (2), wherein each part is enclosed in its own housing. The patch unit (1001) can be programmed by the remote control unit (1008) or by the use of manual buttons (not shown) provided on the patch unit (1001).

Figure 3A:
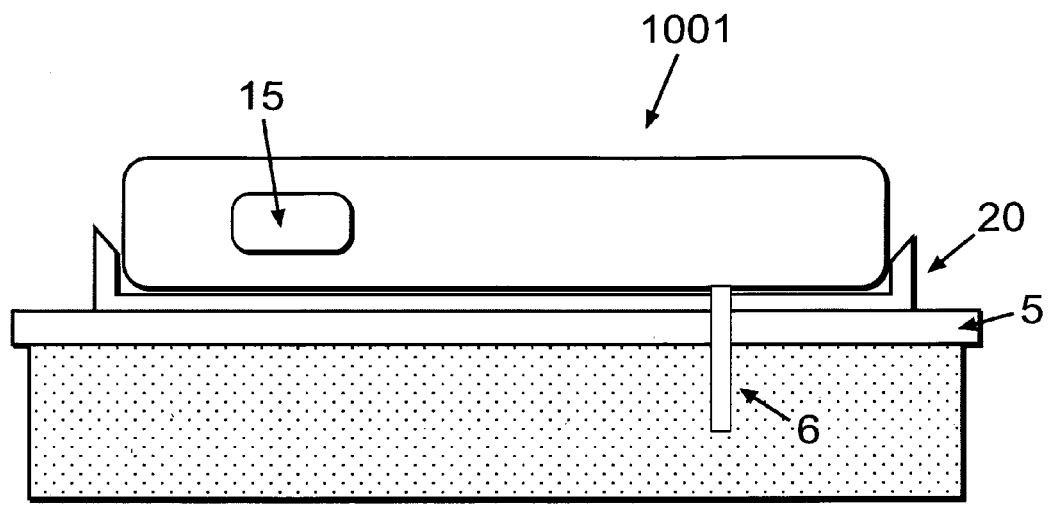
FIG. 3 shows (a) a single-part patch unit and a cradle unit for adherence to the skin, (b) a two-part patch unit and a cradle unit for adherence to the skin, (c) a single-part patch unit adhered directly to the skin, and (d) a two-part patch unit adhered directly to the skin.
Figure 3B:
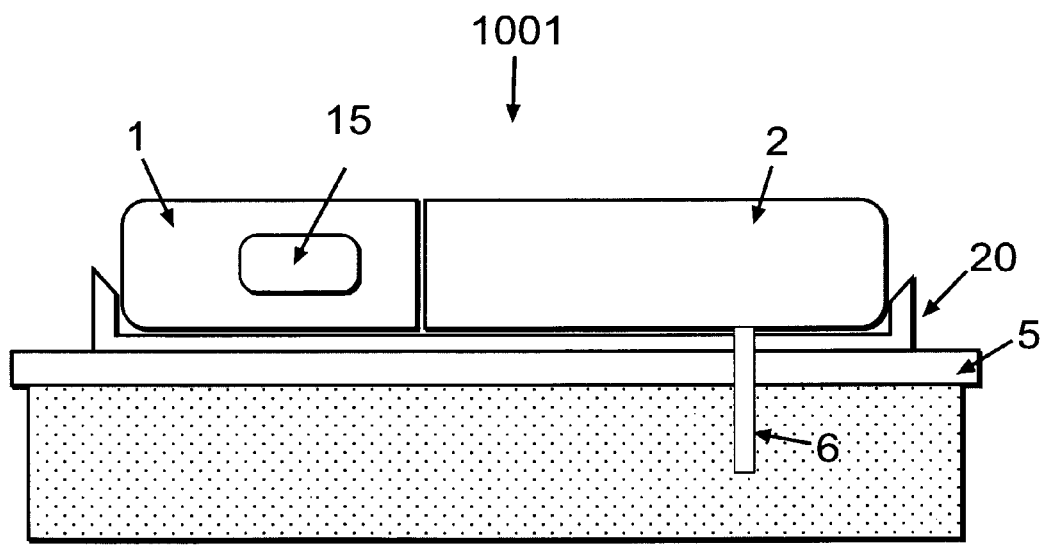
Figure 3C:
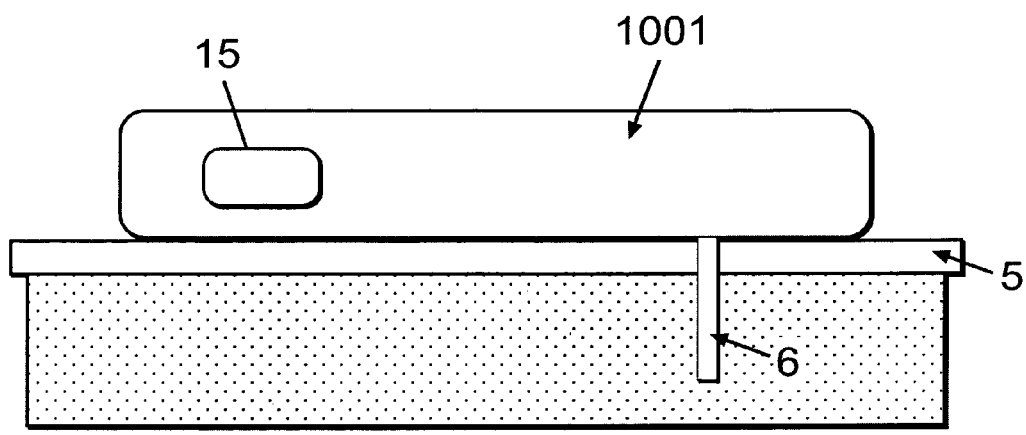
Figure 3D:
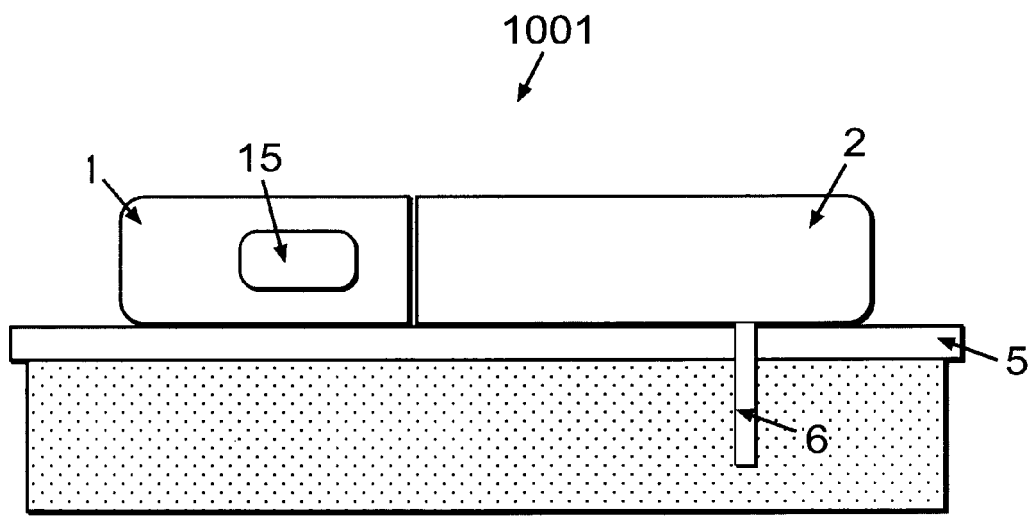

FIGS. 3a-d show embodiments for connecting the patch unit (1001) to the user's skin (5). FIGS. 3a-b show embodiments of the patch unit (1001) that can be comprised of a single part (FIG. 3a) or two parts (FIG. 3b): a reusable (1) and a disposable part (2). The patch unit (1001) can be connected to and disconnected from a skin (5) adherable cradle unit (20). In some embodiments, manual buttons (15) are located on the patch unit (1001). A probe (6) is rigidly anchored to the cradle (20) after insertion into the subcutaneous tissue. A detailed description of probe insertion is described in FIG. 7. FIGS. 3c-d show embodiments of a monitoring unit (1001) comprising a single part (FIG. 3c) or two parts (FIG. 3d): a reusable (1) and disposable part (2). The patch unit (1001) is adhered directly to the user's skin (5). In some embodiments, manual buttons (15) are located on the patch unit (1001).

Figure 4A:
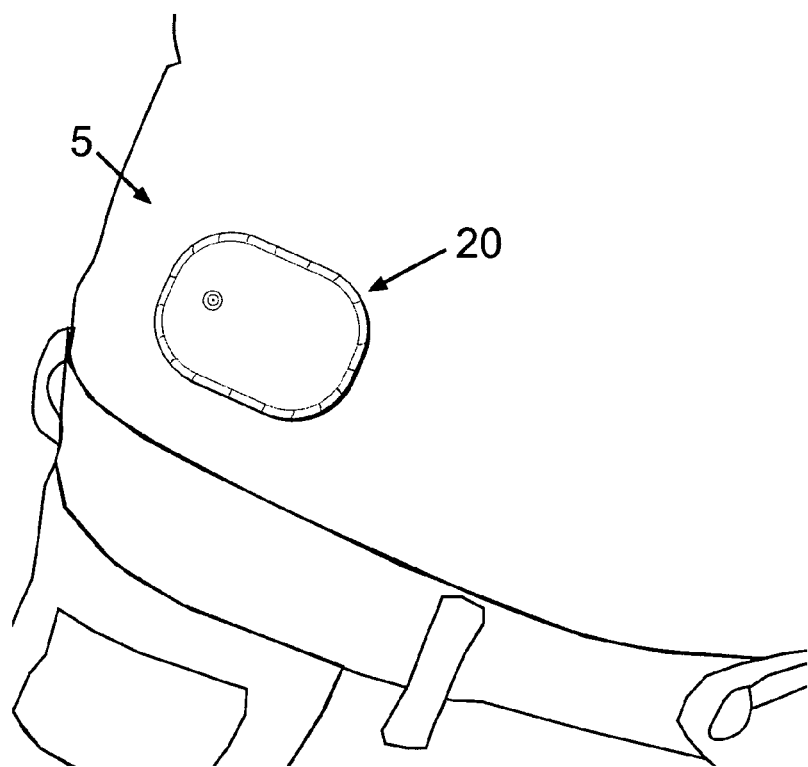
FIGS. 4a-c show a method for connection the patch unit to the body with the aid of a cradle unit.
Figure 4B:
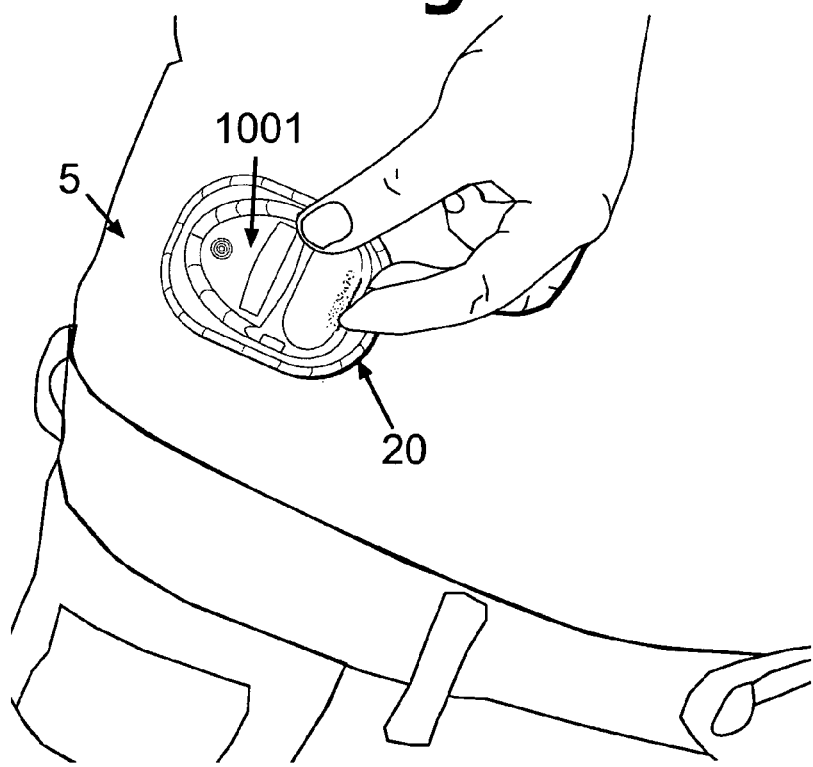
Figure 4C:
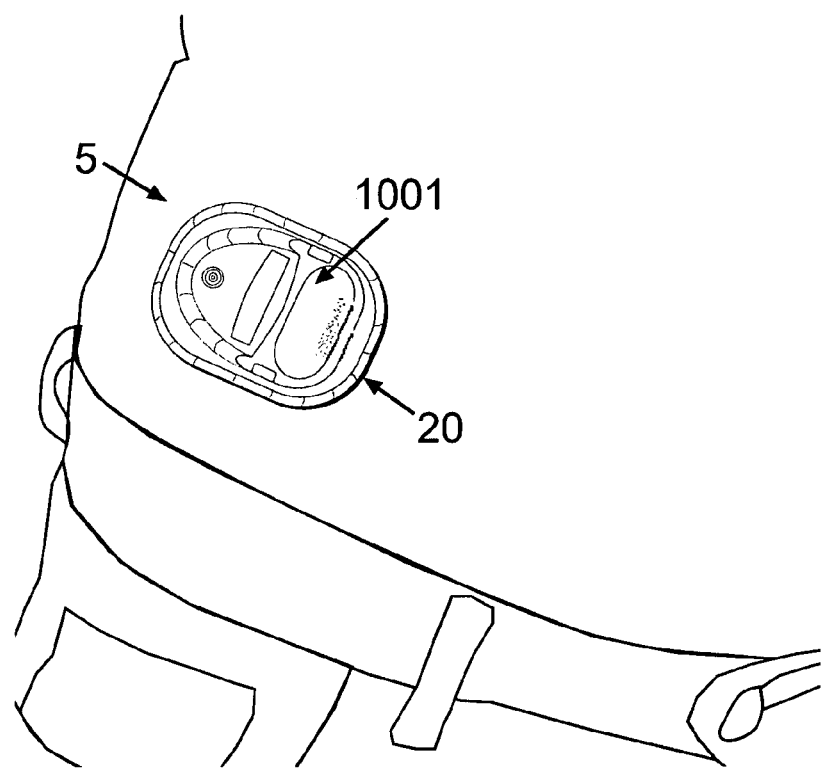

FIGS. 4a-c show an embodiment in which a cradle unit (20) is adhered first to the user's skin (5) and the patch unit (1001) can then be connected to and disconnected from the cradle unit (20) upon user discretion. FIG. 4a shows the cradle unit (20) adhered to the user's skin (5). FIG. 4b shows the connection of the patch unit (1001) to the skin-adhered cradle unit (20). FIG. 4c shows the patch unit (1001) connected to the cradle unit (20) and ready for operation.

Figure 5A:
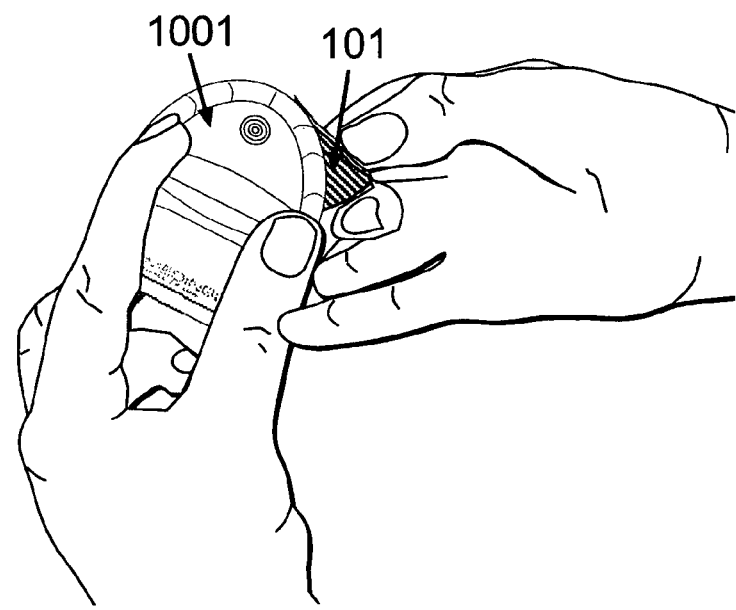
FIGS. 5a-c show a method for connection the patch unit to the body without the aid of a cradle unit (direct adherence to skin).
Figure 5B:
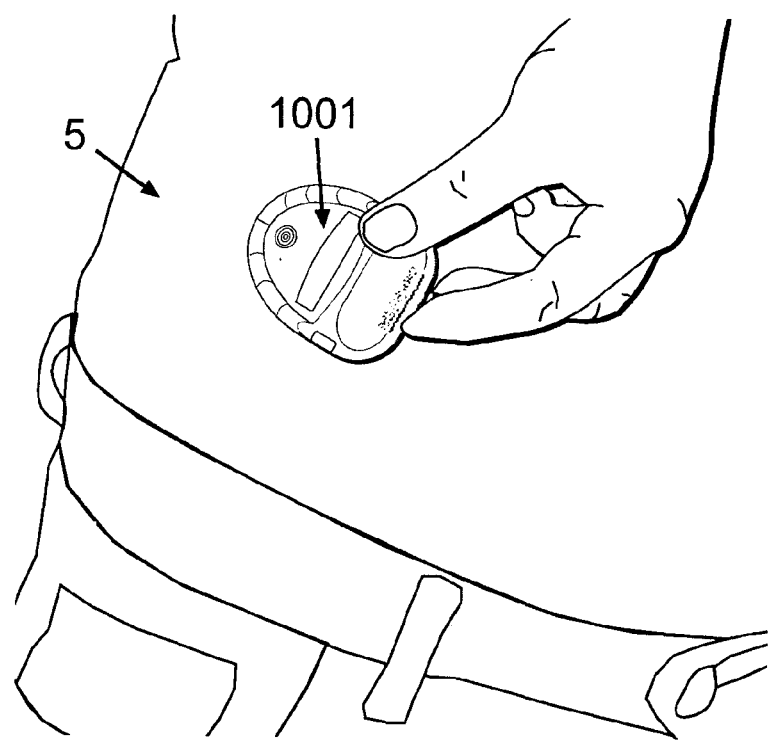
Figure 5C:
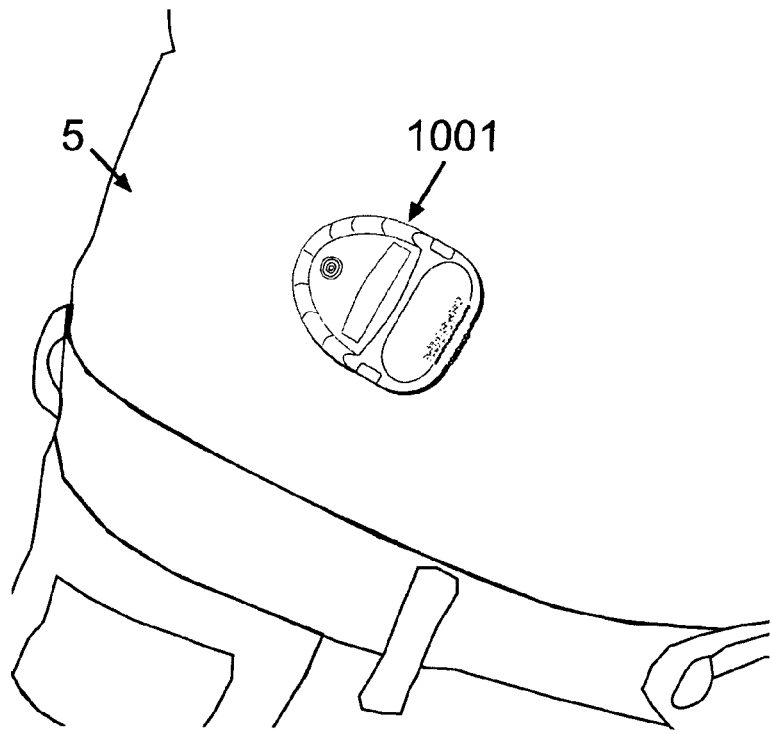

FIGS. 5a-c show another embodiment in which the patch unit (1001) is directly adhered to the user's skin (5). FIG. 5a shows the peeling of the adhesive protective sheet (101) from the lower face of the patch unit (1001). FIG. 5b shows the adherence of the patch unit (1001) to the user's skin (5). FIG. 5c shows the patch unit (1001) ready for operation.

Figure 6A:
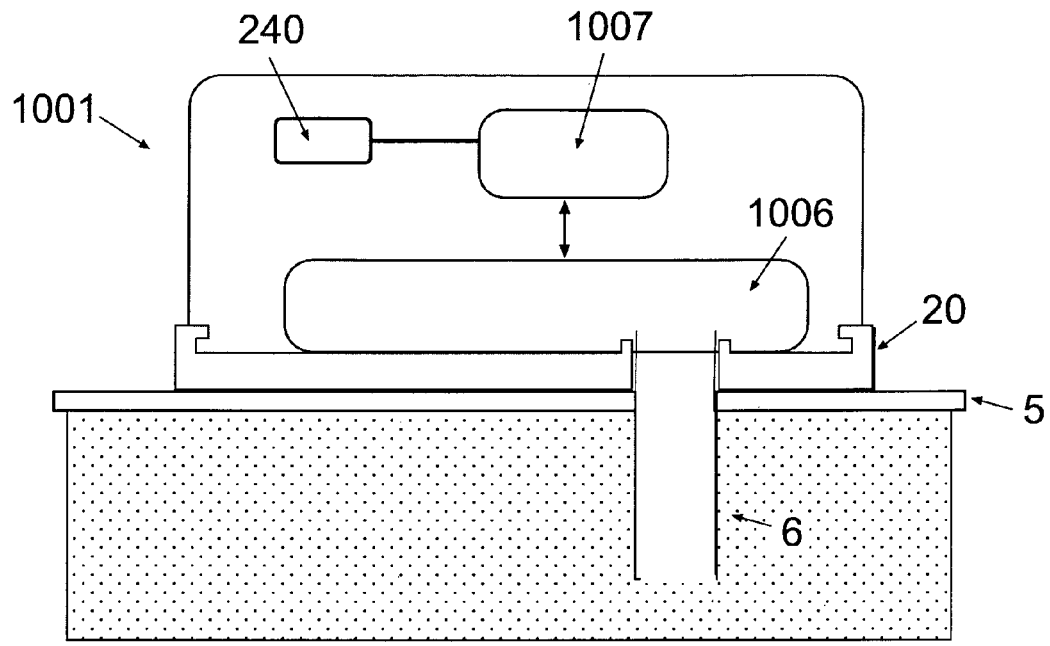
FIG. 6 shows the patch unit connected to a single probe (6a) and two probes (6b).
Figure 6B:
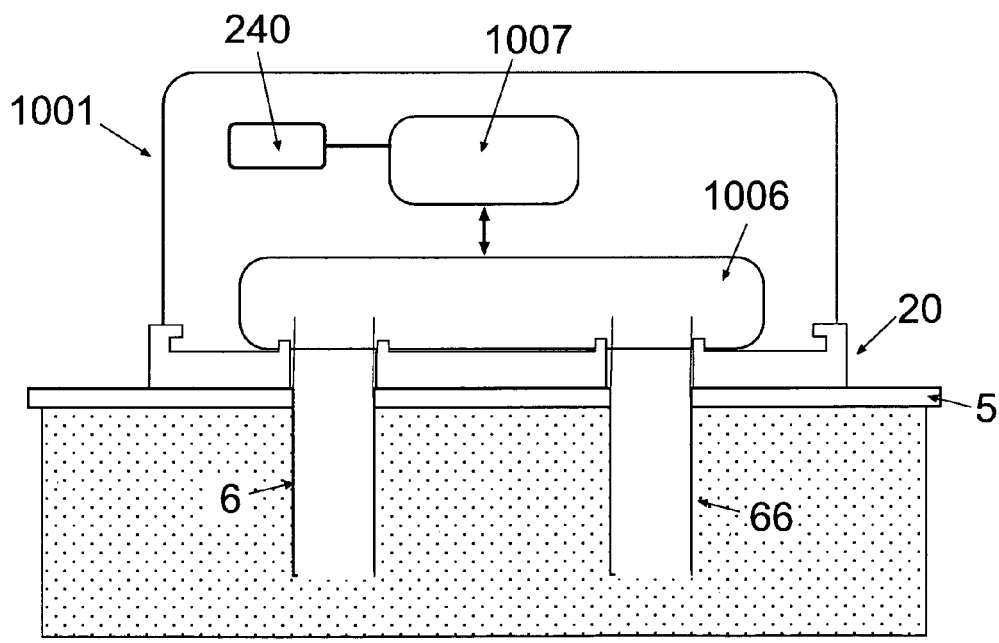

FIGS. 6a and 6b shows the components of the patch unit (1001) having an optically-based monitoring apparatus (1006), hereinafter "monitoring apparatus," energy supply (240) and a processor-controller (1007). The patch unit (1001) is connected to a probe (6) which is rigidly connected to the cradle unit (20). If the patch unit is directly adhered to the skin (FIGS. 5a-c), the probe is directly connected to the patch unit (1001). The monitoring apparatus (1006) comprises at least one light emitting source, and at least one light detector and the returned light spectra is analyzed by the processor-controller (1007) and can be presented to the user with the remote control unit (not shown) or directly with the patch unit (1001). The probe (6) is located within the user's body, under the skin (5), in the subcutaneous tissue. The probe (6) serves as a means for transmitting light from the monitoring apparatus (1006) to the user's body and back to the monitoring apparatus (1006). FIG. 6a shows an embodiment in which the monitoring device comprises a single probe (6). FIG. 6b shows an embodiment in which the monitoring device comprises two probes (6, 66) for performing the monitoring operation. Both probes (6, 66) are located in the subcutaneous tissue allowing analyte concentration level measurements in the user's body.

Figure 7A:
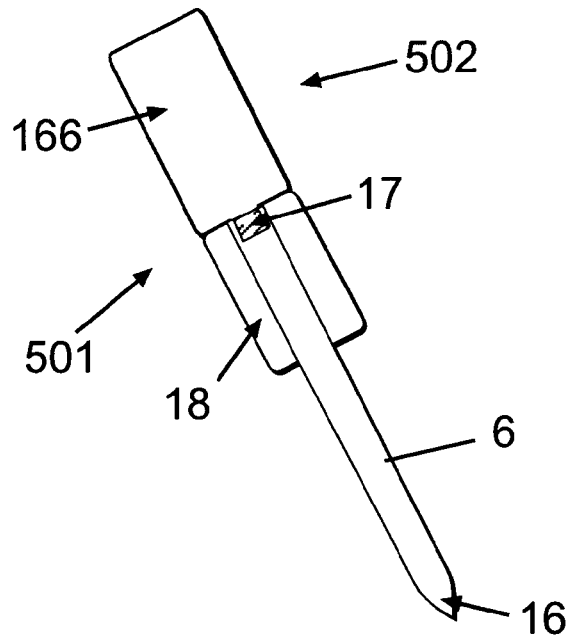
FIGS. 7a-g show the insertion of the monitoring probe into the body.
Figure 7B:
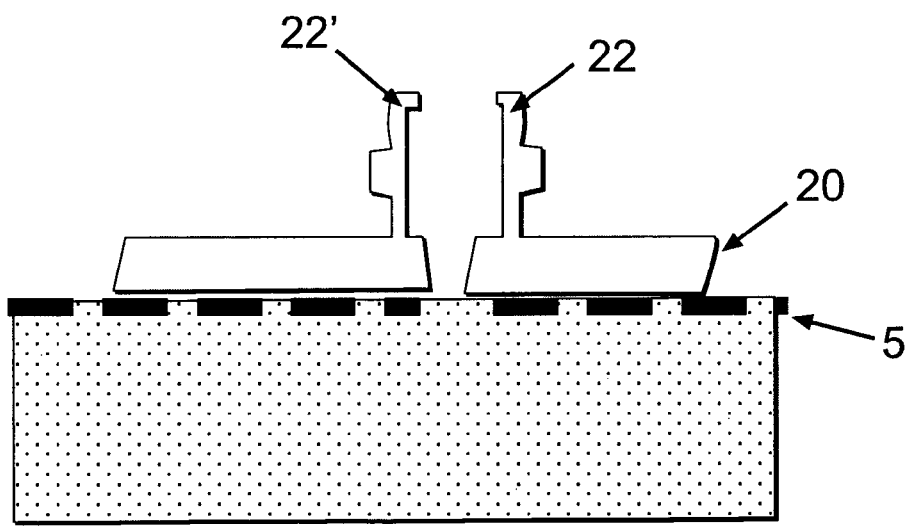
Figure 7C:
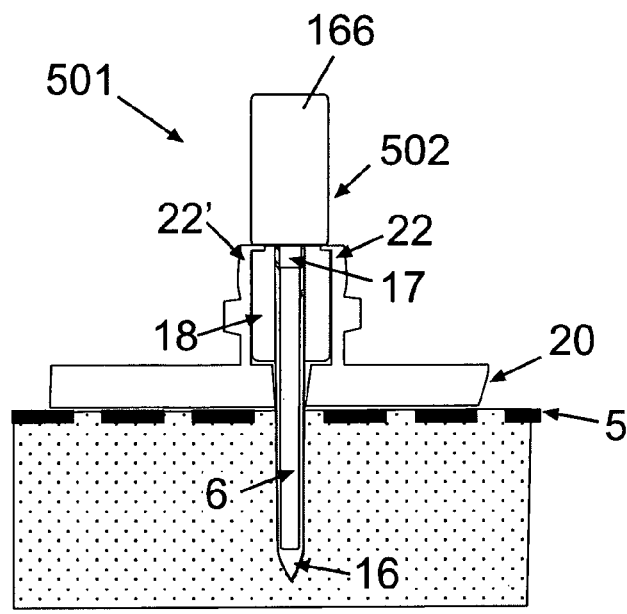
Figure 7D:
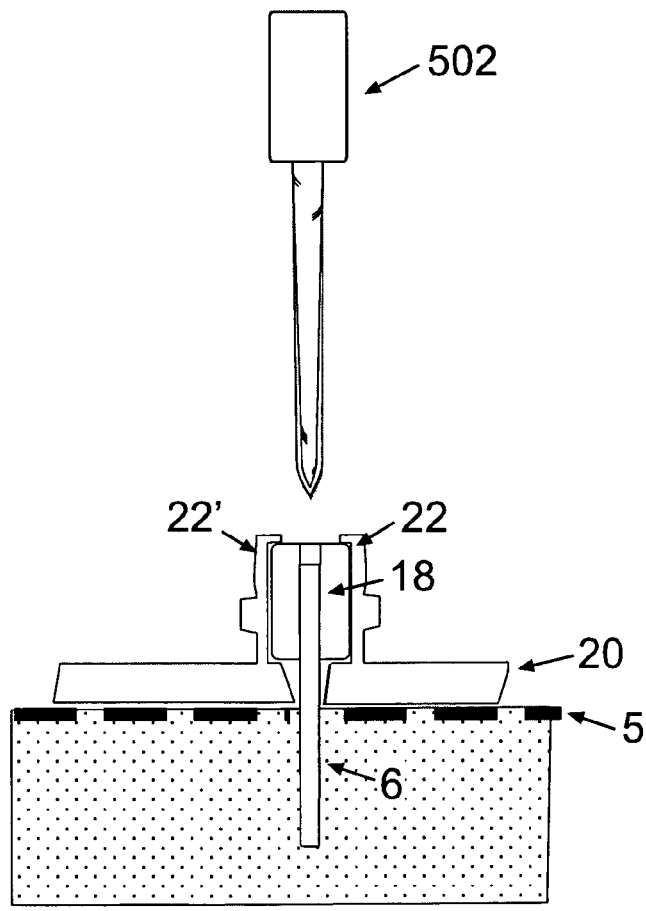
Figure 7E:
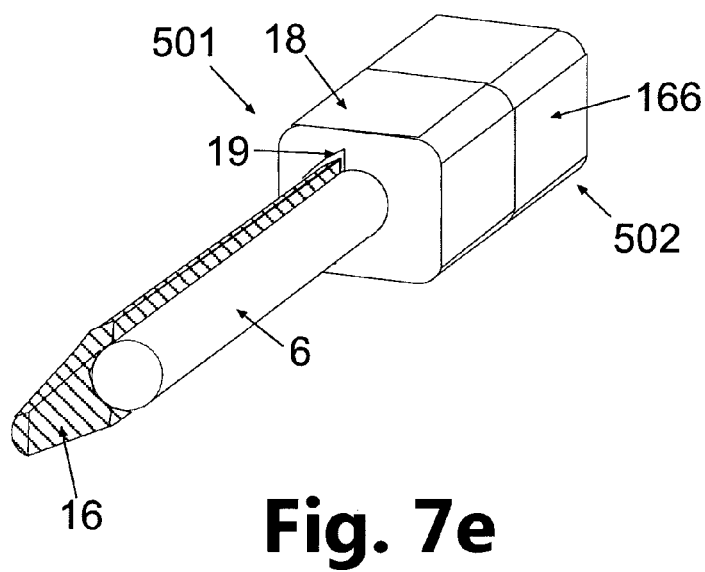
Figure 7F:
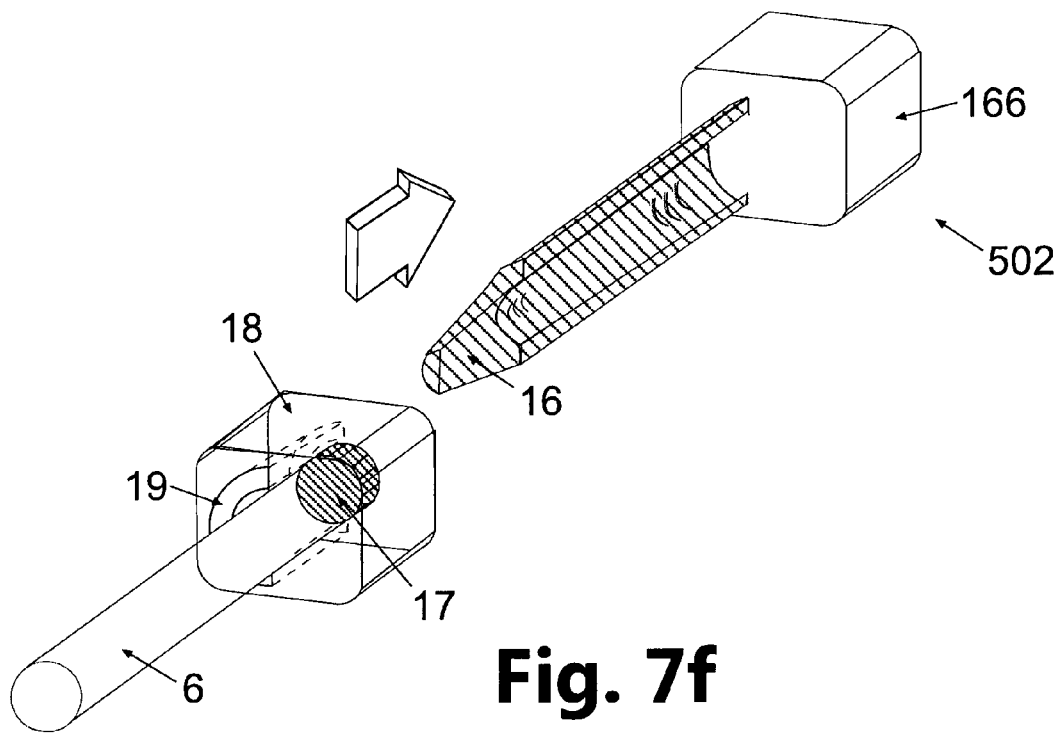
Figure 7G:
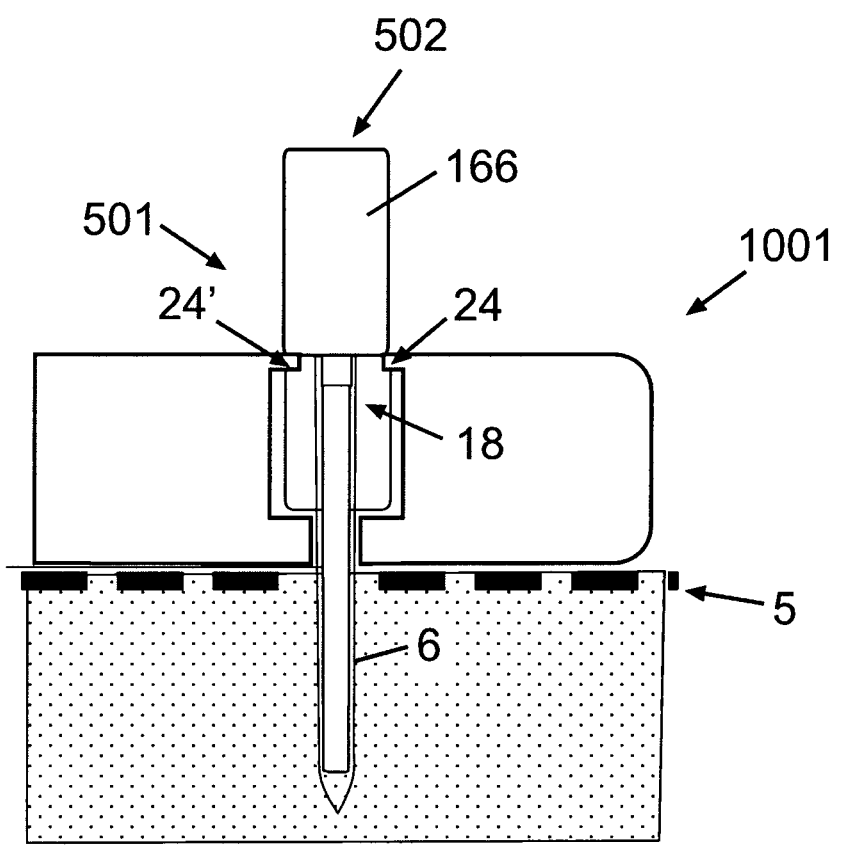

FIGS. 7a-7g show the insertion process of the probe (6) into the body. FIG. 7a shows an embodiment of a cartridge unit (501), which may have a penetrating member (502) with a sharp edge 16 partially surrounding the probe (6) and a cap 166. An optical means (e.g., lens) 17 is located at the upper portion of the probe within a probe hub 18. FIG. 7b shows a partial cross-section view of the cradle unit (20) adhered to the skin (5) of the user and anchoring means 22 and 22' for the probe (6). Adherence of the cradle unit (20) to the skin (5) is carried out by virtue of adhesive means (not shown) located on the bottom side of the cradle unit (20). FIG. 7c shows the insertion of the probe (6) using the cartridge unit (501). The penetrating member (502) pricks the skin (5) and the probe (6) remains rigidly anchored to the anchoring means 22 and 22'. Insertion of the probe (6) may be carried out manually or via a dedicated inserter (not shown) which can insert a probe in a similar way as an insertion of a cannula (not shown), as described in our co-pending, co-owned International Patent Application No. PCT/IL2008/000860 and U.S. patent application Ser. No. 12/215,255, each titled "An Insertion Device" filed on Jun. 25, 2008, and claiming priority to U.S. Provisional Application Nos. 60/937,155, 60/937,214 and 60/937, 163, filed on Jun. 25, 2007, all of which are incorporated by reference herein in their entireties. FIG. 7d shows the withdrawal of the penetrating member (502), leaving the distal end of probe (6) in the body and the proximal end (probe hub 18) anchored to the cradle unit (20). FIG. 7e shows an embodiment of the cartridge unit (501). Sharp tip 16 crosses the probe hub 18 through a groove 19 and partially surrounds the probe (6). FIG. 7f shows withdrawal of the penetrating member (502). FIG. 7g shows another embodiment in which the probe (6) is inserted into the body below the skin (5) through the patch unit (1001). The probe hub 18 is anchored to the patch unit (1001) using anchoring means (24 and 24').

Figure 8A:
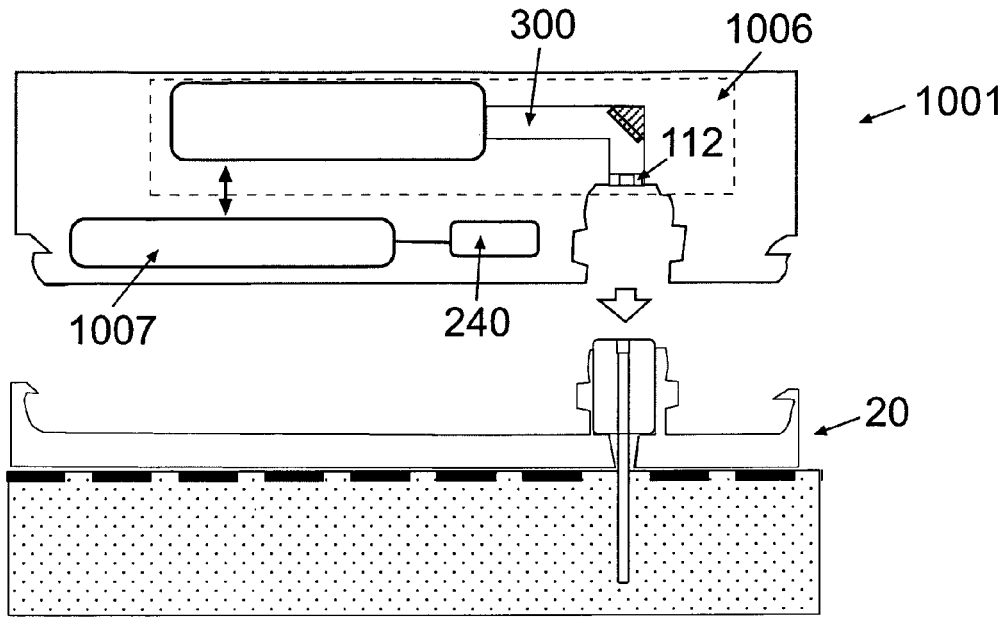
FIGS. 8a-b show the patch unit and the cradle unit before connection (8a) and after connection (8b).
Figure 8B:
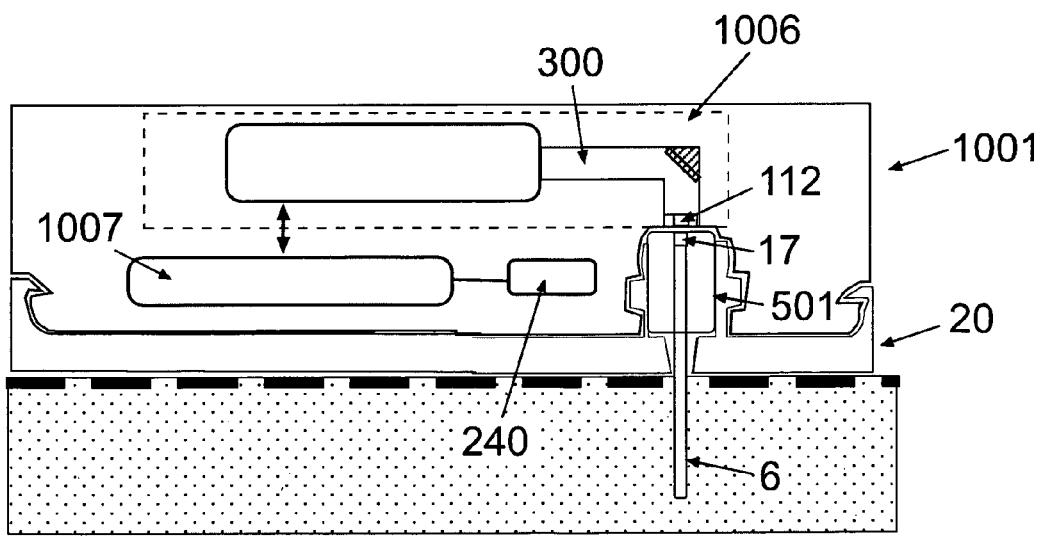

FIGS. 8a-b show the connection of the patch unit (1001) to the cradle unit (20). FIG. 8a shows a patch unit (1001) prior to its connection to the cradle unit (20). The patch unit (1001) contains monitoring apparatus (1006), processor-controller (1007), and energy supply (240). The monitoring apparatus (1006) includes an optical path (300) and a lens (112). Repetitive connection and disconnection of the patch unit (1001) to and from the cradle unit (20) are possible. FIG. 8b shows the patch unit (1001) connected to the cradle unit (20). Also shown are the monitoring apparatus (1006), processor (1007), energy supply (240), optical path (300), and lens (112). Lens (112) is shown in close proximity to the optical means (17) allowing light to be transferred from the probe (6) into the patch unit (1001).

Figure 9A:
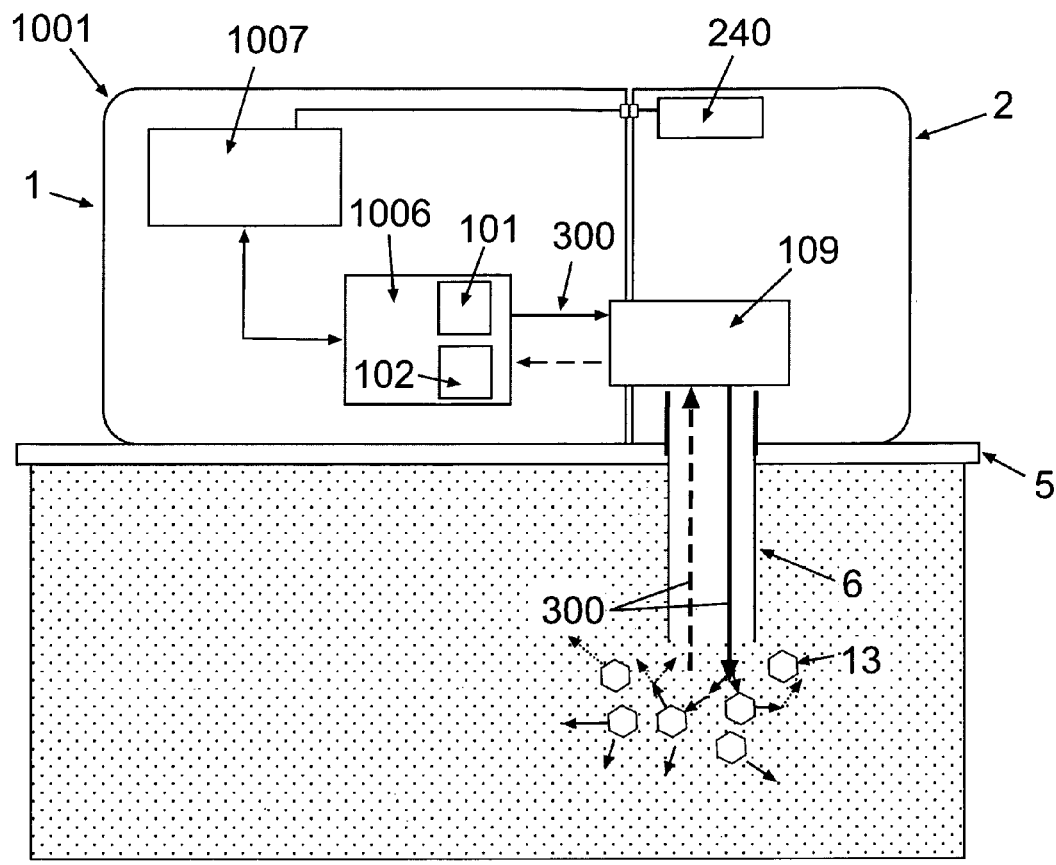
FIG. 9a shows the analyte monitoring process by the patch unit and the probe.
Figure 9B:
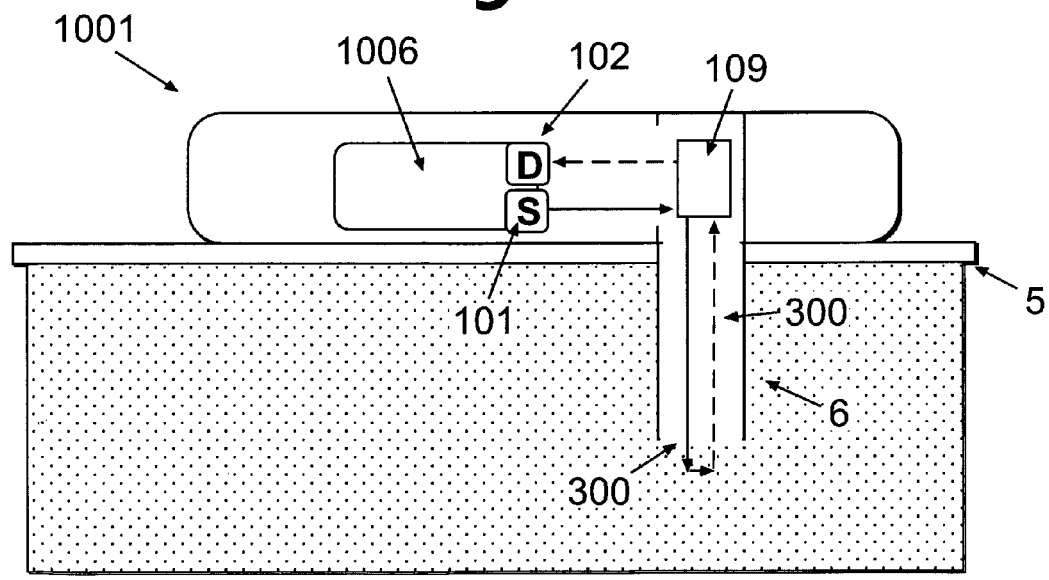
FIG. 9b shows the light path within the patch unit.

FIG. 9a shows an embodiment of a two-part patch unit (1001) having a reusable part (1) and disposable part (2). The monitoring apparatus (1006) includes at least one light-emitting source (101) and at least one detector (102). Light (300) is transmitted through an optical system (109) containing optical means (e.g., reflectors, optical fibers) and probe (6) to and from the body below the skin (5) for interaction with monitored analyte (13). Light spectra are analyzed by the processor-controller (1007). The energy supply (240) is contained in the disposable part (2) and, alternatively, can be located in the reusable part (1). The light (300) is transmitted to the ISF where light-analyte interactions occur, particularly interactions with (13), e.g., ISF glucose. The light (300) returns to the probe (6), due to interaction with the tissue, (e.g., diffuse reflectance), and is transmitted back to the detector (102) through the probe (6) and optical system (109). The detector (102) sends an electrical signal, corresponding to the detected light, to the processor-controller (1007), for obtaining analyte concentration levels. FIG. 9b shows the monitoring apparatus (1006) comprises a light-emitting source (101), hereinafter also designated in the text and drawings as "Source", or "S" and a detector (102), hereinafter also designated in the text and drawings as "Detector", or "D". Light (300) is emitted from the light-emitting source (101), through the optical system (109), through the probe (6), into the analyte-containing ISF in the user's body, and back to the detector (102) in the monitoring apparatus (1006). The optical system (109) transmits the light (300) by optical means (e.g. reflectors, lenses, optical fibers).

Figure 10A:
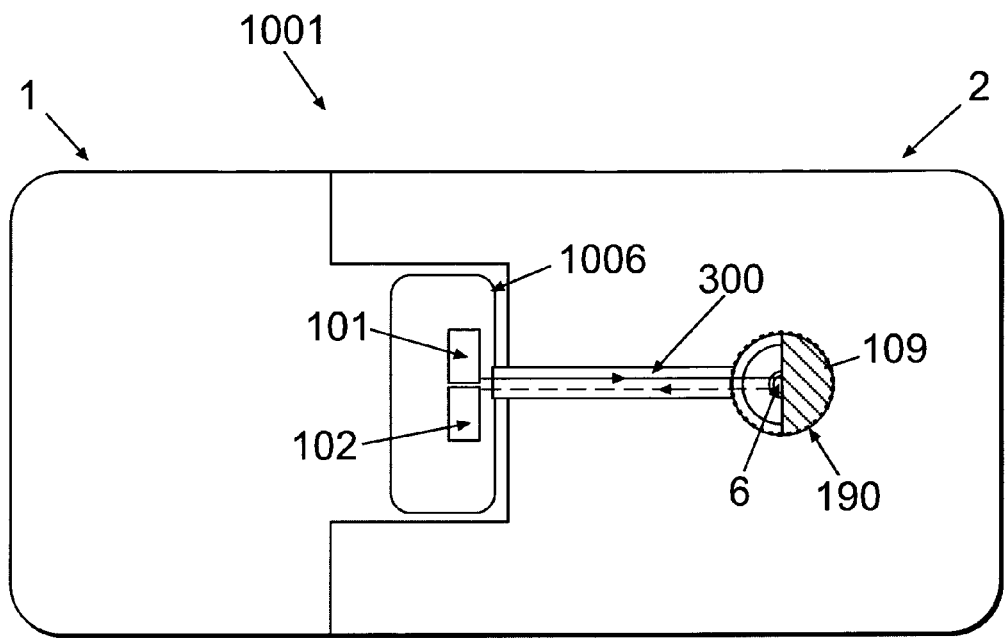
FIGS. 10a-b show a two-part patch unit comprising a reusable part and a disposable part. The monitoring apparatus includes components that are deployed within the two parts.
Figure 10B:
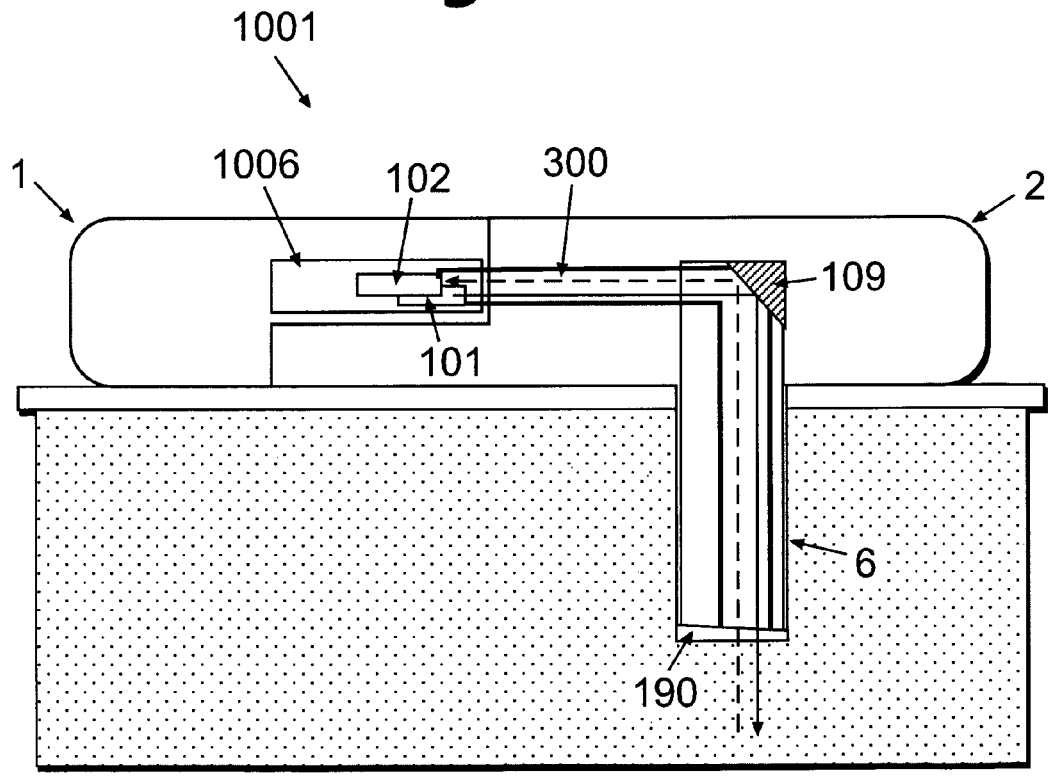
Figure 10C:
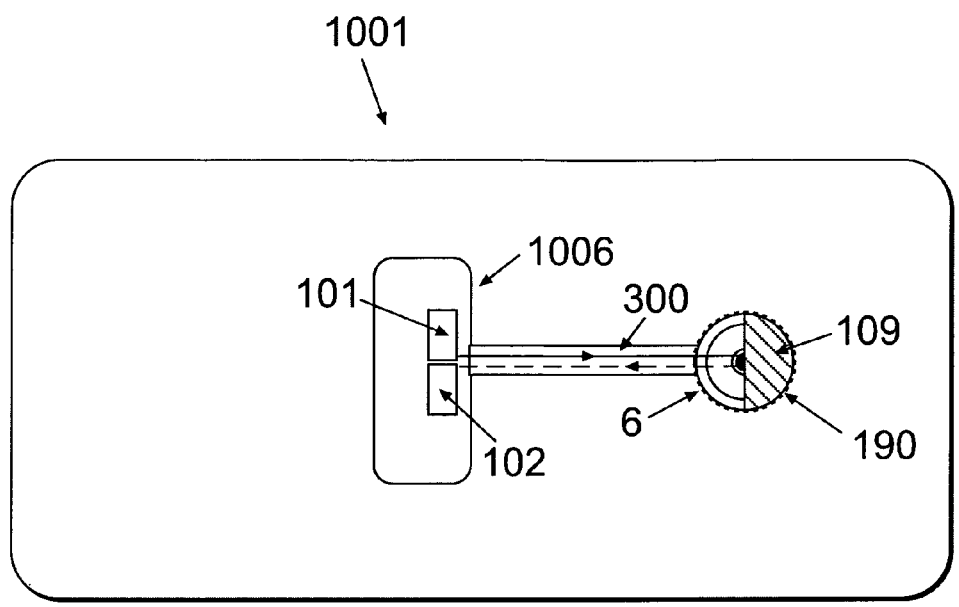
FIGS. 10c-d show a one part patch unit and the components of the monitoring device.
Figure 10D:
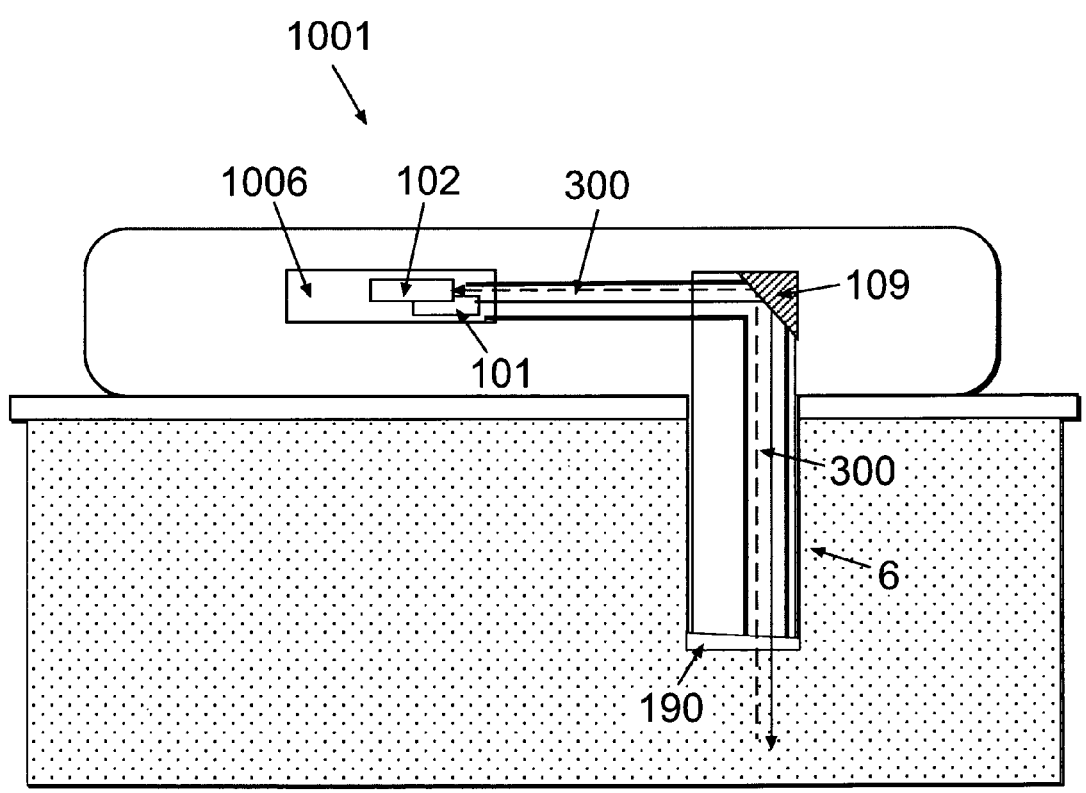

FIGS. 10a-b show an embodiment of a two-part patch unit (1001) having a reusable part (1) and a disposable part (2), and the passage of light (300) therebetween. FIG. 10a shows a top view of the patch unit (1001) with the reusable (1) and disposable (2) parts and FIG. 10b shows a side view of the patch unit (1001). The components of the monitoring apparatus (1006) may be located either in the reusable part (1) or the disposable part (2) of the patch unit (1001), according to their function and purpose. All relatively expensive, non-disposable components of the monitoring apparatus (1006), e.g., the source (101) and the detector (102), reside within the reusable part (1) of the patch unit (1001). Some components of the monitoring apparatus (1006), such as parts of the optical system (109) (e.g., lenses, reflectors), may reside within the reusable part (1) or disposable part (2). The transmission of light (300) between the patch unit (1001) and the body is enabled via optical means (e.g., reflectors, lenses, optical fibers) within the optical system (109). Particularly the optical means transmits the light (300) from the components of the monitoring apparatus (1006), through the probe (6) and to the body. In one embodiment, an optical coupler (190), (e.g., window), may be present at the end of the probe (6) inside the body to serve as an interface between the body tissue medium and the probe (6). The optical coupler (190) may also prevent specular reflection. For example, the optical coupler (190) may be a window inclined by an 8 degree angle. FIGS. 10c-d show an embodiment of a single part patch unit (1001) having a source (101), a detector (102), optical means, and an optical system (109). FIG. 10c shows a top view of the patch unit (1001) and FIG. 10d shows a side view of the patch unit (1001). The passage of light (300) from the patch unit (1001) to the body is enabled via optical means (e.g., reflectors, lenses, optical fibers), within the optical system (109). In one embodiment, an optical coupler (190), (e.g., window), is present at the end of the probe (6), inside the body, serving as an interface between the body tissue medium and the probe (6). The optical coupler (190) may also prevent specular reflection. For example, the optical coupler (190) may be a window inclined by an 8 degree angle.

Figure 11A:
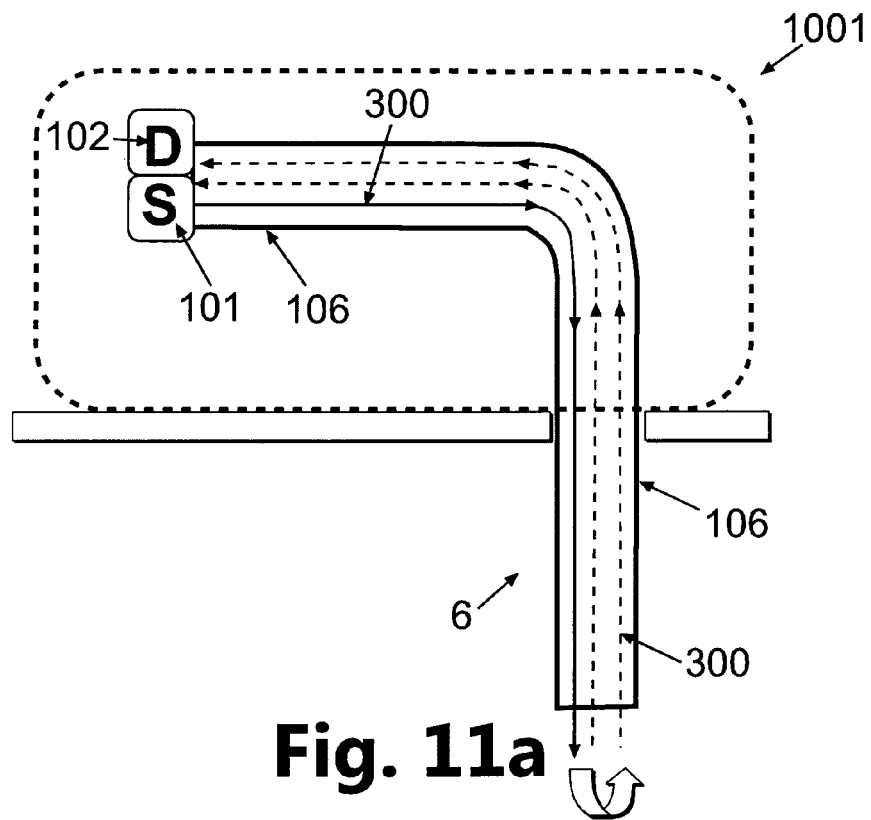
FIGS. 11a-f show embodiments of the monitoring device employing various optical means for directing light from the source to the body and back to the detector.
Figure 11B:
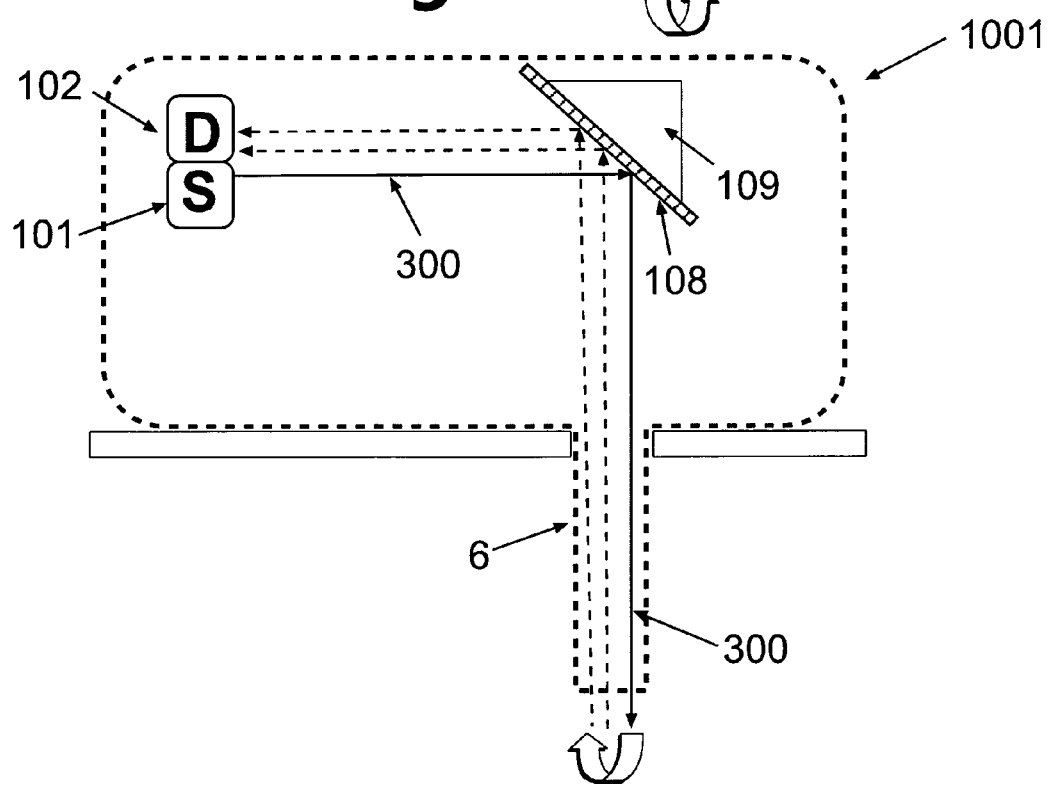
Figure 11C:
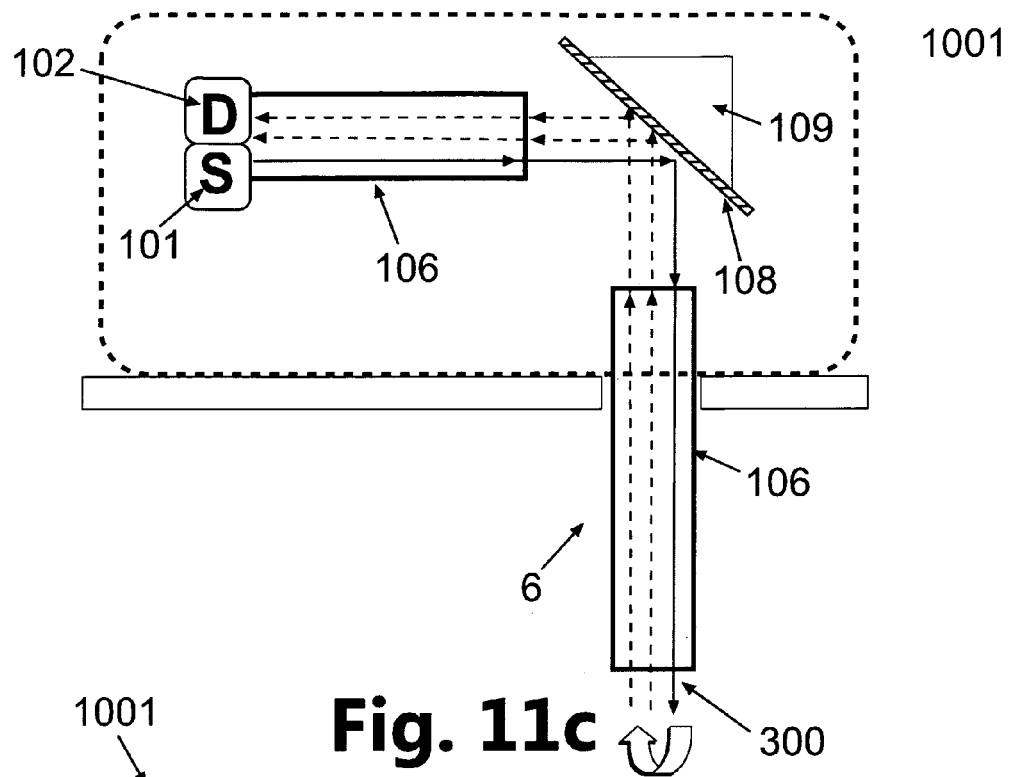
Figure 11D:
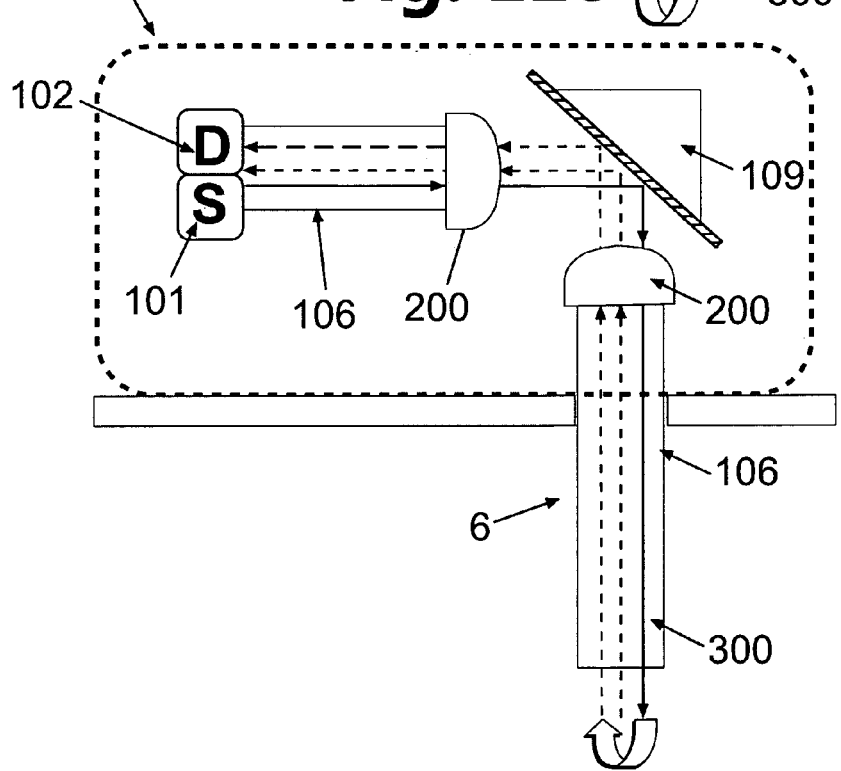
Figure 11E:
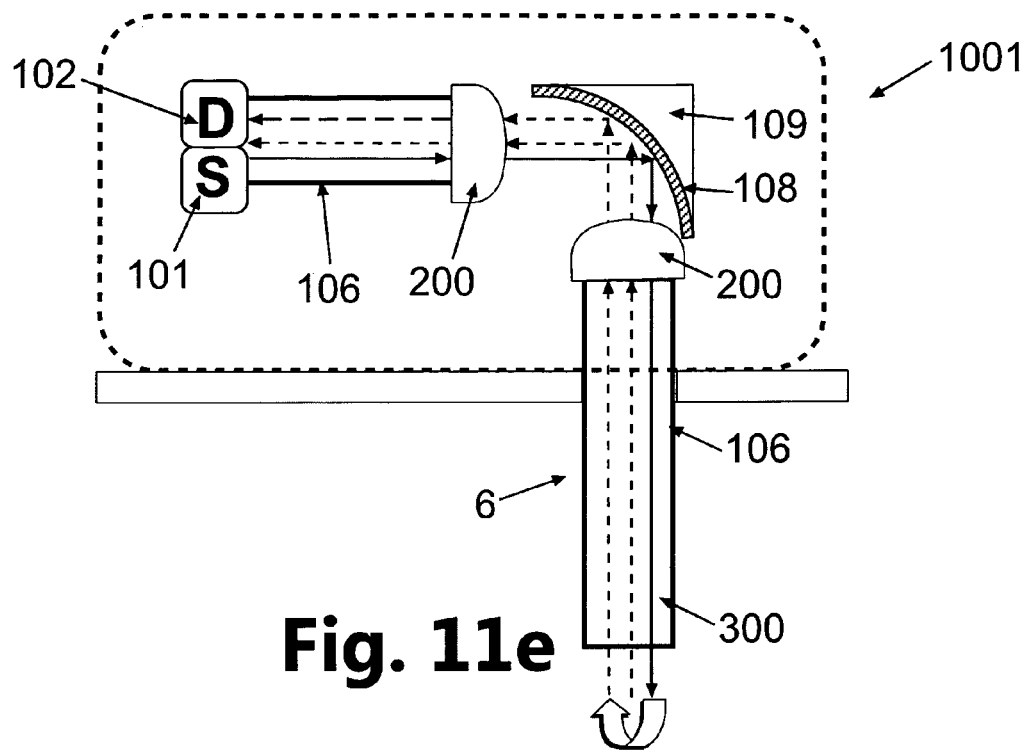
Figure 11F:
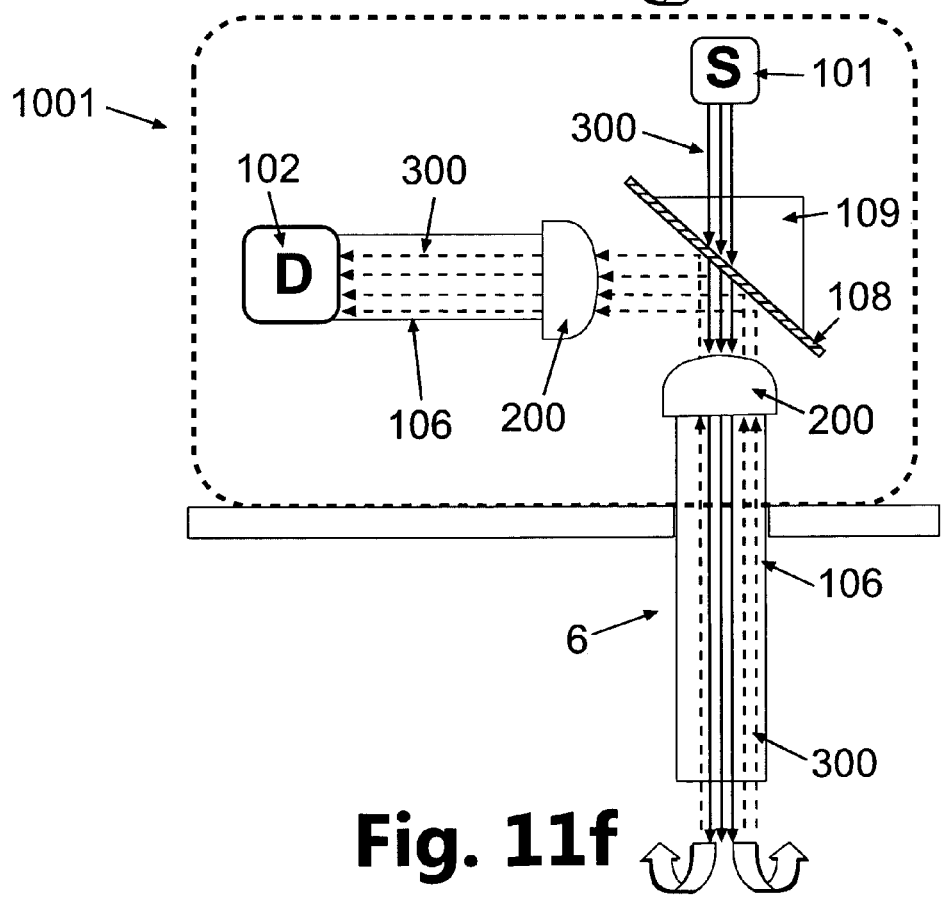

FIGS. 11a-f show embodiments of the patch unit (1001), employing various optical means for transmitting light (300) from the source (101), through the probe (6) to the body, and back to the detector (102). FIG. 11a shows an embodiment, in which the light (300) emitted from the source (101) in the monitoring apparatus (1006), passes through one or more optical fibers (106), which transmit the light (300) directly to the probe (6) into the body and back to the monitoring apparatus (1006). FIG. 11b shows another embodiment, in which one or more reflectors (108), (e.g. mirrors, prisms), within an optical system (109) are used to transmit the emitted light (300) towards the body, through the probe (6) and back to the monitoring apparatus (1006), without the use of optical fibers. FIG. 11c shows another embodiment, in which light emitted from the source (101) passes through an optical fiber (106), reaching an optical system (109), including reflectors (108), which transmits the light (300) towards an additional optical fiber (106) leading the light through the probe (6) to the body. The light that returns from the body passes through the same optical system (109), and is transmitted to the detector (102). FIG. 11d shows an embodiment in which a collimating lens (200) is present at the end of the optical fiber (106), such that the lens (200) gathers the light (300) in the optical fiber (106) in a parallel beam. The lens (200) is part of the optical system (109) transmitting the light (300). FIG. 11e shows an embodiment with collimating lens (200) and reflector (108) within the optical system (109). The reflector (108) may be parabolic, such that light (300) reflected off the reflector (108) is transmitted in an optimized direction. FIG. 11f shows an embodiment in which the reflector (108) within the optical system (109) is uni-directional. The surface on one side of the reflector (108) passes the light (300) that reaches it, and the surface on the other side of the reflector (108) reflects the light (300) that reaches it. Light (300) from the source (101) passes through the reflector (108) in the optical system (109) into the optical fiber (106) leading the light (300) through the probe (6) to the body. The returned light, passing through the probe (6) and optical fiber (106), reaches the optical system (109) and the reflector (108), which reflects the light (300) towards the detector (102). In this embodiment the light-emitting source (101) and the detector (102) may be located far apart or close together.

Figure 12A:
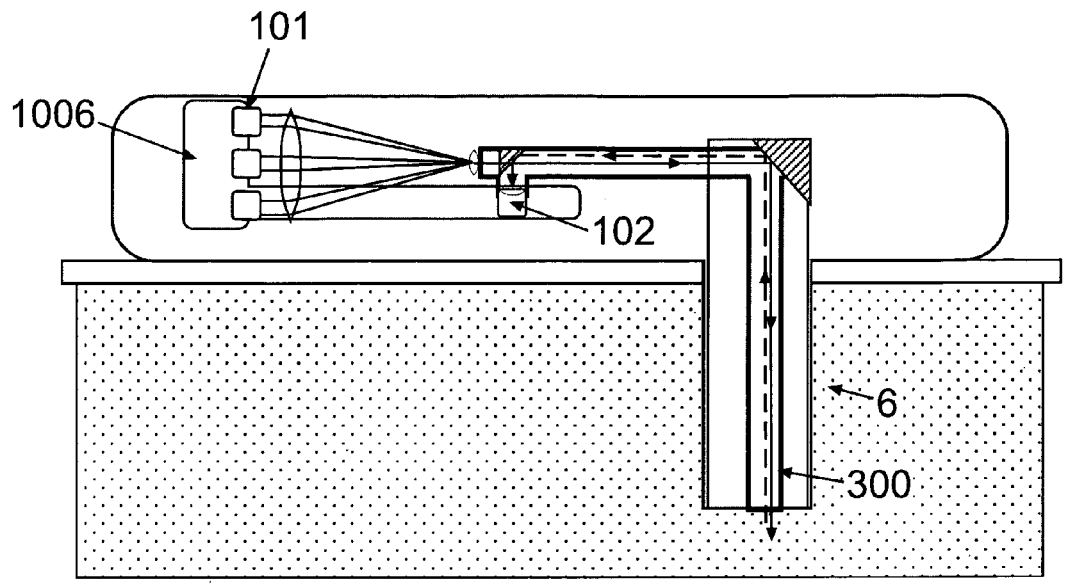
FIGS. 12a-b show the patch unit comprising one or more light sources (12a) and one or more detectors (12b).
Figure 12B:
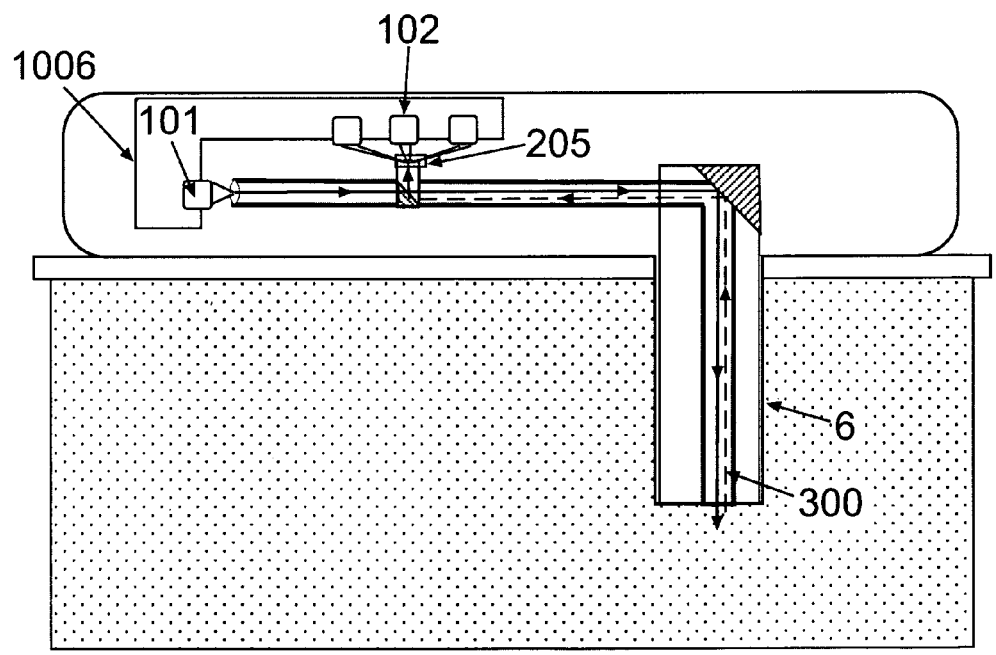

FIGS. 12a-b show an embodiment of the present invention with a plurality of light emitting sources (FIG. 12a) and a plurality of detectors (FIG. 12b), with the light (300) passing from the source (101), through the probe (6) to the body, and back to the detectors (102). FIG. 12a shows an embodiment with a plurality of light-emitting sources (101) and a single detector (102) in the monitoring apparatus (1006). Each source (101) emits light at a discrete wavelength (or a narrow range of wavelengths). FIG. 12b shows an embodiment with a single light-emitting source (101) and a plurality of detectors (102). Each detector (102) detects a discrete wavelength or spectrum of wavelengths from within the returned light (300). In one embodiment, the separation of light is in the source. In such an embodiment, the light emitting source (101) may be selected out of various types of light-emitting sources including for example, a broadband illumination source covering the entire required spectral bandwidth, a wavelength-tunable light source, or a bank or an array of discrete illumination sources where each discrete illumination source covers a portion of the required spectral band. An array of monochromatic illuminators associated with respective narrow band filters, also present a practical option for limiting the spectrum of illumination to any desired range. Separation of light may also be performed after the light-emitting source using a prism, diffraction grating, tunable filter or other separating means known in the art.

Broadband illumination sources include without limitation miniature incandescent lamps, glow bars, or halogen, Xenon, or Quartz lamps. Narrow band illumination sources include without limitation small solid state LEDs, laser diodes; electro-luminescent plastic devices, gas diodes, white light-emitting diodes (LEDs), semiconductor lasers, or vertical cavity surface emitting lasers (VESCLs). Such sources are evidently chosen according to the relevant spectral range needed for detecting analyte concentration levels. In addition, organic light-emitting diodes (OLED) and electrofluorescence material can be incorporated. Light sources are available from OSRAM Germany, NICHIA Japan and others.

In another embodiment, the separation is in the detector (102), where separator (205) is present before the detectors (102), as shown in FIG. 12b. The separator (205) includes without limitation filters, diffraction grating, or an optical prism that splits the incoming light into multiple rays of different wavelengths. The output spectrum exiting the separator (205) is received by further optical elements implemented, for example, as focusing optics that may direct the received rays onto an array of detectors, or separate single wavelength dedicated optical detectors (102). Examples of detectors include without limitation Silicone, InGaAs, PbS, PbSe, bolometric and others. Any detector operating at the spectral range needed for detecting analyte concentration levels, and that is available in the market, can be incorporated into the monitoring device. Bolometric detectors are manufactured by SCD Ltd. Israel, or SOFRADIR, France. Gratings are available from Edmund Optics, USA.

Figure 13:
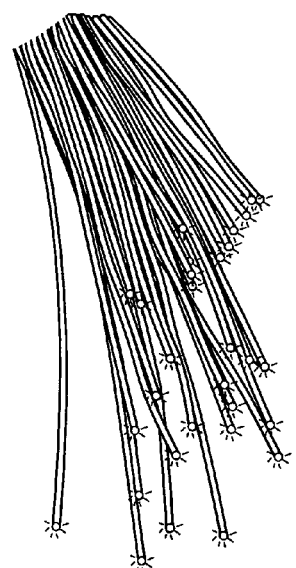
FIG. 13 shows an example of optical fibers to be used within the monitoring device.

FIG. 13 shows an example of optical fibers used in the monitoring device to pass the light to the body. Such optical fibers can include multi-mode and single-mode fibers, optical fibers with code and clad, hollow waveguides, or bundles. Optical fibers are available from Polymicro Technologies, LLC and from Fiberoptic Systems, Inc. Examples of other optical means used to direct the light can include without limitation reflectors, lenses, beam splitters, filters, prisms and other optical means known in the art.

Figure 14A:
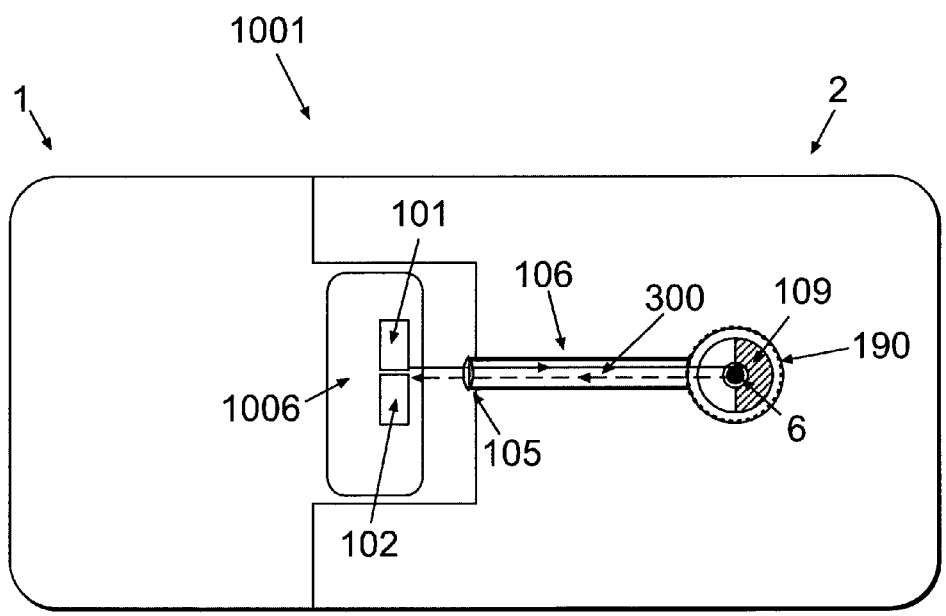
FIGS. 14a-c show a two-part patch unit. Light passes between parts through a lens.
Figure 14B:
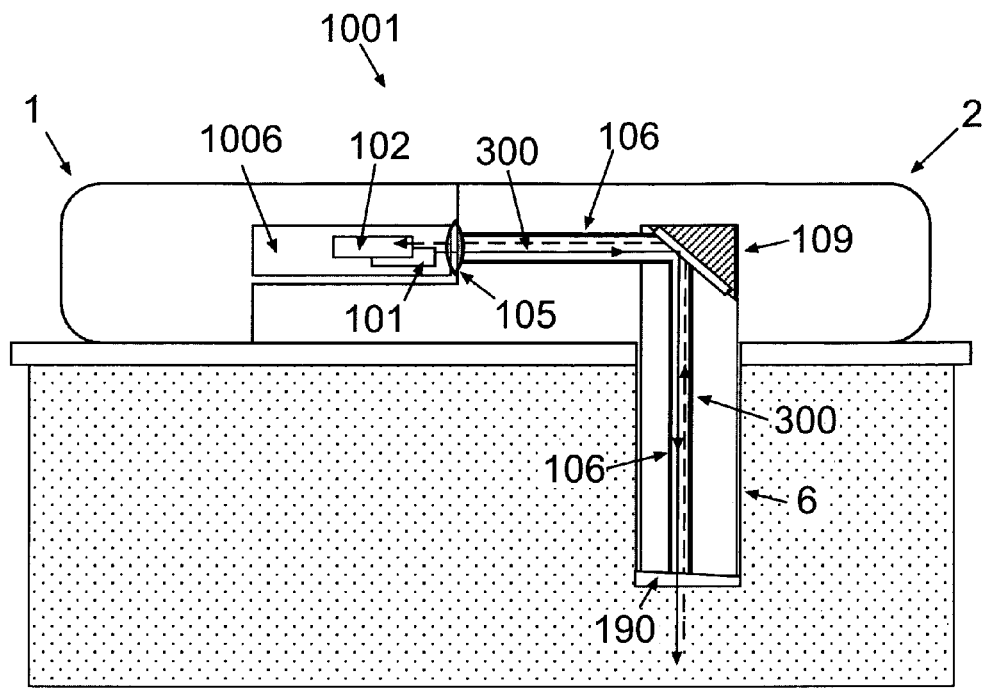
Figure 14C:
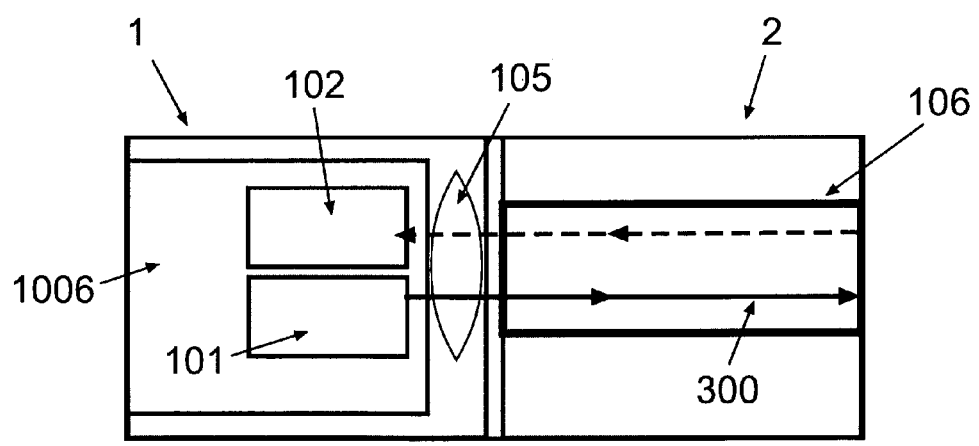

FIGS. 14a-c show an embodiment of the two-part patch unit (1001) having at least one lens (105), used for passing the light (300) between the light-emitting source (101) and detector (102), located in the reusable part (1) and the optical fiber (106) located in the disposable part (2). The disposable part (2) is connected to the probe (6). The light (300) is emitted from the source (101) through an optical fiber (106) which terminates in a lens (105). The lens (105) is located at the interface between the reusable part (1) and disposable part (2). The lens (105) directs the light (300) towards optical system (109), which transmits the light (300) into an optical fiber (106) and into the body. The returned light (300) passes from the disposable part (2), through the optical fiber (106) and through the optical system (109), to the lens (105), and back to the detector (102) in the reusable part (1). FIG. 14a and FIG. 14b show a side-view and a top-view, respectively, of the patch unit (1001) with the lens (105) between the reusable part (1) and the disposable part (2). FIG. 14c shows an enlargement of the interface between the reusable part (1) and the disposable part (2) and the passage of light (300) between the two parts via the lens (105).

In one embodiment, the optical lens (105) serves as collimating means, or focusing means, for narrowing down the scattering of the emitted and returning light. Examples of lens materials include without limitation IR transmitting plastic, glass, and crystal. While use of plastic lens may be more cost-effective, glass and crystal lenses have superior optical properties. In another embodiment, an optical coupler (not shown) is present between the reusable part (1) and disposable part (2), where the optical coupler may be a window inclined by an 8 degree angle.

Figure 15A:
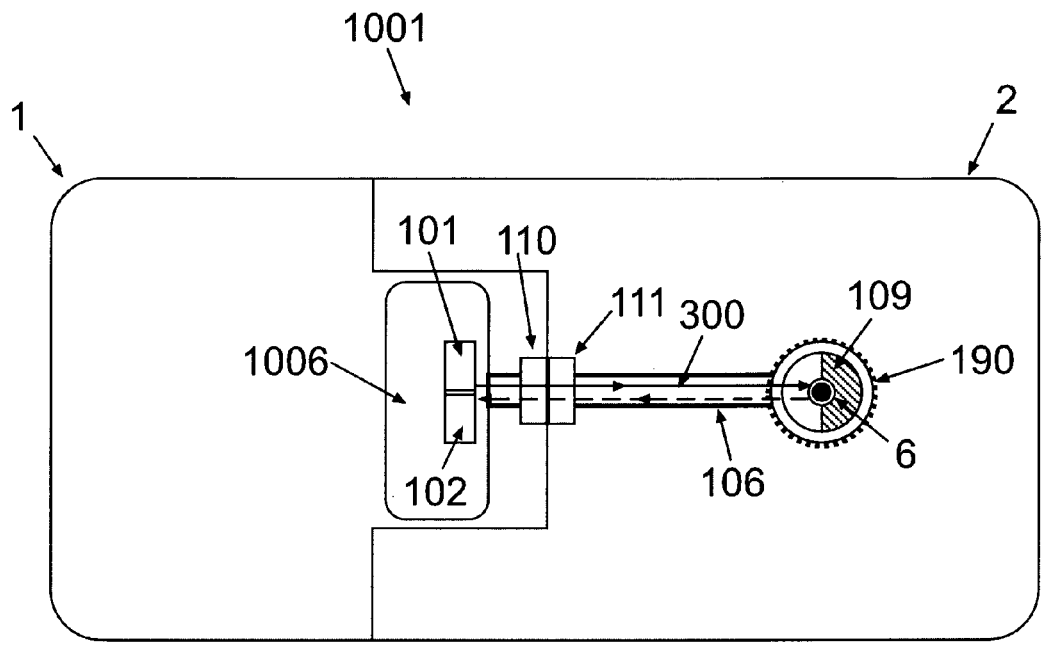
FIG. 15a-c show a two-part patch unit, and the transfer of light from the reusable part to the disposable part of the patch unit through two optical windows.
Figure 15B:
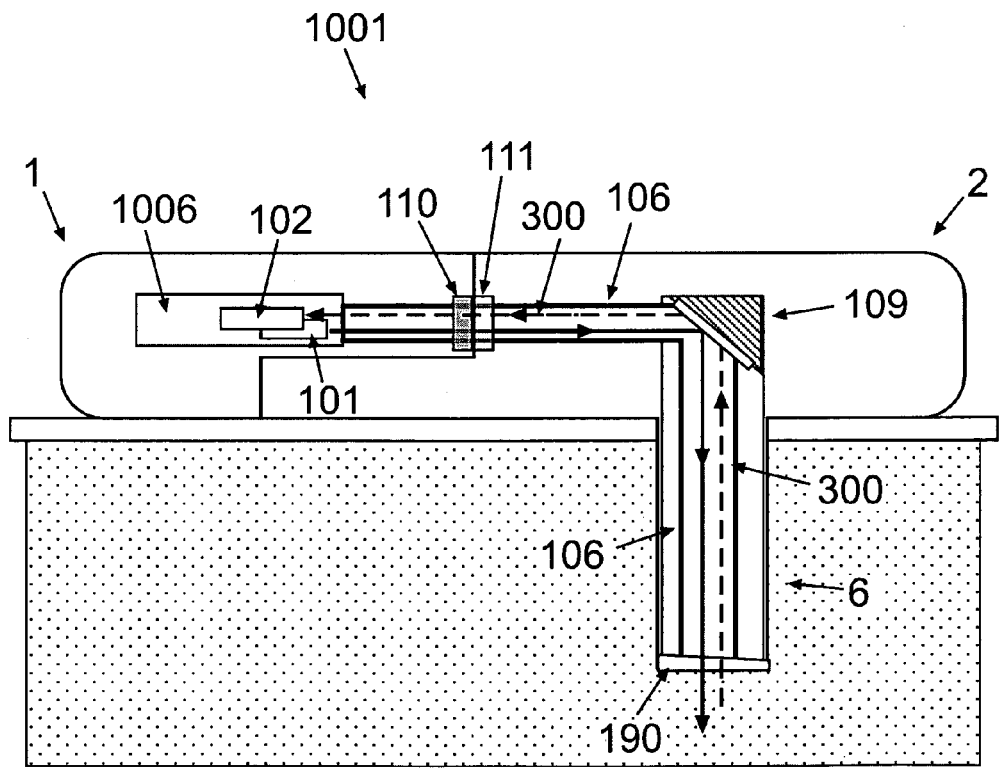
Figure 15C:
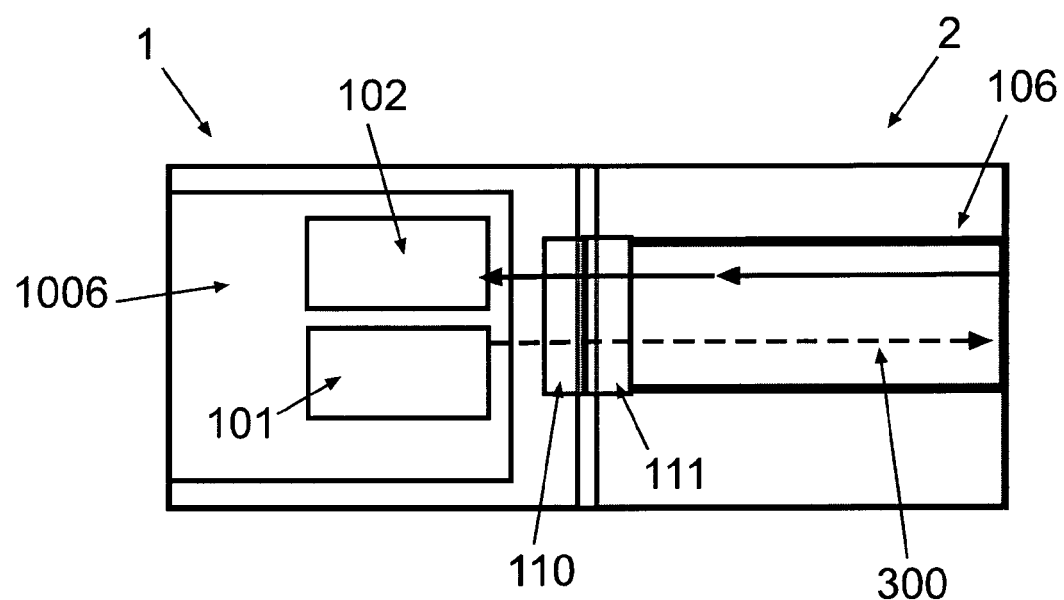

FIGS. 15a-c show another embodiment of the two-part patch unit (1001), having two optical windows (110) and (111) located in the reusable part (1) and the disposable part (2), respectively, and enabling the passage of light between the reusable part (1) and the disposable part (2). The source (101) and detector (102) reside in the reusable part (1). The light (300) passes from the source (101), through the optical window (110) in the reusable part (1), to the optical window (111) in the disposable part (2). The light (300) encounters optical system (109), which transmits the light via an optical fiber (106) through the probe (6) to the body. The returned light passes back from the body, to the disposable part (2), via the optical system (109), passes through the optical windows (110, 111) and to the detector (102), in the reusable part (1).

FIG. 15a and FIG. 15b show a top-view and a side-view, respectively, of the patch unit (1001) with the two optical windows (110) and (111) in the reusable part (1) and the disposable part (2), respectively. FIG. 15c shows an enlargement of the interface between the reusable part (1) and the disposable part (2) and the passage of light (300) between the two parts (1, 2), via the two optical windows (110, 111). In one embodiment, the two optical windows (110, 111) do not absorb light in the wavelengths relevant for detecting analyte concentration levels, and may be made of plastic, glass, crystal, or any other suitable material known by those having ordinary skill in the art. In one embodiment, the optical windows (110, 111) serve as focusing means for narrowing down the scattering of the emitted and returning light. In one embodiment, an optical coupler (not shown) is positioned between the reusable part (1) and disposable part (2), where the optical coupler may be a window inclined at an angle, including without limitation, 8 degrees. Alternatively, the two optical windows (110, 111) may be, both or separately, inclined at an angle, including without limitation, 8 degrees.

Figure 16:
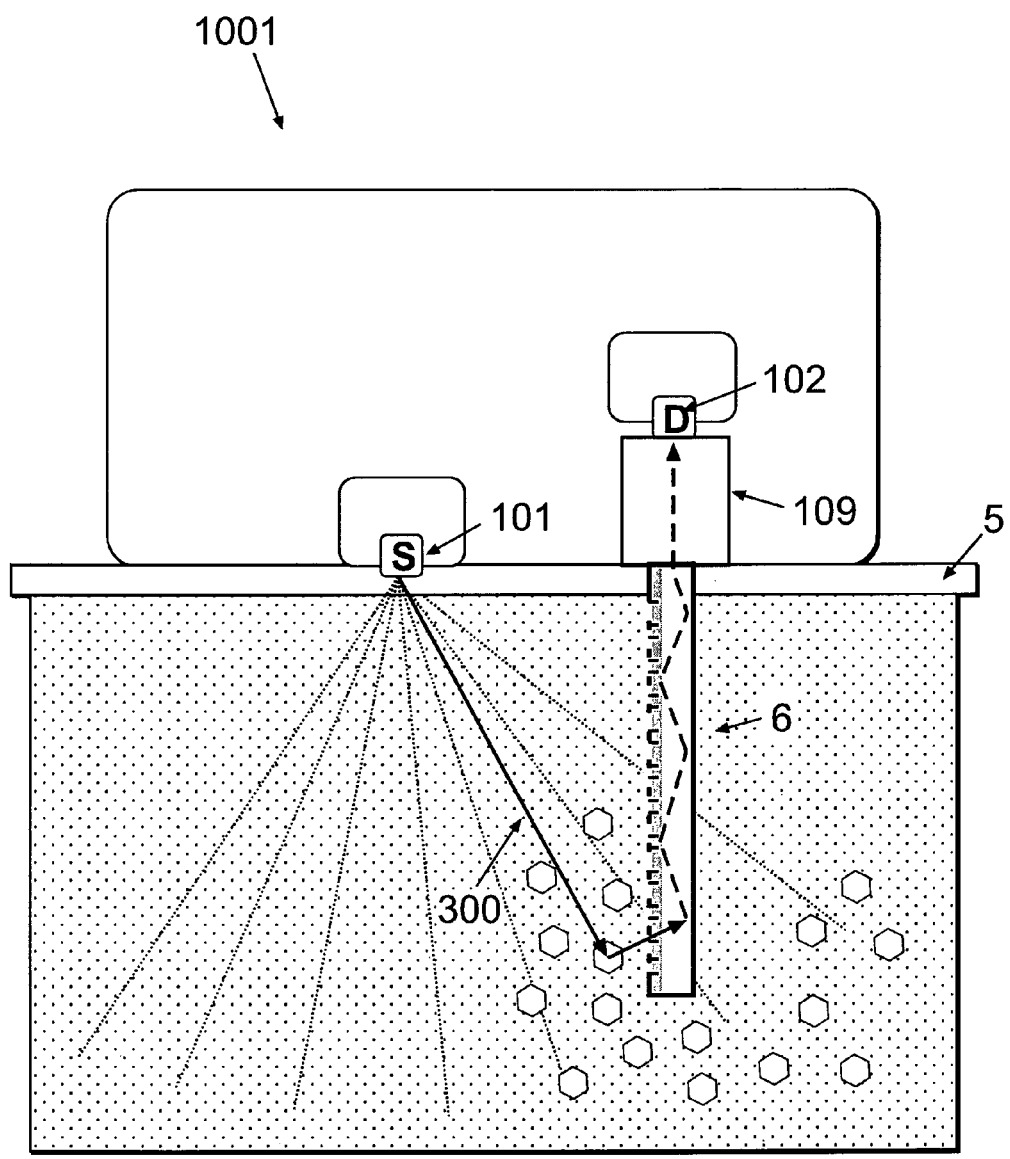
FIG. 16 shows the monitoring device, in which the light-emitting source emits light directly from the patch unit through the skin.
Figure 17:
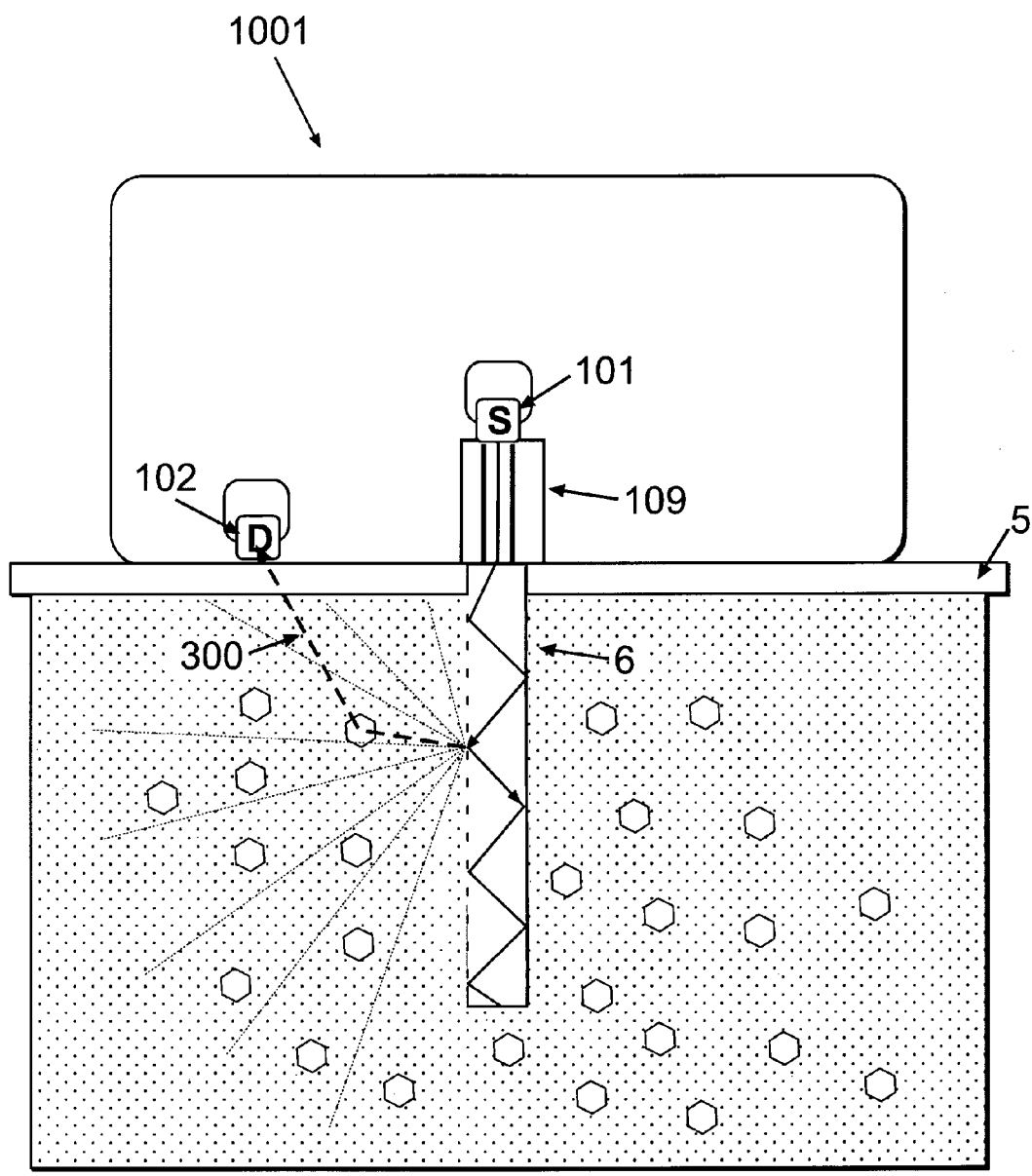
FIG. 17 shows the monitoring device in which the detector detects light that was emitted directly from the body.

FIG. 16 shows an embodiment of the patch unit (1001), in which the source (101) emits light (300) directly onto the skin (5) and into the body. The light (300) passes through the analyte-containing ISF and reaches the probe (6), residing inside the body. After light interactions in the ISF, some of the light (300) enters the probe (6), through which the light (300) is transmitted via an optical system (109) to a detector (102) in the patch unit (1001). FIG. 17 shows an embodiment of the patch unit (1001) in which at least one detector (102) detects light (300) that passes directly through the skin (5). Light (300) emitted from the source (101), passes through the optical system (109) through the probe (6) to the body. The light (300) is emitted to the analyte-containing ISF. After light-tissue interactions in the ISF, the light (300) is detected through the skin (5) by at least one detector (102) in the patch unit (1001).

Figure 18A:
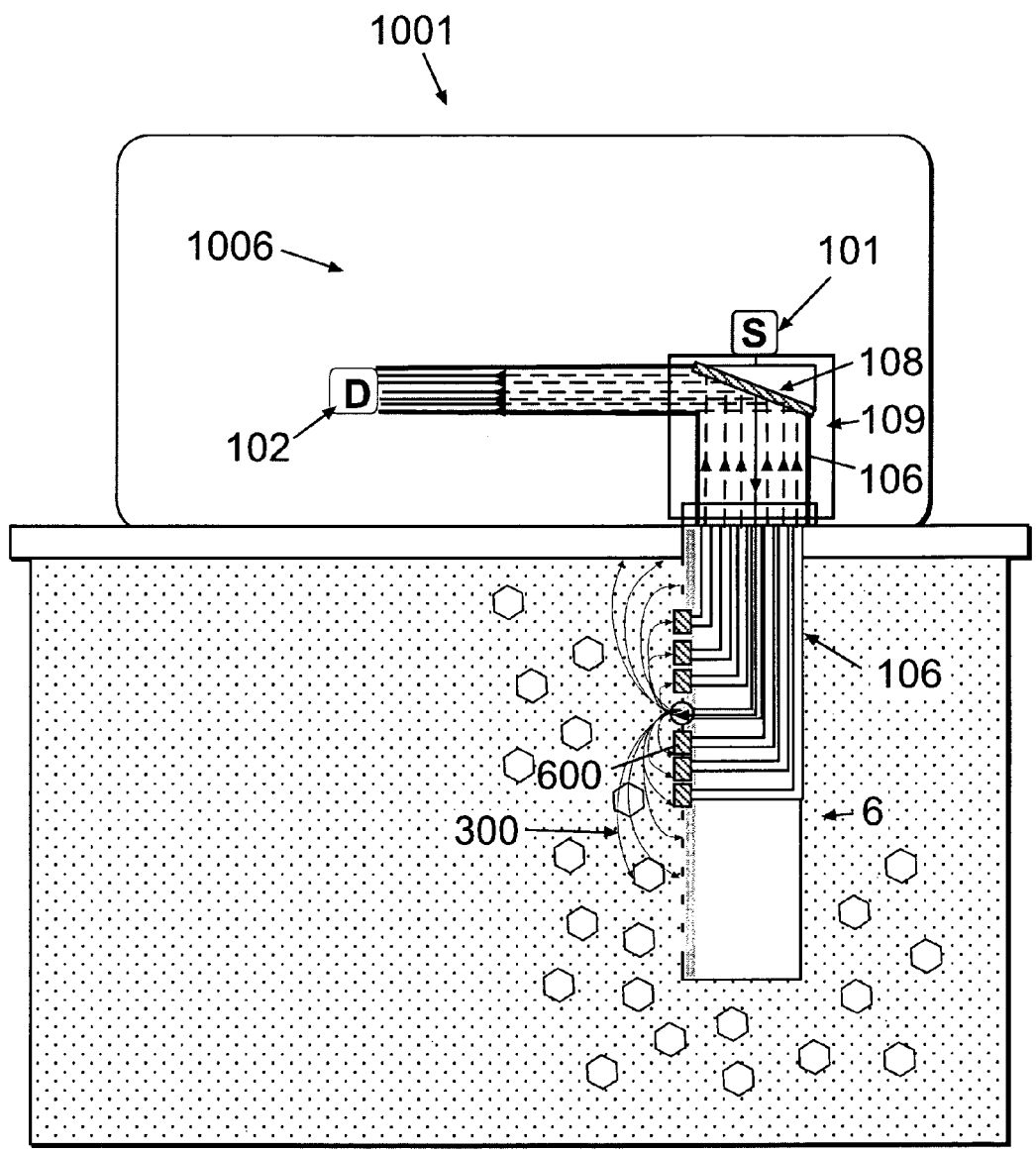
FIGS. 18a-b shows the monitoring device, in which the light passes between the probe and the ISF in a banana-shaped photon trajectory.
Figure 18B:
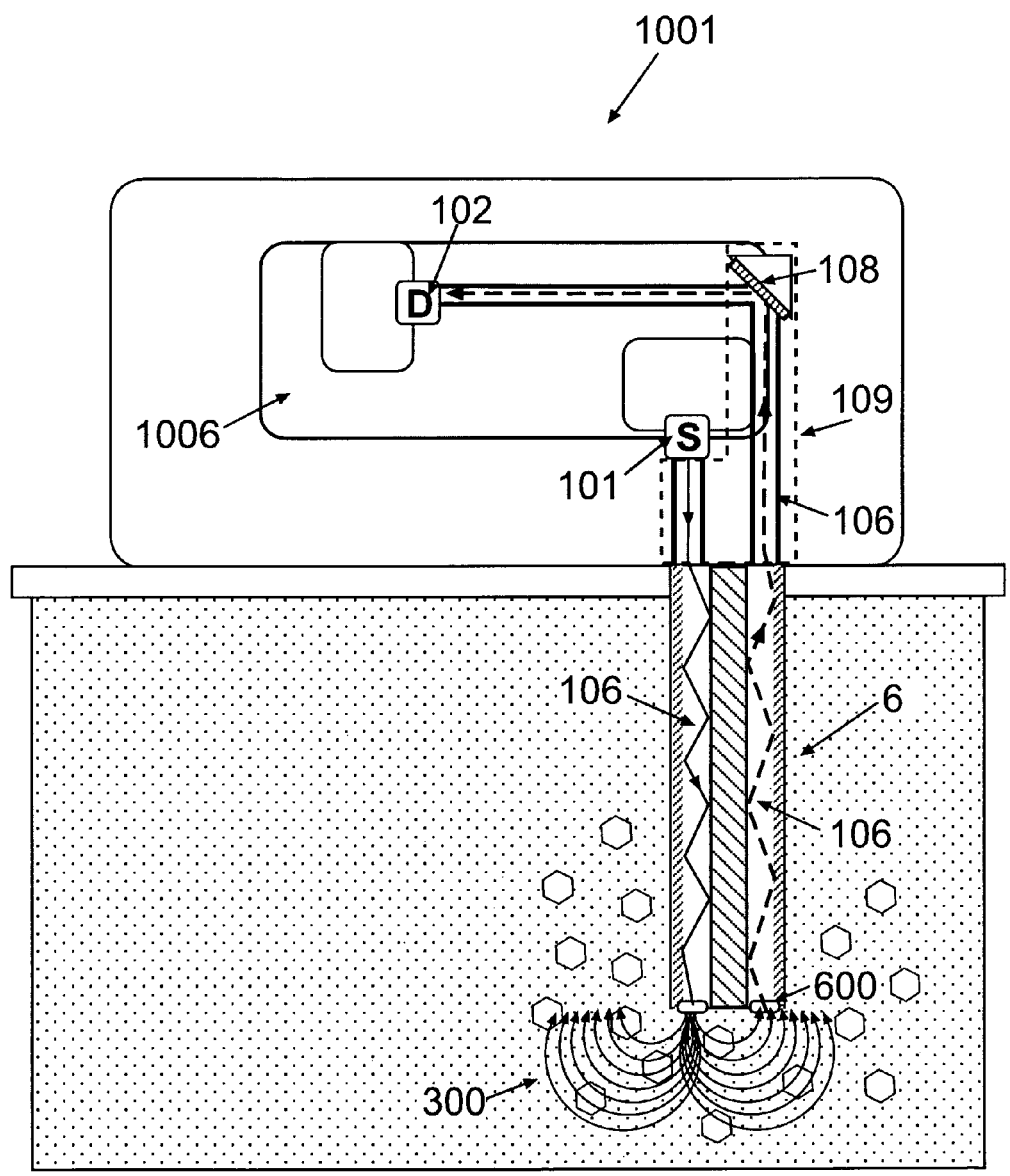

FIGS. 18a-b show embodiments in which the light (300) passes between the probe (6) and the ISF in a banana-shaped photon trajectory. In these embodiments, light (300) is emitted from the source (101) in the monitoring apparatus (1006) in the patch unit (1001) through an optical system (109), which may include optical fibers (106), reflectors (108) or other optical means, and through the probe (6) to the body. FIG. 18a shows an embodiment in which the light (300) is transmitted to the ISF through openings (600) in the optical fibers (106), located laterally on the probe (6). The light (300) is transmitted through the ISF in a banana-shaped photon trajectory so that some of the light (300), after passing through analyte-containing ISF, enters back into the lateral openings (600) in the optical fibers (106) in the probe (6). Since the probe (6) is circular, light (300) is emitted towards all sides of the ISF surrounding the probe (6). In one embodiment, a clad is removed from the optical fibers (106) located in the probe (6), at several discrete locations along the fiber (106), such that light (300) exits the optical fibers (106) from the cladless locations (600) and is transmitted to the surrounding ISF. Some of the light (300) is captured by the clad-less fibers (106), and returned through the optical fiber (106) to the detector (102). FIG. 18b shows an embodiment in which the light (300) is transmitted to the ISF through openings (600) in the optical fibers (106), located at the bottom of the probe (6). The light (300) is transmitted through the ISF in a banana-shaped photon trajectory so that some of the light (300), after passing through analyte-containing ISF, enters back into the openings (600) in the optical fibers (106) in the bottom of the probe (6). The optical fibers (106) transmit the returned light (300) back up towards the detector (102) in the monitoring apparatus (1006).

FIGS. 19-27 show embodiments of various configurations of the optical fibers (106) used to pass the light (300) from the monitoring apparatus (1006) to the body, and of the location of the optical fibers (106) within the probe (6). The configurations of the optical fibers (106) affect the way the probe is inserted into the body. In one embodiment, the optical fibers (106) transmit light (300) in one direction, such that some of the optical fibers (106) transmit light (300) from the light emitting source (101) to the body, and some of the optical fibers transmit light (300) from the body towards the detector (102). In another embodiment, the optical fibers (106) are both Source fibers (S) and Detector fibers (D) (marked as "S/D"), which transmit light (300) in both directions—from the light emitting source (101) to the body and from the body towards the detector (102).

Figure 19A:
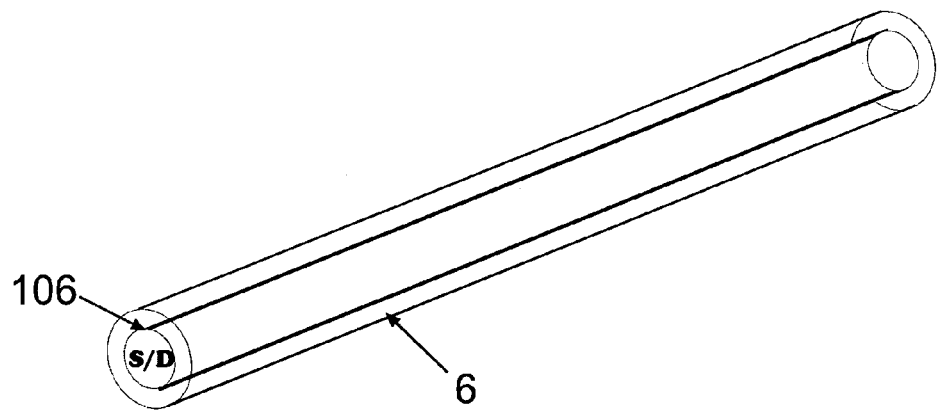
FIGS. 19a-b show the monitoring device, in which the probe is a hollow optical fiber.
Figure 19B:
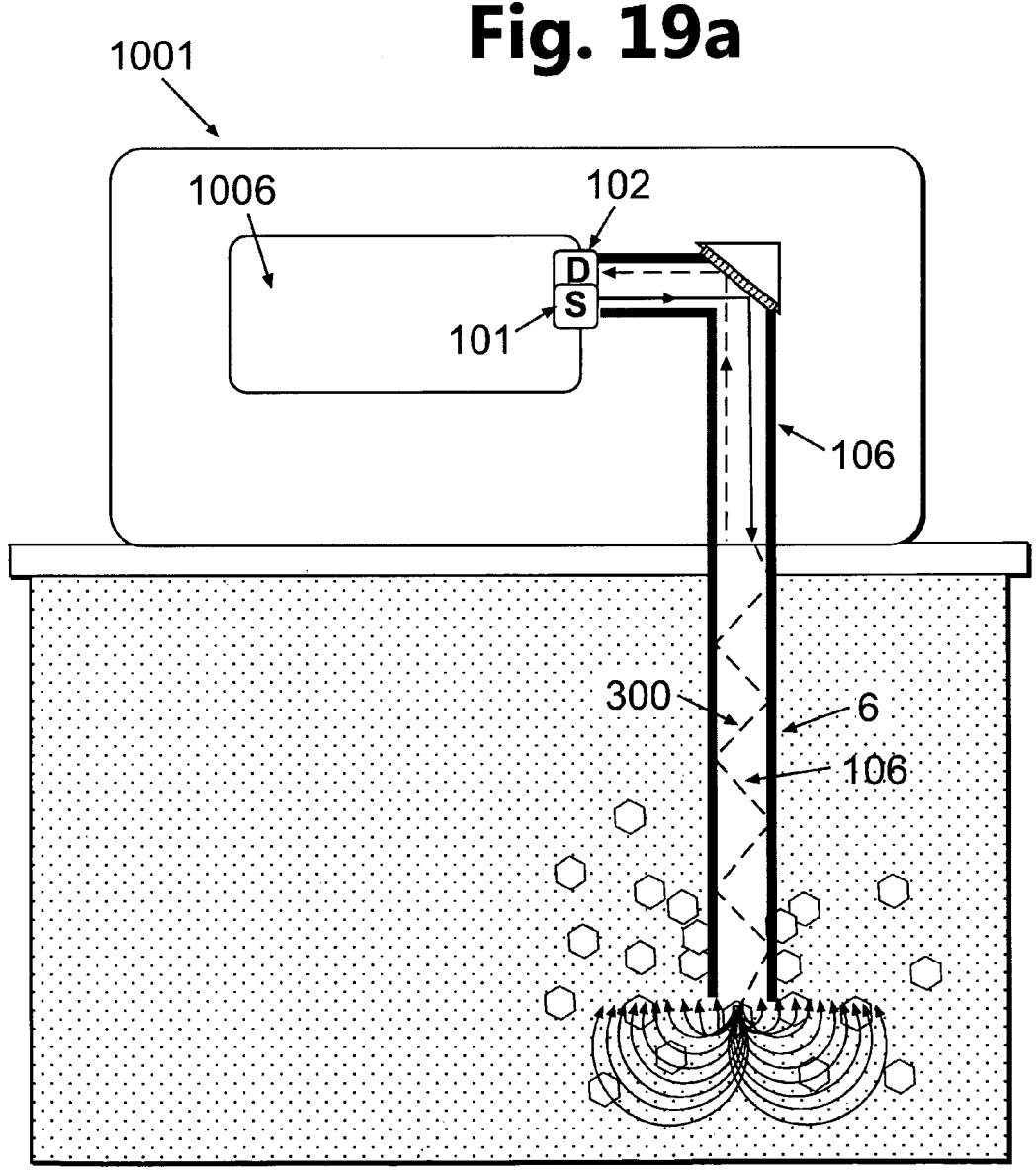

FIG. 19 shows an embodiment in which the probe (6) is a hollow optical fiber (106) able to transmit light (300) in both directions—from the light emitting source (101) to the body and from the body towards the detector (102) in the monitoring apparatus (1006). FIG. 19a shows the hollow optical fiber (106) inside the probe (6). FIG. 19b shows the probe (6) with the hollow optical fiber (106), as part of the monitoring unit (1001).

Figure 20A:
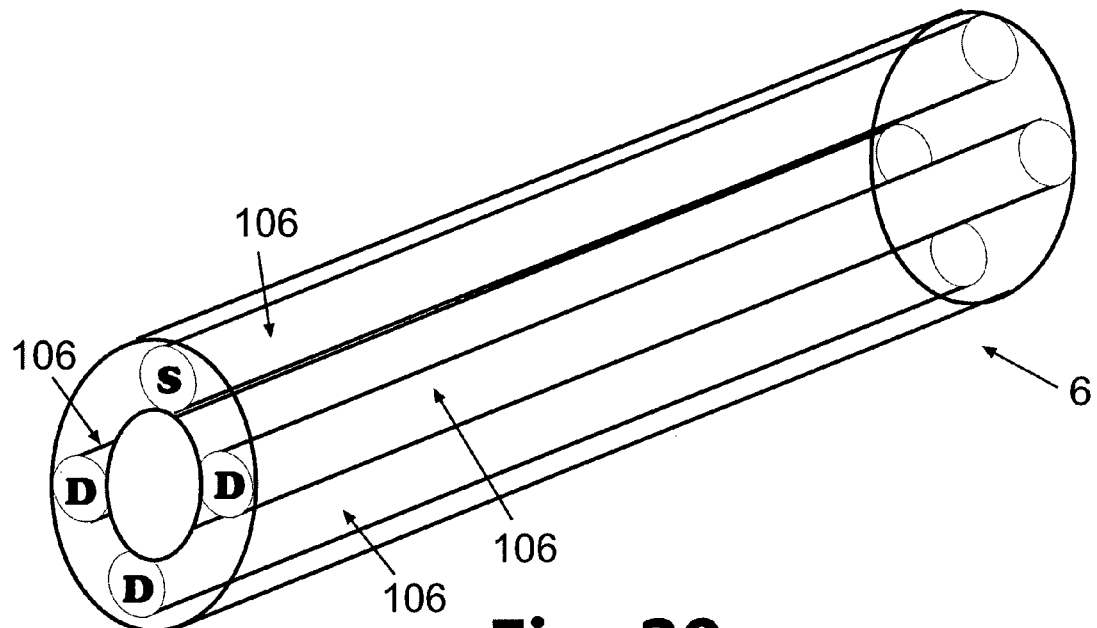
FIGS. 20a-e show the monitoring device, in which the probe comprises of a plurality of optical fibers inserted in its lateral walls.
Figure 20B:
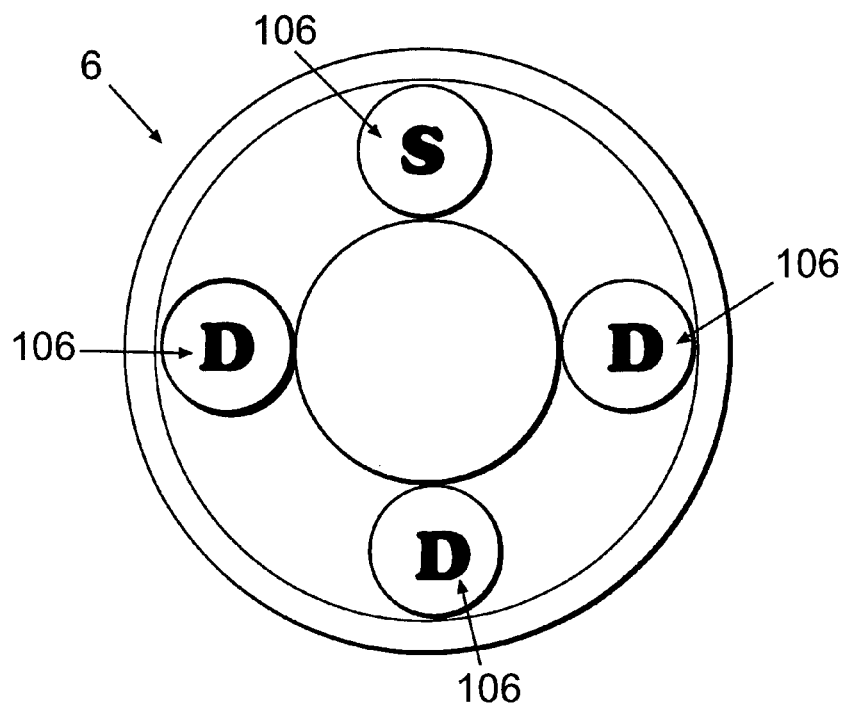
Figure 20C:
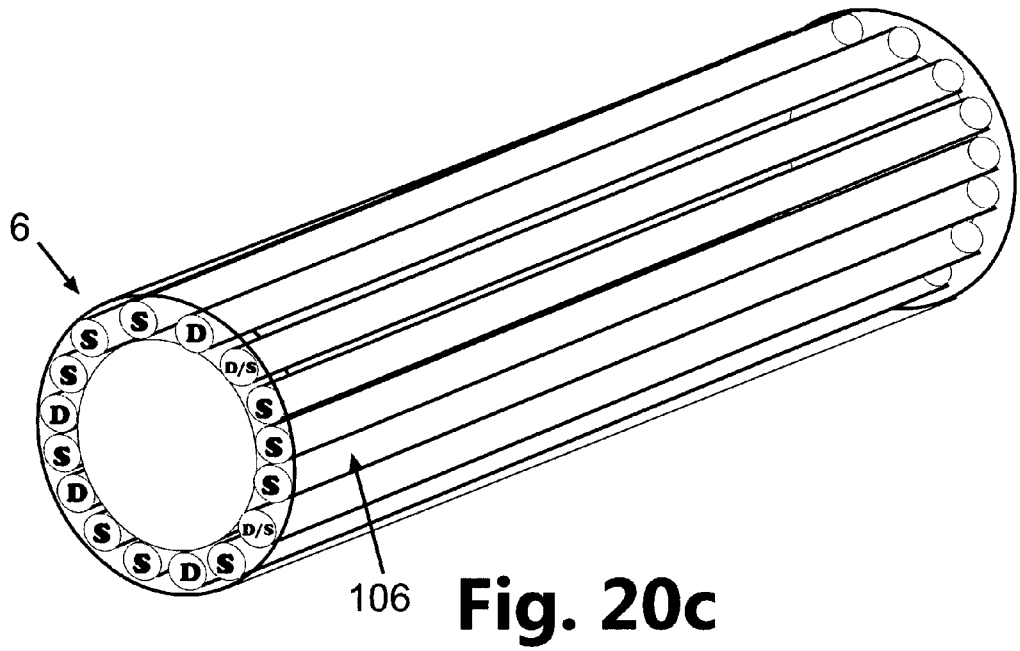
Figure 20D:
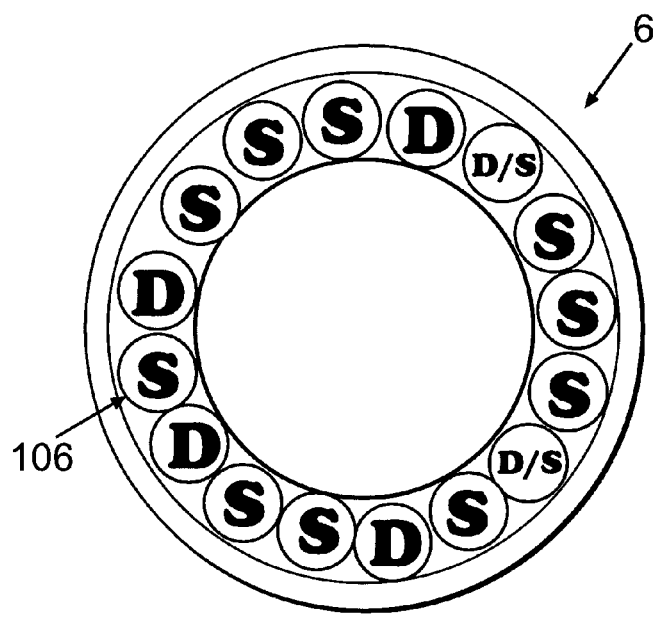

FIG. 20 shows an embodiment in which the probe (6) comprises a plurality of optical fibers (106) that are inserted in the lateral walls of the probe (6). In one embodiment, the optical fibers (106) transmit light (300) in both directions—from the light emitting source (101) to the body and from the body towards the detector (102). In an alternative embodiment, some of the optical fibers (106) within the probe are Source fibers (S) and some are Detector fibers (D). FIGS. 20a-b show the probe (6) with a plurality of optical fibers (106) arranged spaciously within the probe (6), shown in full view (FIG. 20a) and cross-section (FIG. 20b). FIGS. 20c-d show the probe (6) with a plurality of optical fibers (106)

arranged in a ring located along the walls of the probe (6), shown in perspective view (FIG. 20c) and cross-section (FIG. 20d).

Figure 20E:
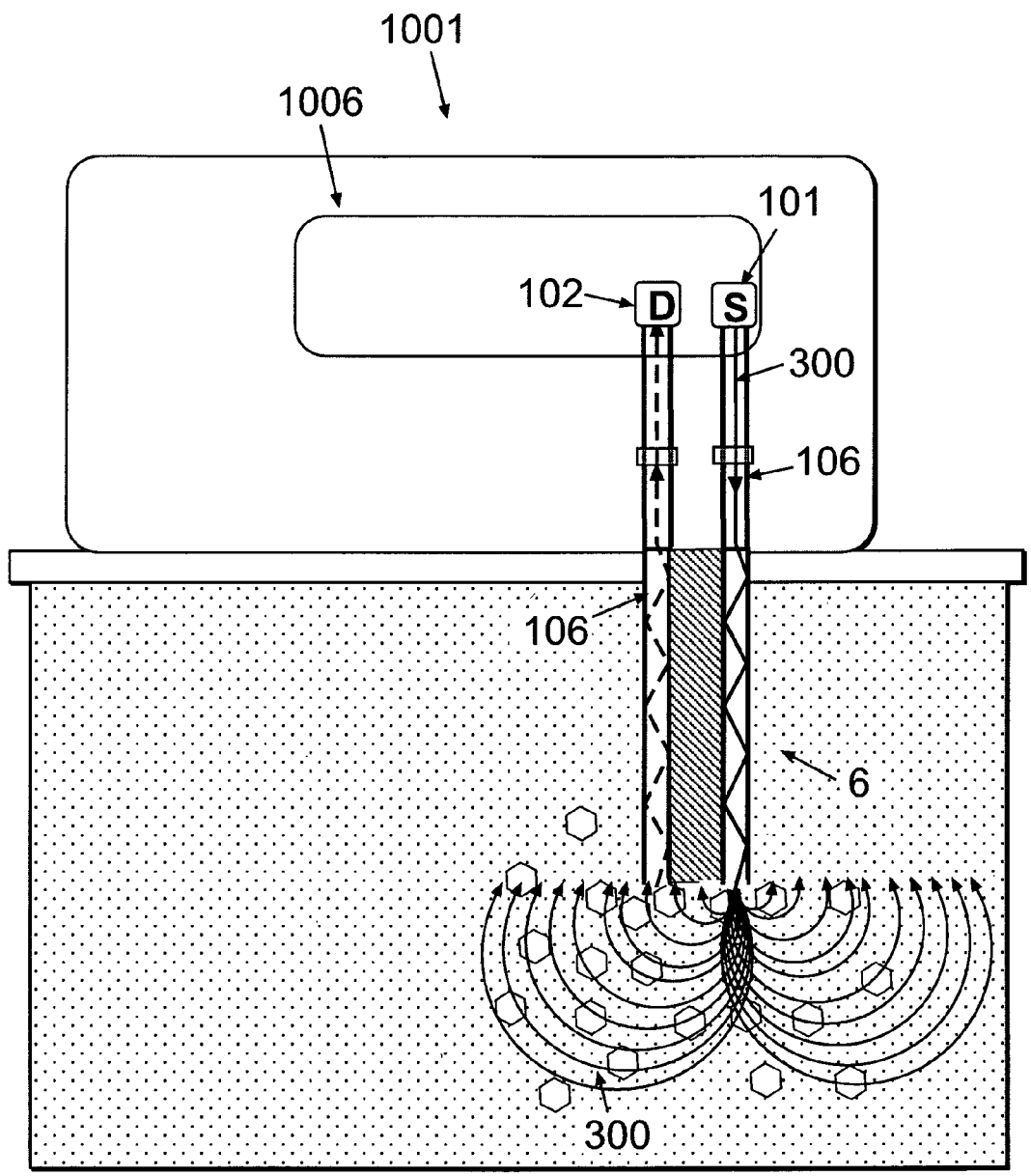

FIG. 20e shows the patch unit (1001) containing a probe (6), a plurality of optical fibers (106), a source (101) and a detector (102). In this embodiment, the penetrating member (not shown) used to insert the probe (6) into the body resides inside probe (6).

Figure 21A:
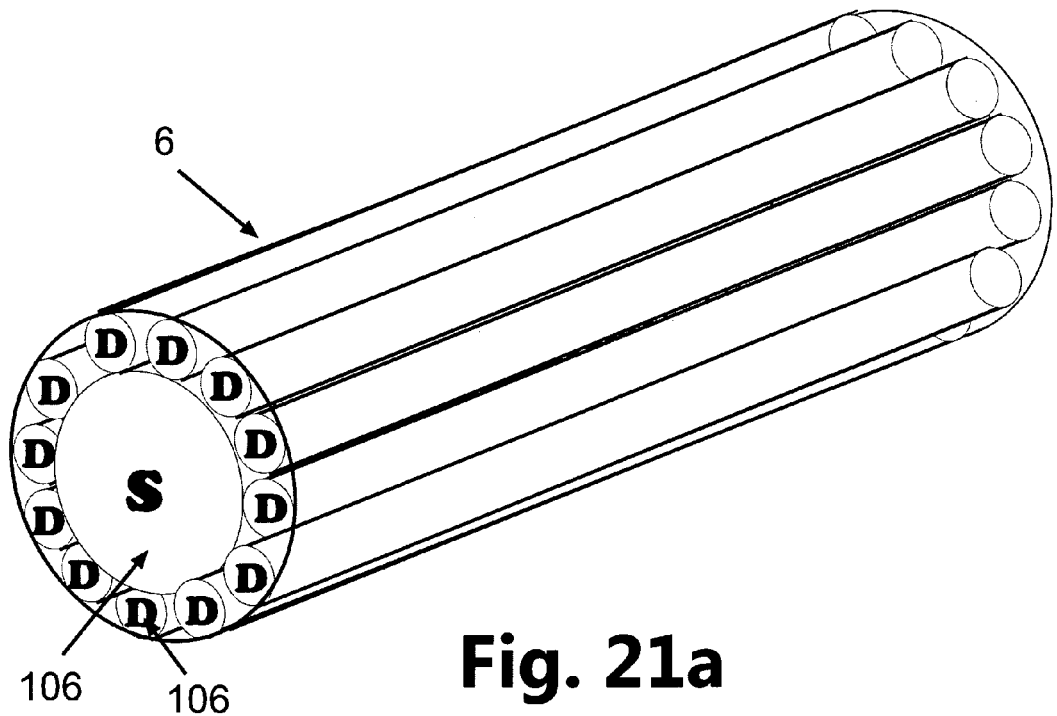
FIGS. 21a-c show the monitoring device, in which the probe comprises a plurality of optical fibers inserted in its lateral walls and one optical fiber is inserted in the center of the probe.
Figure 21B:
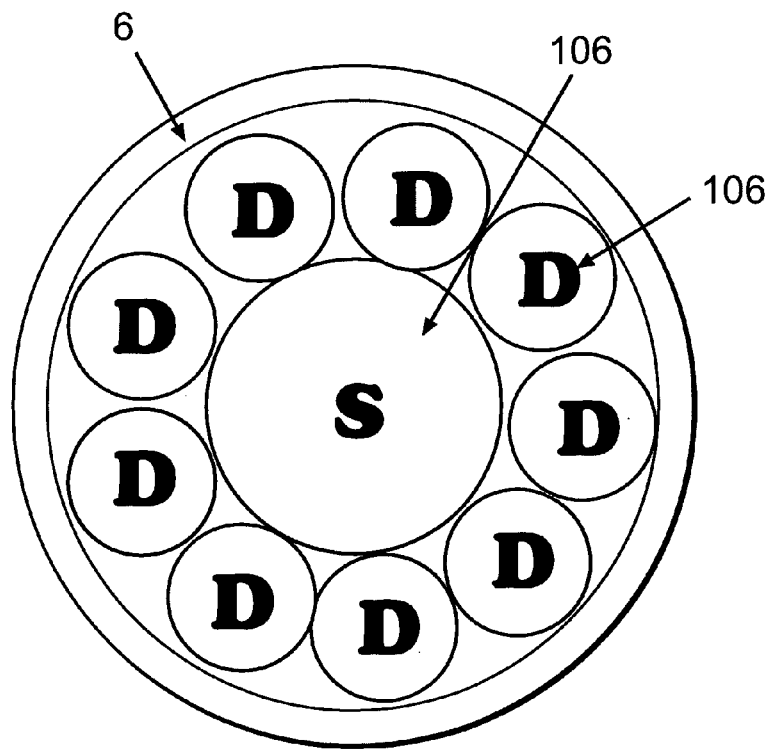
Figure 21C:
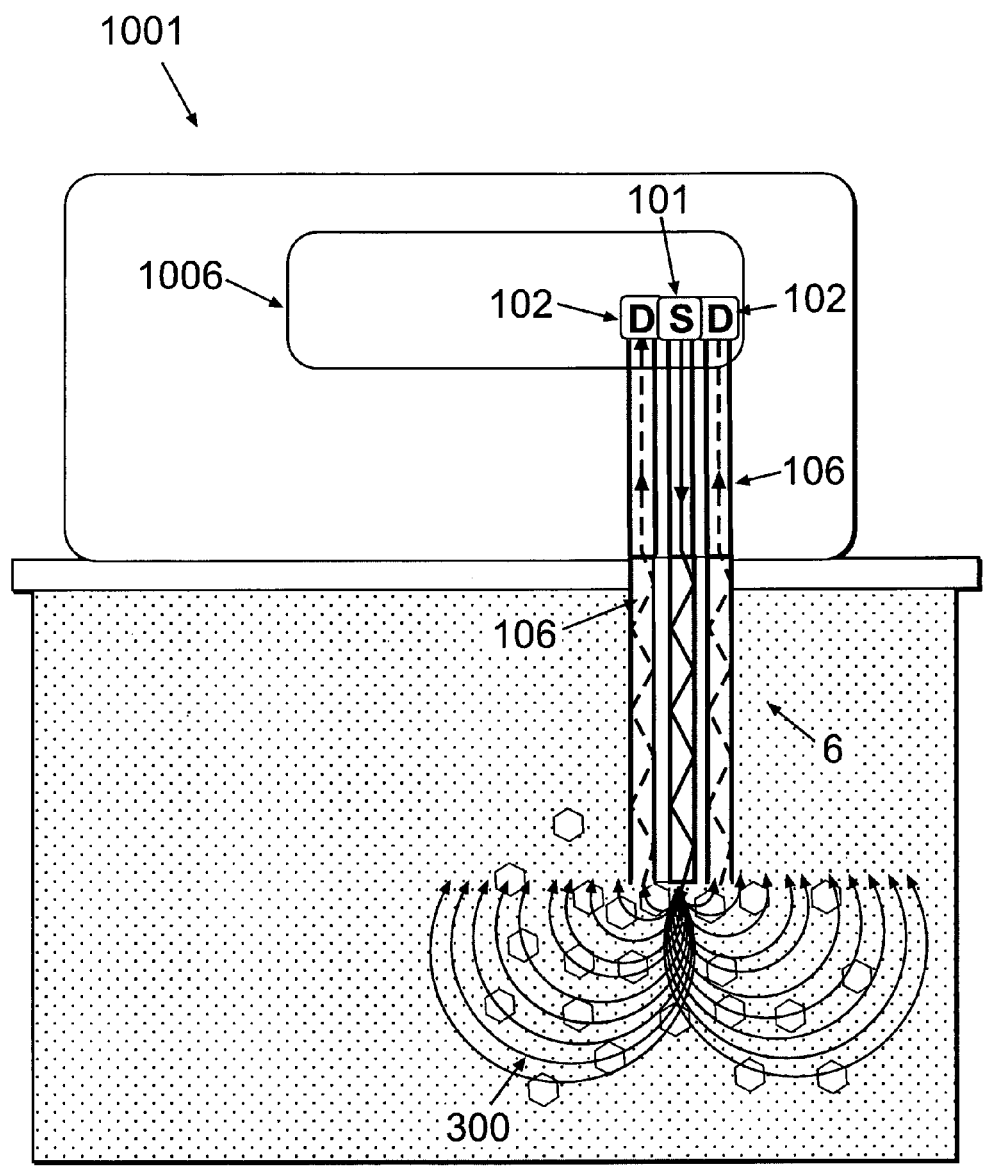
Figure 22A:
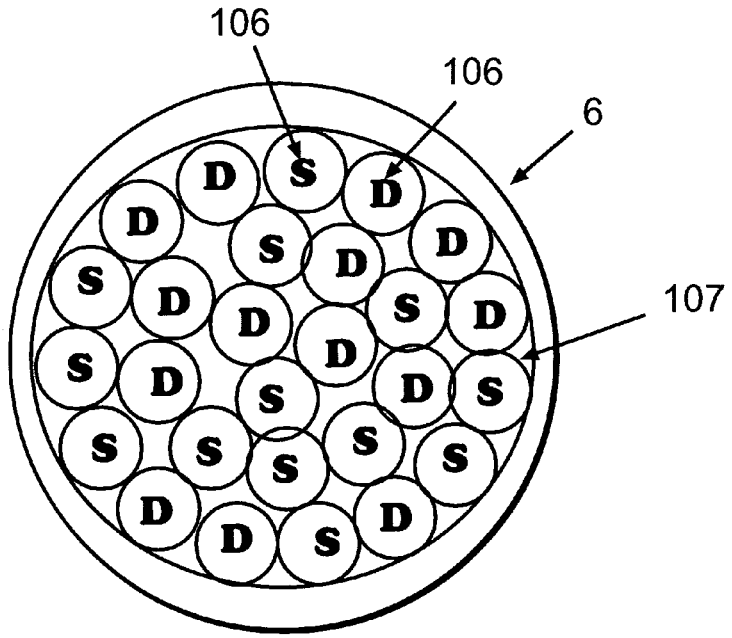
FIGS. 22a-d show the monitoring device, in which the probe comprises an optical fiber bundle.
Figure 22B:
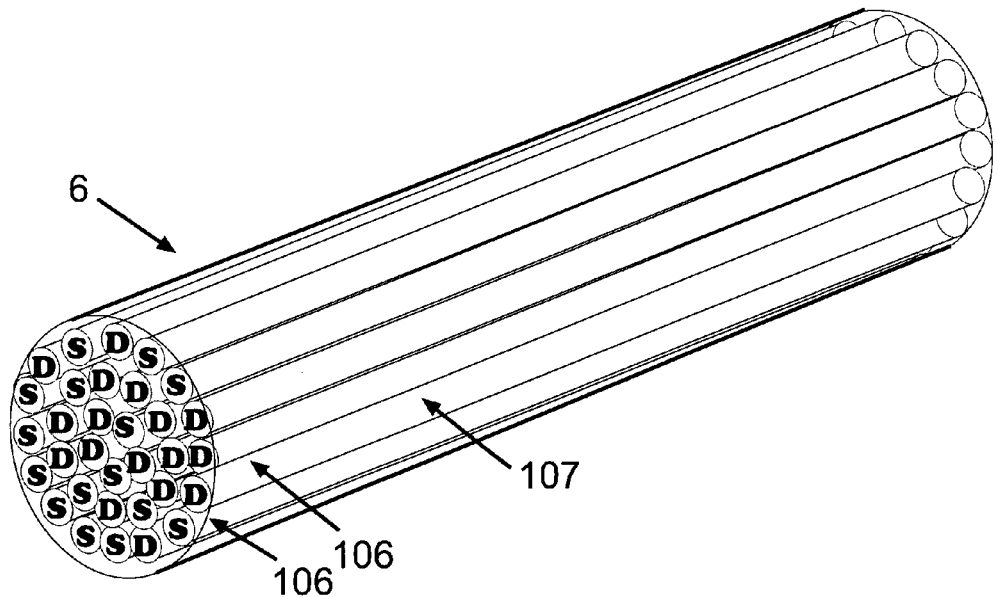
Figure 22C:
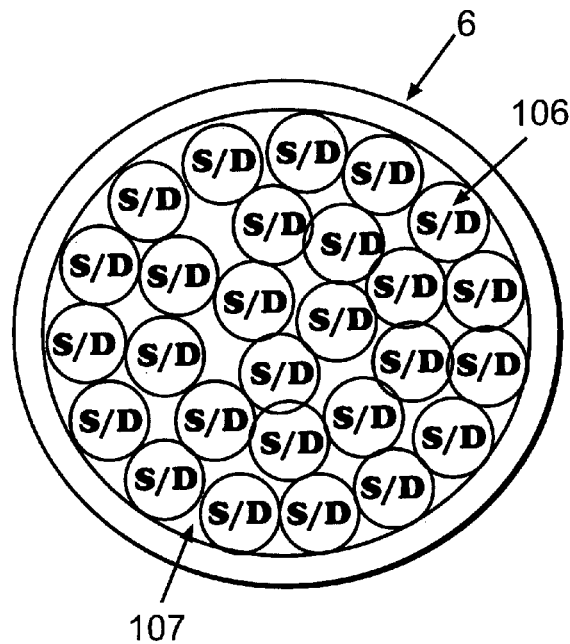
Figure 22D:
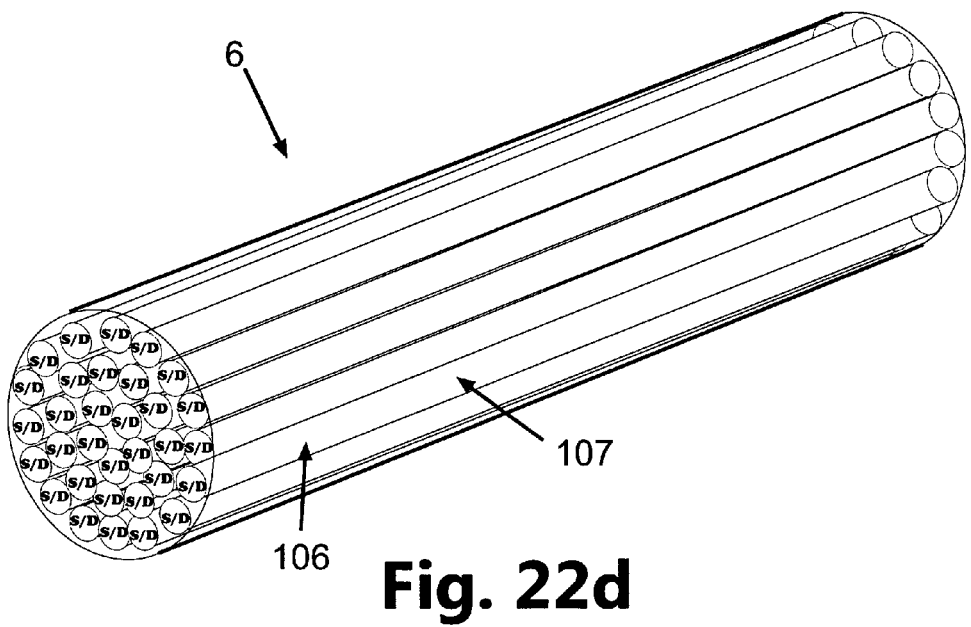
Figure 23A:
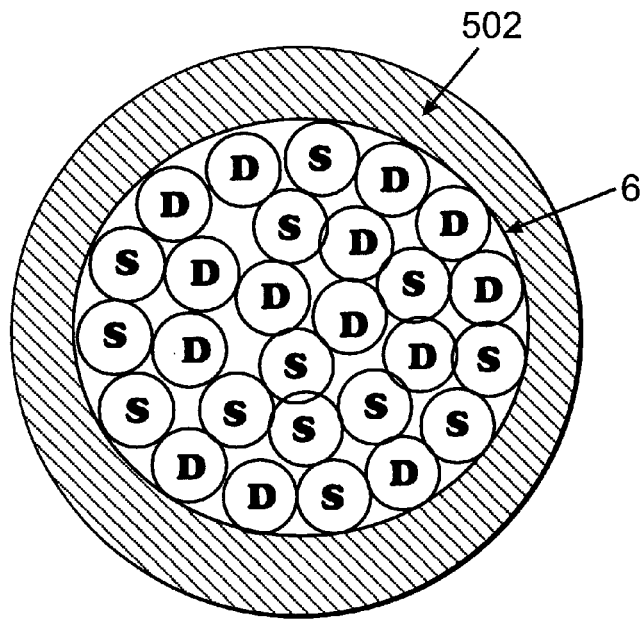
FIGS. 23a-d show means for probe insertion using a wide lumen penetrating member.
Figure 23B:
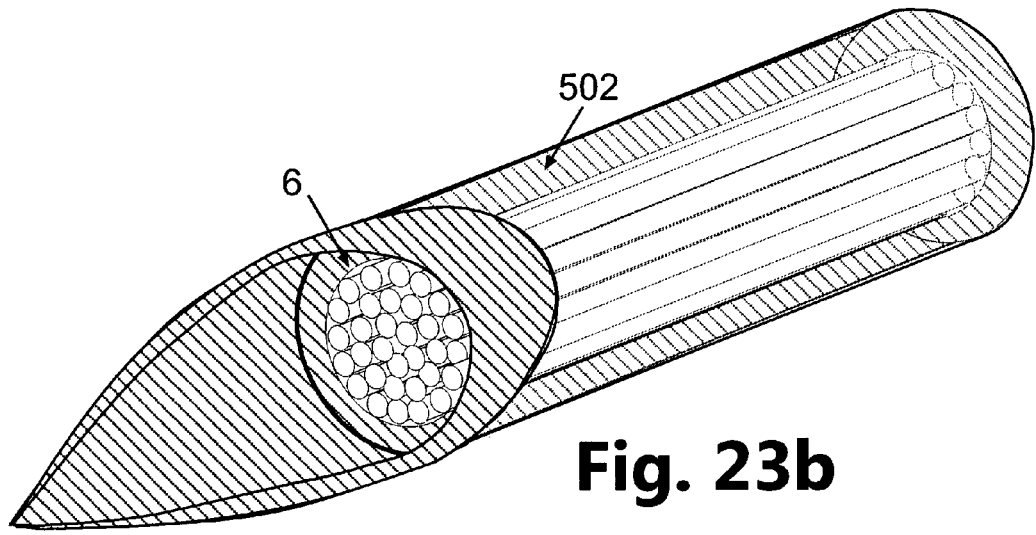
Figure 23C:
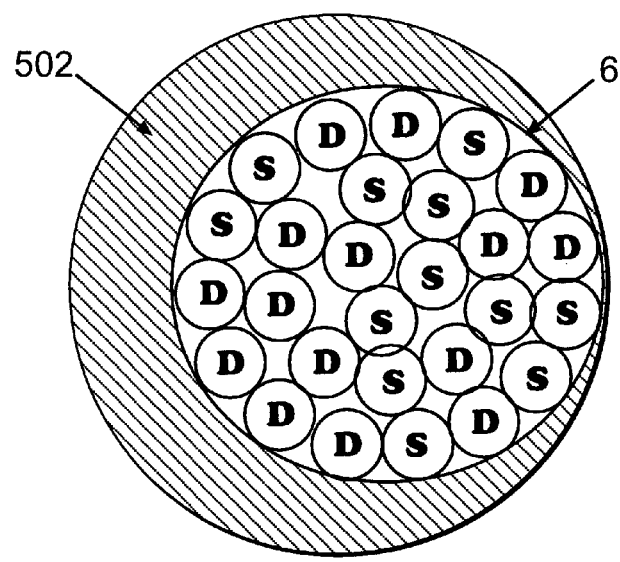
Figure 23D:
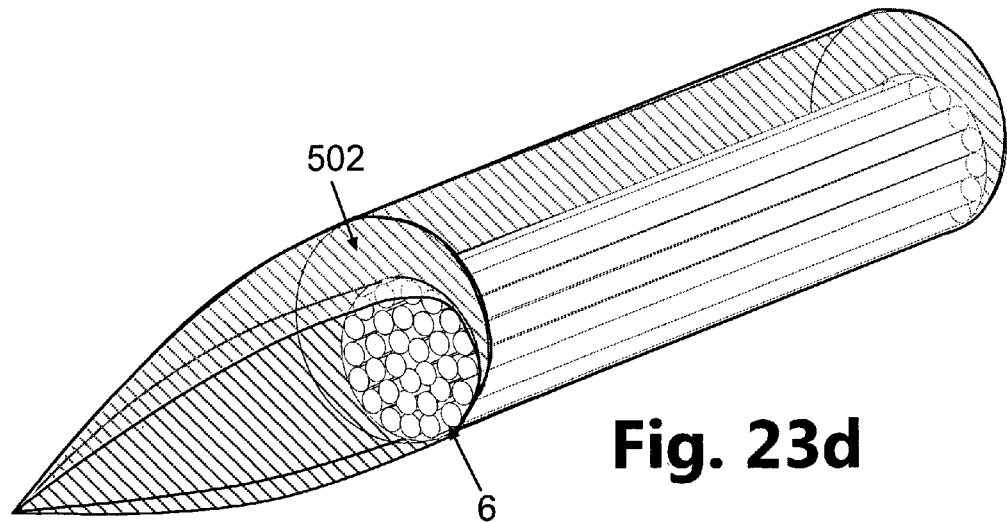

FIG. 21 shows an embodiment in which the probe (6) comprises a plurality of optical fibers (106) inserted in the lateral walls of the probe (6) and extending therealong, and one optical fiber (106) inserted at the center of the probe (6) and extending therealong. In one embodiment, the center optical fiber is the Source fiber (S) and the optical fibers on the lateral walls of the probe (6) are Detector fibers (D), such that the Detector fibers (D) surround the Source fiber (S). Alternatively, the center optical fiber is the Detector fiber (D) and the optical fibers on the lateral walls of the probe (6) are Source fibers (S), such that the Source fibers (S) surround the Detector fiber (D). In another embodiment, the center optical fiber and the lateral optical fibers (106) can be Source fibers (S) and/or Detector fibers (D). FIGS. 21a-b show the probe (6) with a plurality of optical fibers (106) arranged in a ring located along the walls of the probe (6), with a center optical fiber, shown in perspective view (FIG. 21a) and cross-section view (FIG. 21b). In this embodiment, the penetrating member (not shown) used to insert the probe (6) into the body is inside the center optical fiber. FIG. 21c shows the patch unit (1001) having a probe (6), a source (101), and at least one detector (102).

FIG. 22 shows an embodiment in which the probe (6) comprises an optical fiber bundle (107), which comprises a plurality of optical fibers (106) arranged together into one bundle. In one embodiment, some of the optical fibers within the bundle (107) are Source fibers (S) and others are Detector fibers (D), shown in cross-sectional view (FIG. 22a) and perspective view (FIG. 22b). In another embodiment, all optical fibers (106) within the optical fiber bundle (107) are able to transmit light in both directions, acting as Source fibers (S) and Detector fibers (D), shown in cross-sectional view (FIG. 22c) and in perspective view (FIG. 22d).

FIG. 23 shows an embodiment for insertion of the probe (6) using a penetrating member (502) that is configured so that it surrounds the probe (6) and resides around it. The probe (6) may be inserted so that it resides in the middle of the penetrating member (502) in a central insertion position, as shown in FIGS. 23a-b; or on the side of the penetrating member (502) in a lateral insertion position, as shown in FIGS. 23c-d.

FIGS. 24-27 show embodiments in which the patch unit (1001) comprises two optical fibers (106, 1066) or two optical bundles (107, 1077) in which light (300) is transmitted between the two optical fibers (106, 1066), or between the two optical bundles (107, 1077). In one embodiment, one optical fiber (106) or bundle (107) acts as a Source fiber (S), transmitting light from the light-emitting source (101) to the body, and the other optical fiber (1066) or bundle (1077) acts as a Detector fiber (D), passing light from the body towards the detector (102) in the patch unit (1001). In an alternative embodiment, both fibers (106, 1066) or bundles (107, 1077) transmit light (300) in both directions—from the light-emitting source (101) to the body and from the body towards the detector (102) in the patch unit (1001).

Figure 24A:
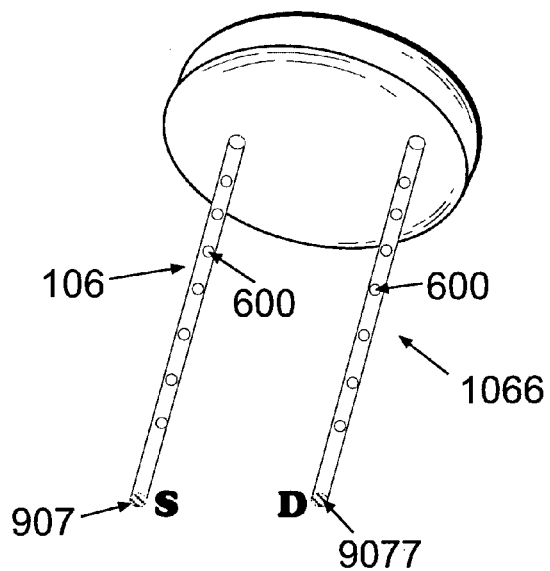
FIGS. 24a-b show the monitoring device that includes two optical fibers in which light is emitted through lateral opening in the fibers.
Figure 24B:
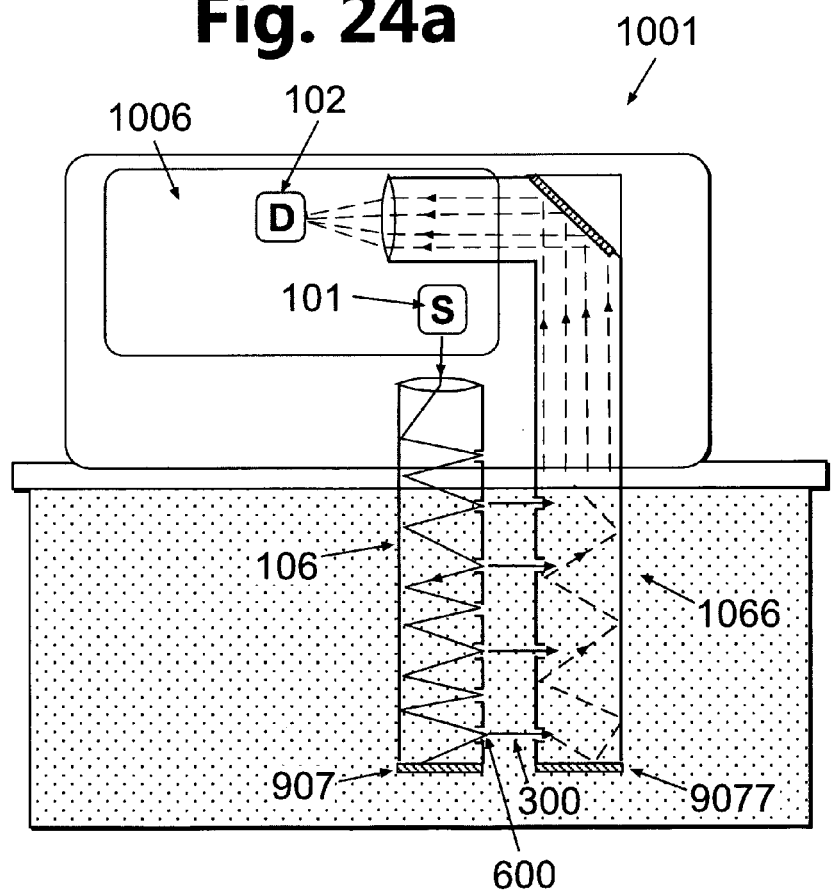

FIGS. 24a-b shows one embodiment comprising two optical fibers (106, 1066) in which light (300) is emitted through lateral openings (600) in the fibers. FIG. 24a shows the two optical fibers (106, 1066). FIG. 24b shows the monitoring device with light (300) emitting from the light-emitting source (101), passing through the Source fiber (106), and passing to the analyte-containing ISF through openings (600) in the optical fiber (106) located laterally on the fiber (106). Light (300) is transmitted to the surrounding analyte-containing ISF, and is particularly directed towards the opposing Detector fiber (1066). The light (300) enters the Detector fiber (1066) through openings located laterally on the fiber (1066). The Detector fiber (1066) directs the light (300) back towards the detector (102), within the monitoring apparatus (1006) in the patch unit (1001). In one embodiment, at the bottom of the Source optical fiber (106) and/or the Detector optical fiber (1066), there are reflecting plates (907, 9077) which reflect the light (300) back from the end of the optical fibers (106, 1066), thus enhancing the light transmitting properties of each optical fiber (106, 1066).

Figure 25A:
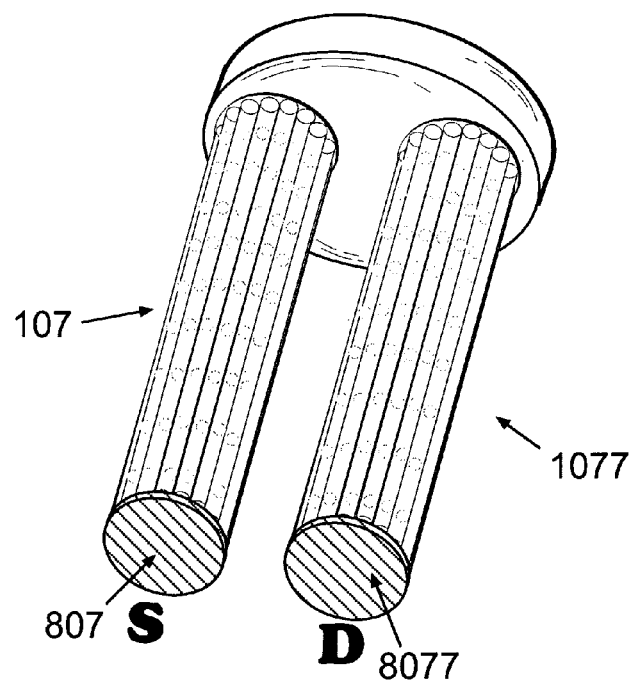
FIGS. 25a-c show the monitoring device that includes two optical fiber bundles in which light is emitted from the distal end of the bundles and directed by reflectors.
Figure 25B:
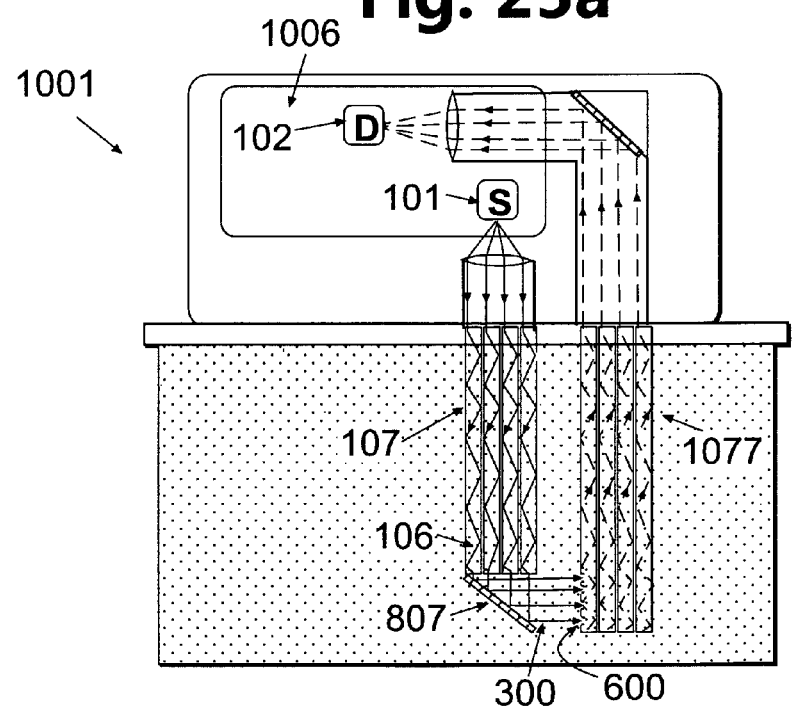
Figure 25C:
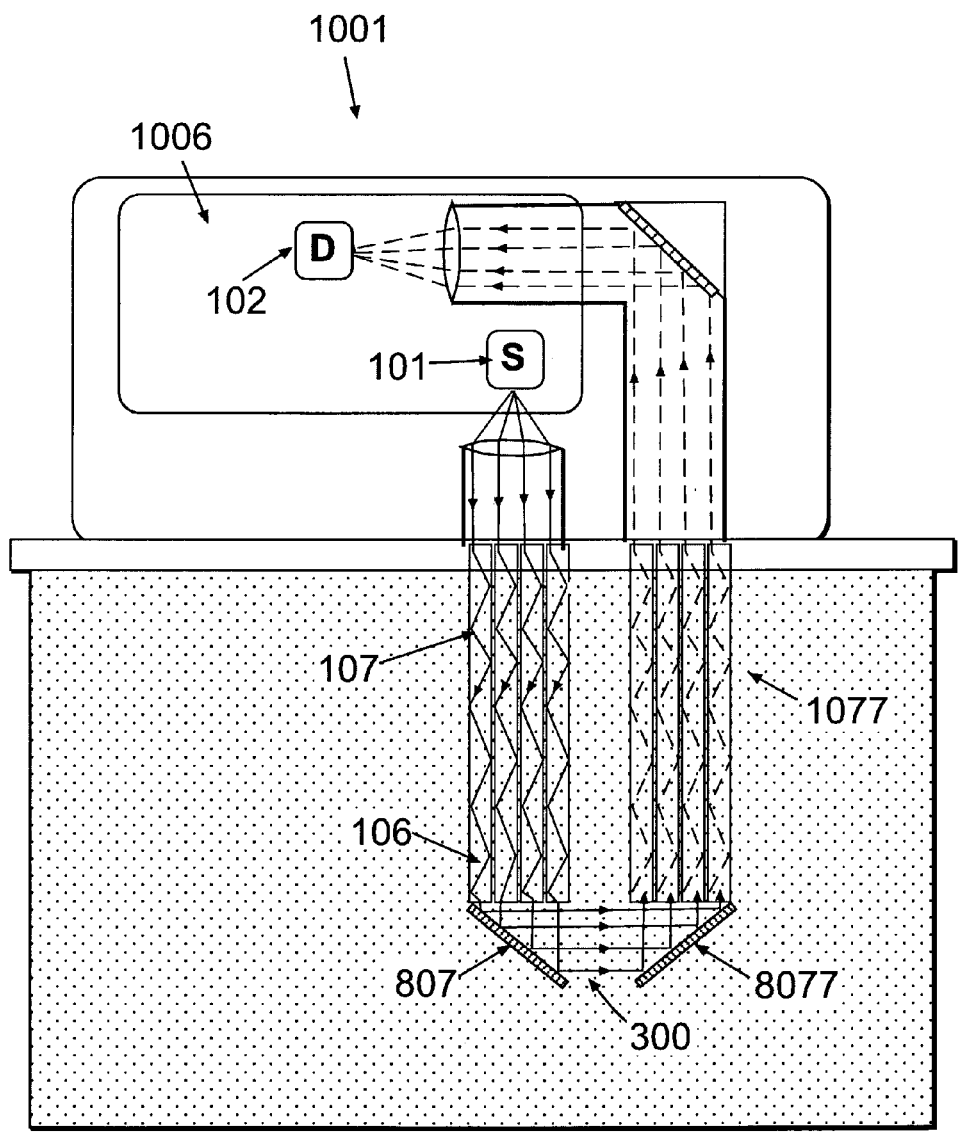

FIGS. 25a-c shows an embodiment comprising two optical fiber bundles (107, 1077) in which light (300) is emitted through the bottom of the bundles and is transmitted to the opposing bundle via reflectors (807, 8077).

FIG. 25a shows the two optical fiber bundles (107, 1077). FIG. 25b shows light (300) emitting from the light-emitting source (101), passing through the Source fiber bundle (107), and passing to a reflector (807) at the bottom of the Source fiber bundle (107). The reflector (807) transmits the light (300) through the analyte-containing ISF, towards the opposing Detector fiber bundle (1077). The light enters the Detector fiber bundle (1077) through openings (600) located laterally on the bundle (1077). The Detector bundle (1077) transmits the light (300) back towards the detector (102) in the monitoring apparatus (1006) within the patch unit (1001). FIG. 25c shows an embodiment in which the reflector (807) transmits the light (300) through the analyte-containing ISF, towards a corresponding reflector (8077) located on the bottom of the opposing Detector fiber bundle (1077), which transmits the light (300) into the Detector fiber bundle (1077). The Detector bundle (1077) transmits the light (300) back towards the detector (102) in the monitoring apparatus (1006) within the patch unit (1001).

Figure 26A:
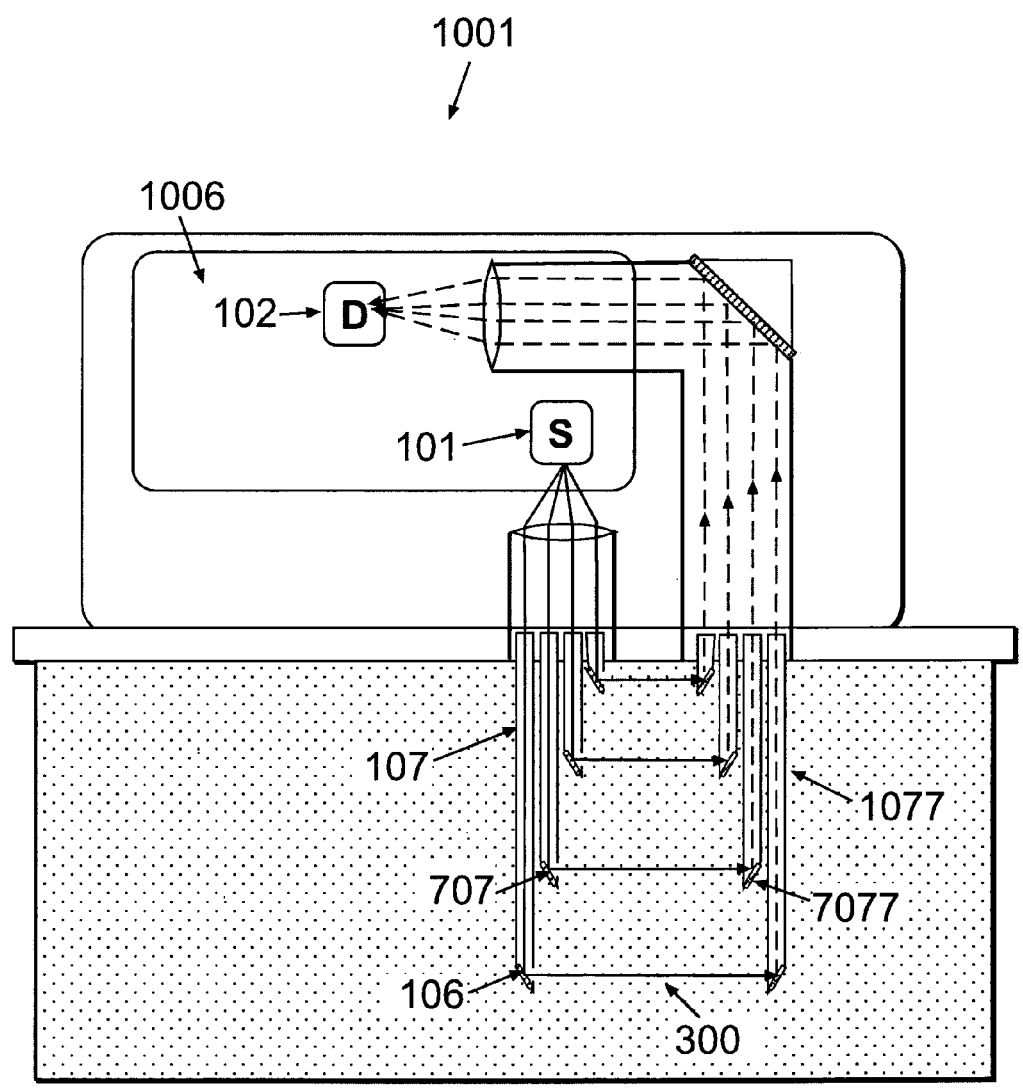
FIGS. 26a-b show the monitoring device that includes two optical fiber bundles comprising optical fibers of varying lengths, with reflectors located at the distal end of the fibers within the bundles.
Figure 26B:
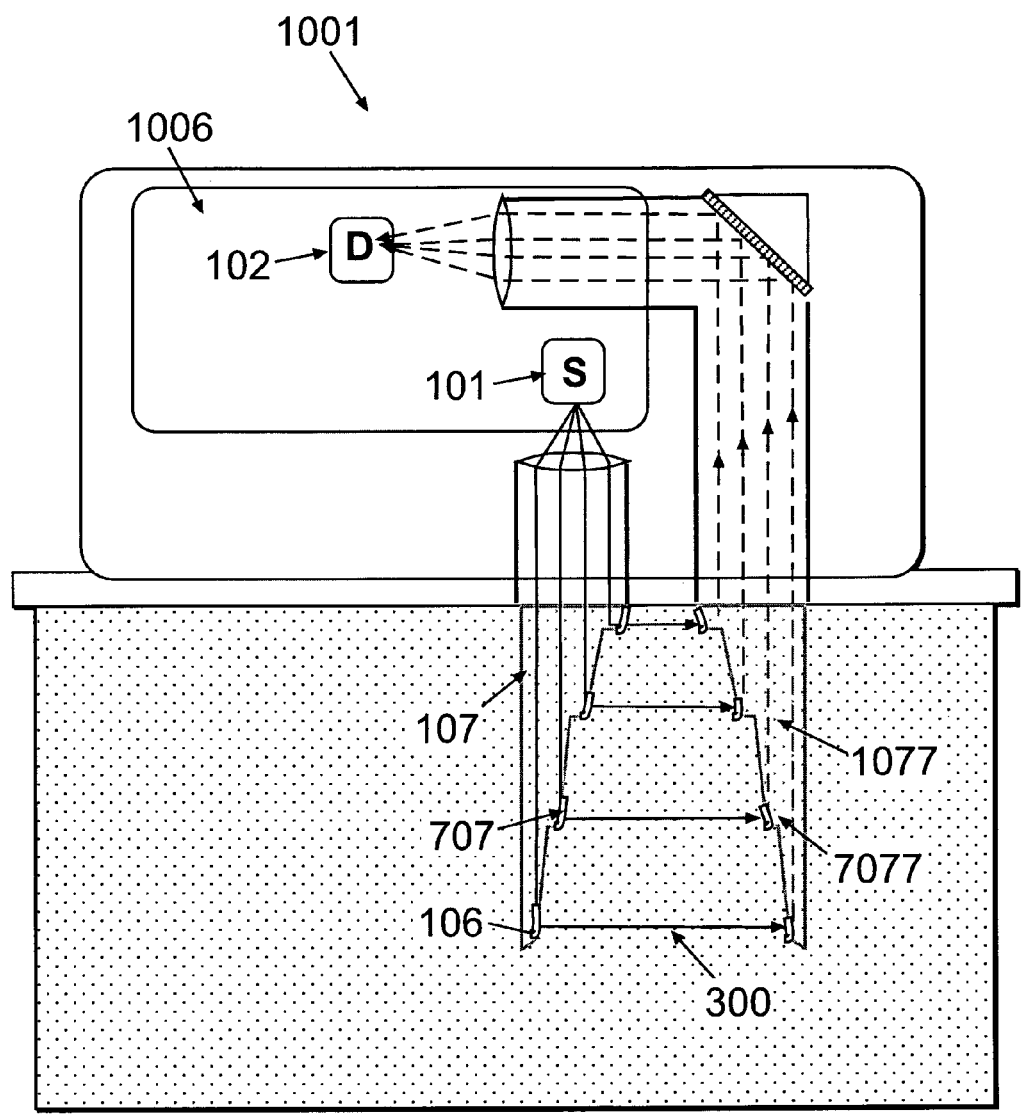

FIGS. 26a-b show embodiments comprising two optical fiber bundles (107, 1077) in which the optical fibers (106) within each bundle (107, 1077) have varying lengths. FIG. 26a shows an embodiment in which a reflector (707) is located at the end of each optical fiber (106) within each bundle (107) and transmits the light (300) towards a reflector (7077) at the end of an optical fiber (106) of similar length in an opposing bundle (1077). Light (300) emitted from the light emitting source (101) passes through each fiber (106) within the Source bundle (107). Light (300) comes out of the bottom of each fiber (106), where a reflector (707) is located, and which transmits the light (300) through the analyte-containing ISF, towards a reflector (7077) located on the bottom of an optical fiber (106) of the same length in the opposing Detector fiber bundle (1077). The opposing reflectors (7077) transmit the light (300) into the Detector fiber bundle (1077), which transmits the light (300) back towards the detector (102) in the monitoring apparatus (1006) within the patch unit (1001). FIG. 26b shows an embodiment in which each fiber bundle (107, 1077) is constructed in a jagged configuration having optical fibers of varying lengths. A reflector (707) is located at each fiber (106) and transmits the light (300) towards a reflector (7077) located at the corresponding fiber (106) on the opposing bundle (107, 1077). Light (300) emitted from the light emitting source (101) passes through the Source bundle (107), reaches the reflector (707) at each fiber (106), which transmits the light (300) through the analyte-containing ISF, towards a reflector (7077) on the opposing tooth on the Detector fiber bundle (1077). The opposing reflectors (7077) transmit the light (300) into the Detector fiber bundle (1077), which transmits the light (300) back towards the detector (102) in the monitoring apparatus (1006) of the monitoring unit (1001).

Figure 27:
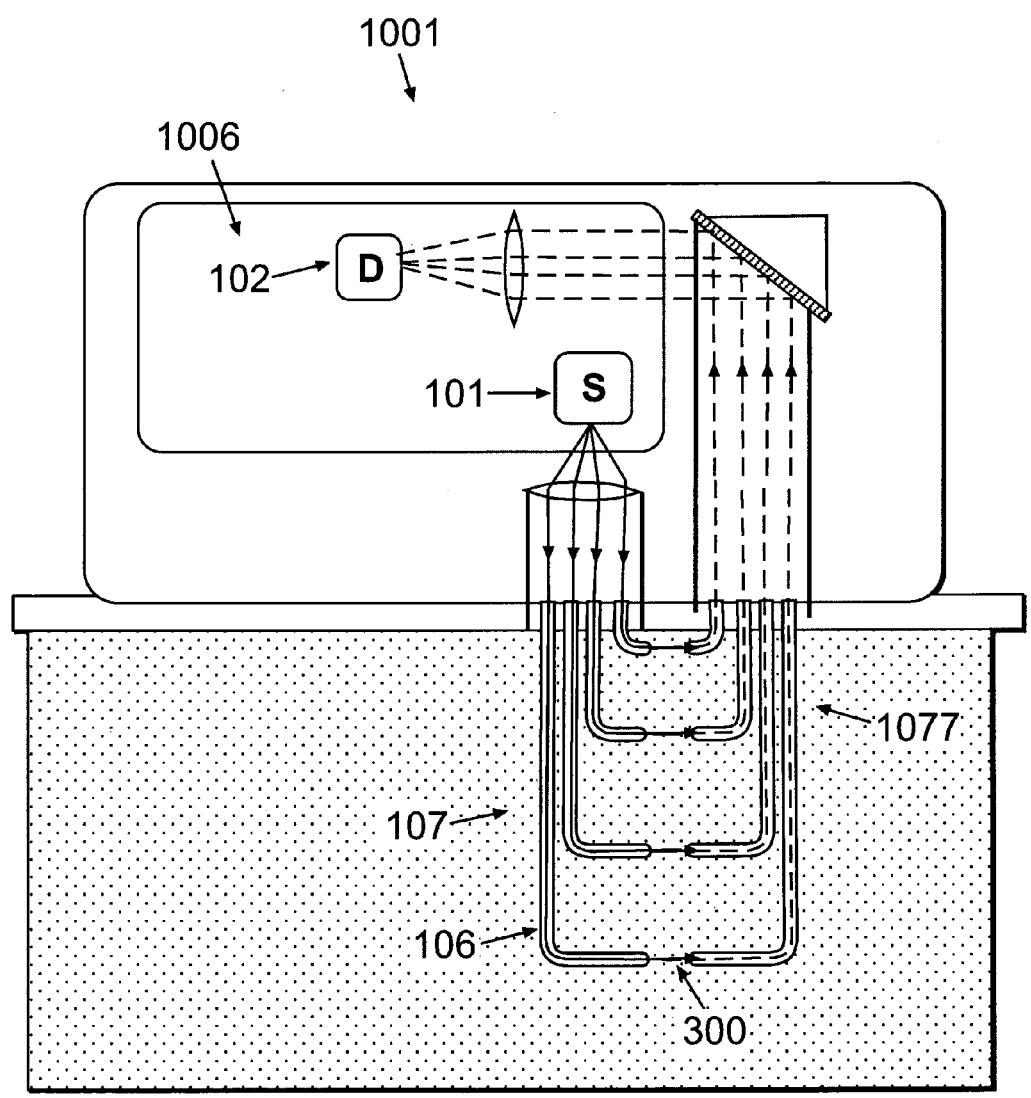
FIG. 27 shows the monitoring device that includes two optical fiber bundles comprising bent optical fibers.

FIG. 27 shows an embodiment having two optical fiber bundles (107, 1077) in which the optical fibers (106) within each bundle are bent and directed towards the opposing bundle so that light (300) is emitted through the end of the bent fibers towards the opposing bundle. Light (300) emitted from the light-emitting source (101) passes through each fiber (106) within the Source bundle (107). Each fiber (106) is bent, preferably in a 90° angle, directed towards the opposing bundle (1077). Light (300) comes out of the end of each bent fiber (106), and is transmitted through the analyte-containing ISF, towards a bent optical fiber (106) within the opposing Detector fiber bundle (1077). The bent fibers (106) within the Detector bundle (107) pass the light (300) towards the detector (102) in the monitoring apparatus (1006) within the patch unit (1001).

Figure 28A:
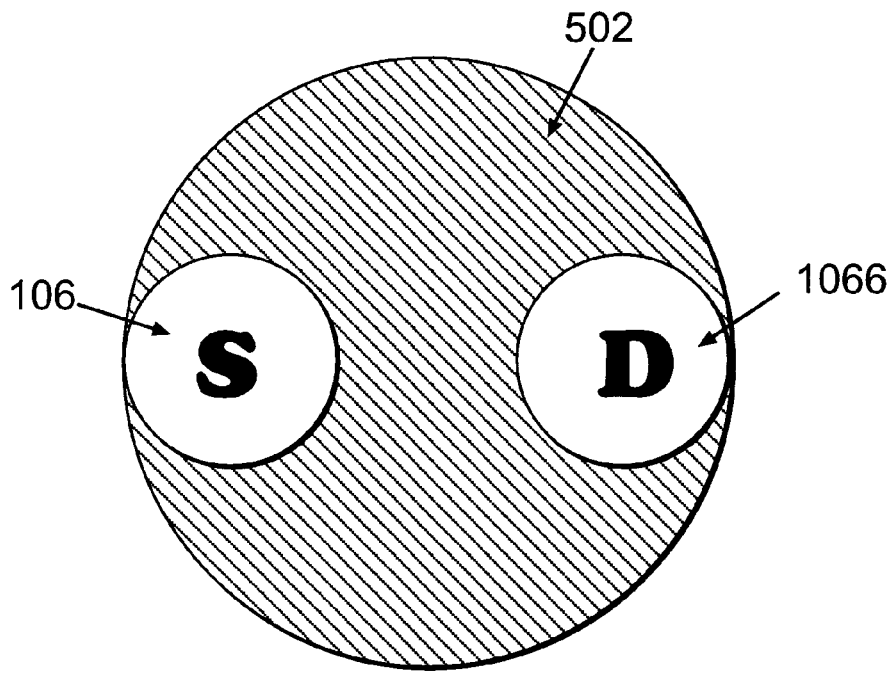
FIGS. 28a-c show means for insertion of optical fibers or bundles using a wide lumen penetrating member.
Figure 28B:
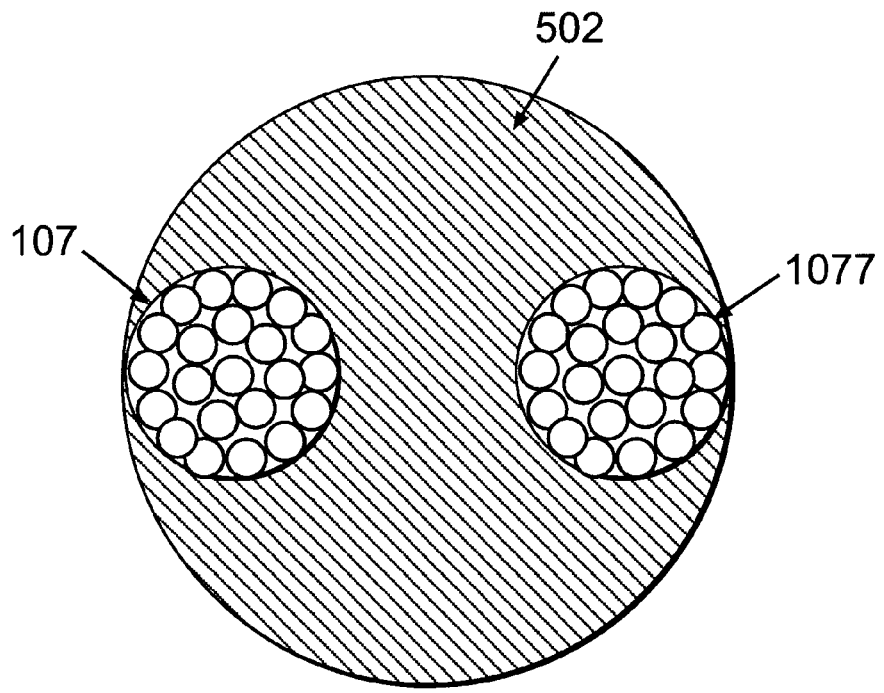
Figure 28C:
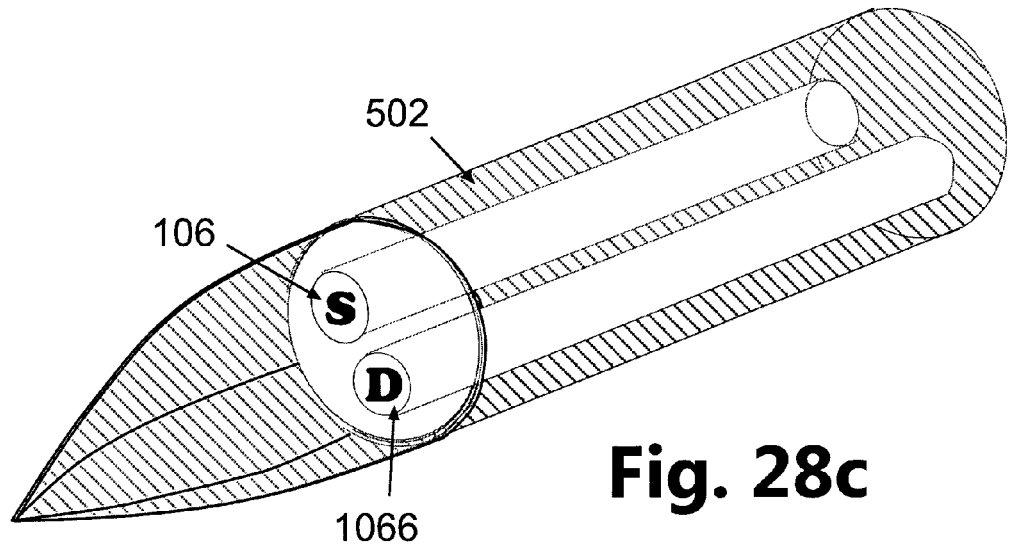

FIG. 28 shows an embodiment for insertion of the two optical fibers (106, 1066) or two optical fiber bundles (107, 1077) using a penetrating member (502) that is configured so it surrounds the two optical fibers (106, 1066) or bundles (107, 1077) and resides around them. The two optical fibers (106, 1066) or bundles (107, 1077) are inserted so that each resides on one side of the penetrating member (502). FIGS. 28a and 28b show a cross-section of the penetrating member (502) and the two fibers (106, 1066) and the two fiber bundles (107, 1077), respectively. FIG. 28c shows a perspective view of the penetrating member (502) and the two fibers (106, 1066) or bundles (107, 1077).

Figure 29A:
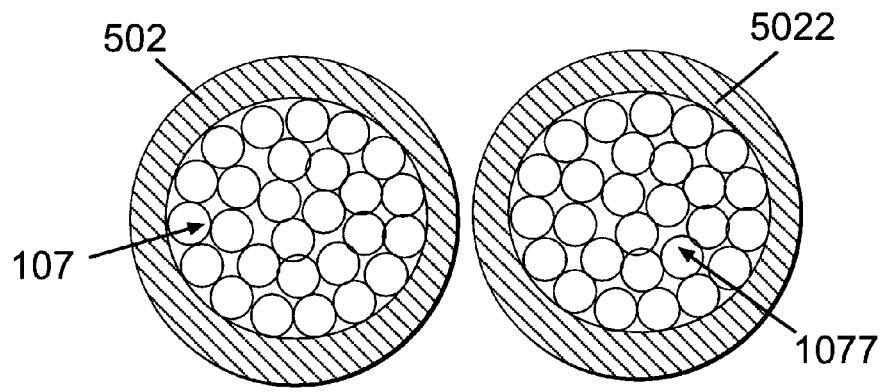
FIGS. 29a-b show means for insertion of optical fibers or bundles using two penetrating members, one for each fiber or bundle.
Figure 29B:
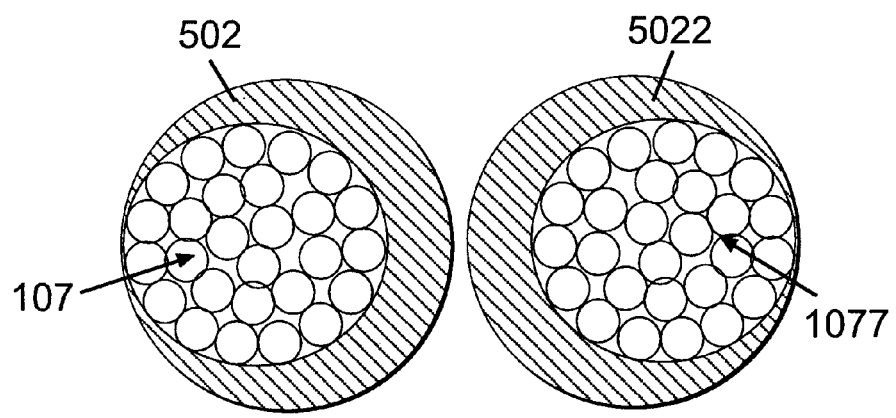

FIG. 29 shows an embodiment for insertion in which each fiber bundle (107, 1077) has its own penetrating member (502, 5022) configured to surround a fiber bundle (107, 1077). The two fiber bundles (107, 1077), and corresponding penetrating members (502, 5022) are positioned one next to the other. The two optical fiber bundles (107, 1077) may be inserted in a center insertion position, as shown in FIG. 29a, or in a lateral position, as shown in FIG. 29b.

Figure 30A:
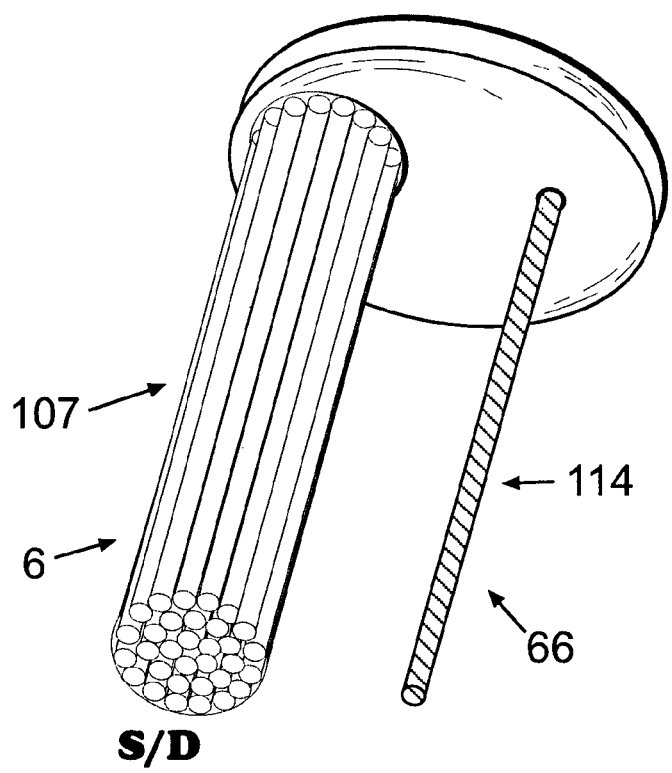
FIGS. 30a-f show a monitoring device that includes various configurations of two probes: an optical fiber or optical fiber bundle as one probe, and a reflector rod as the other probe.
Figure 30B:
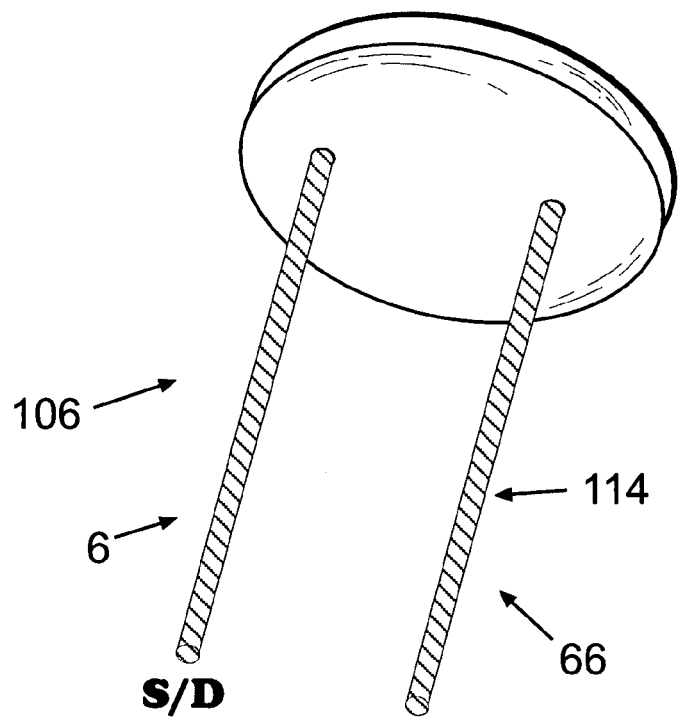
Figure 30C:
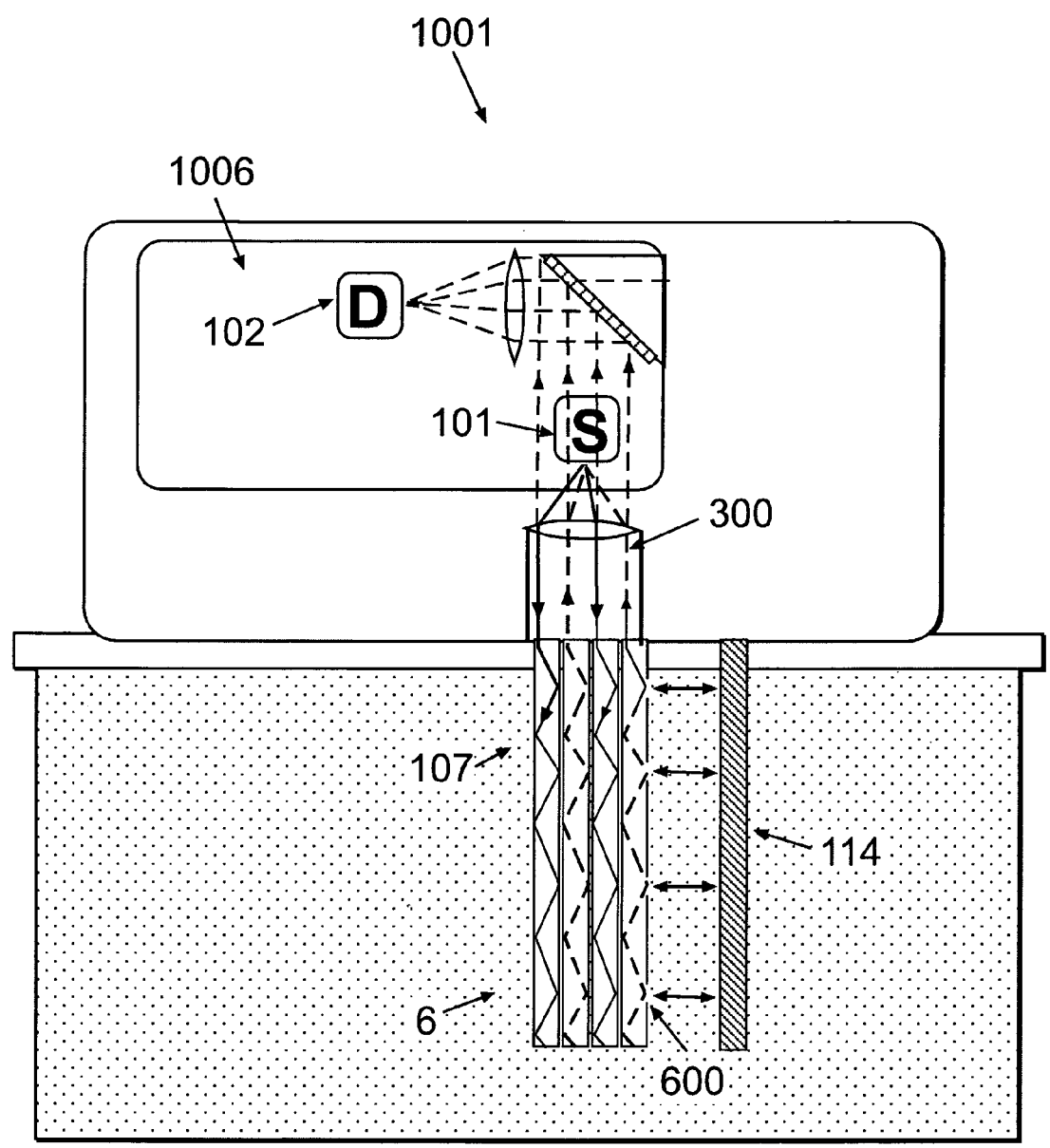
Figure 30D:
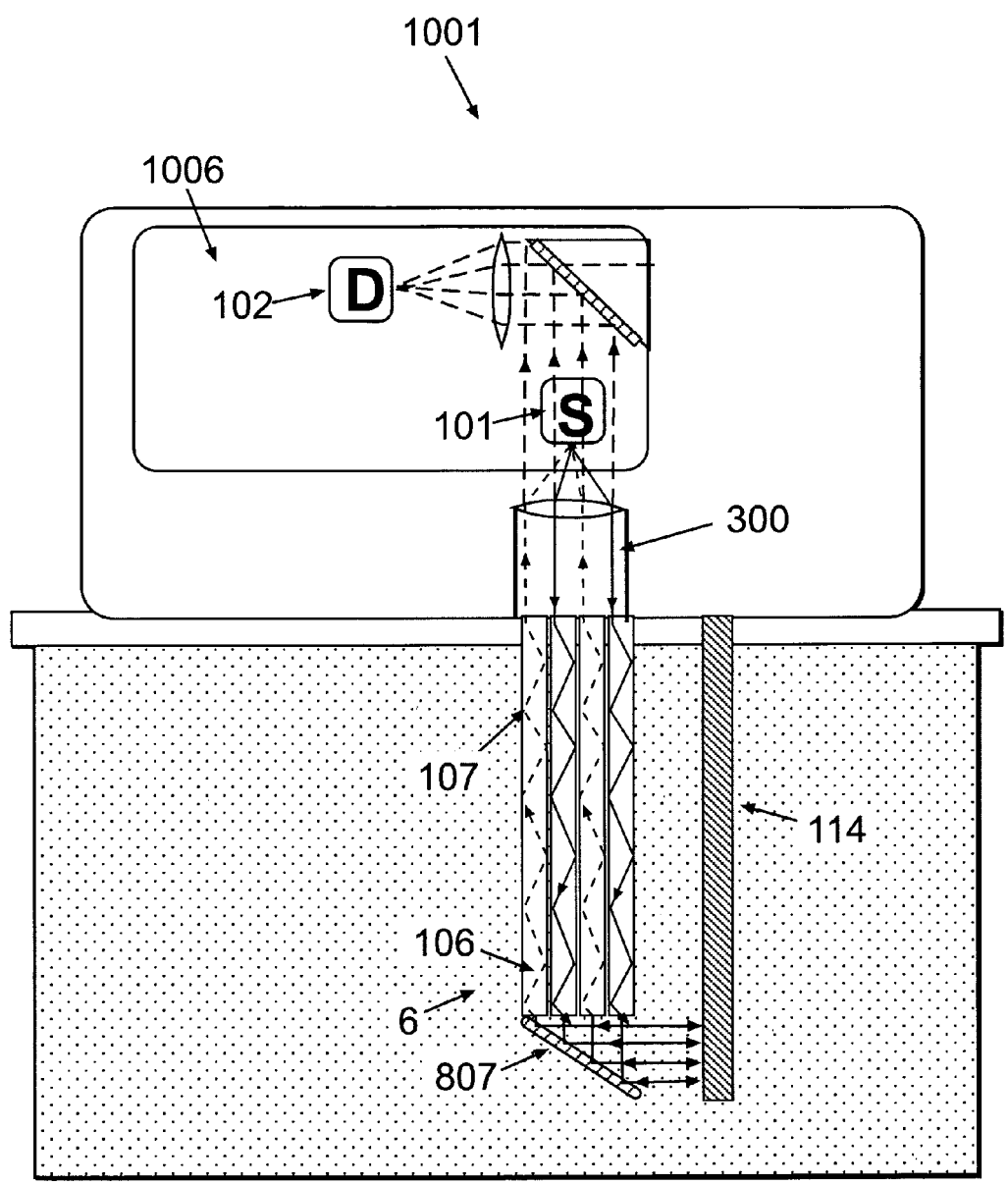
Figure 30E:
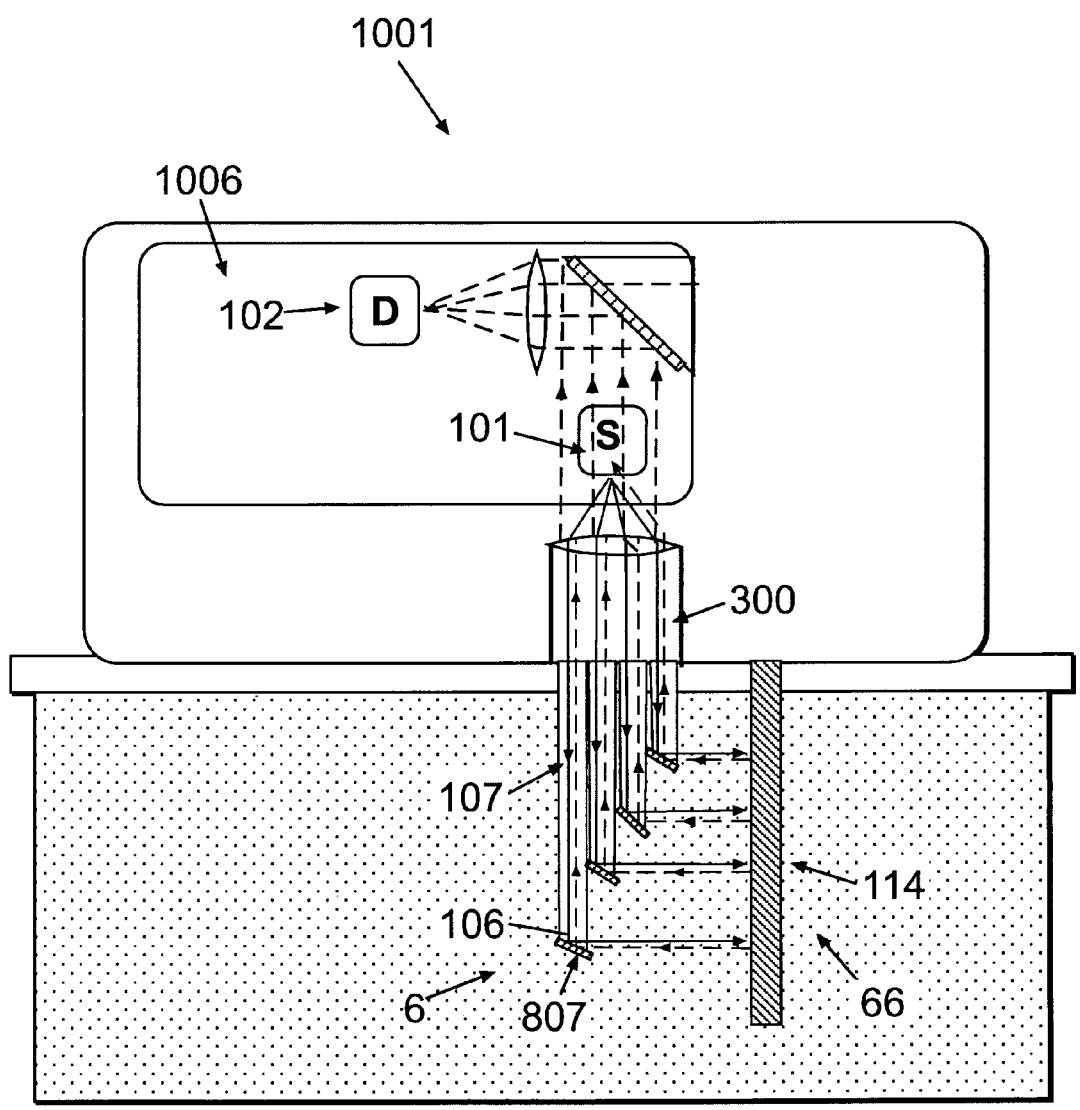
Figure 30F:
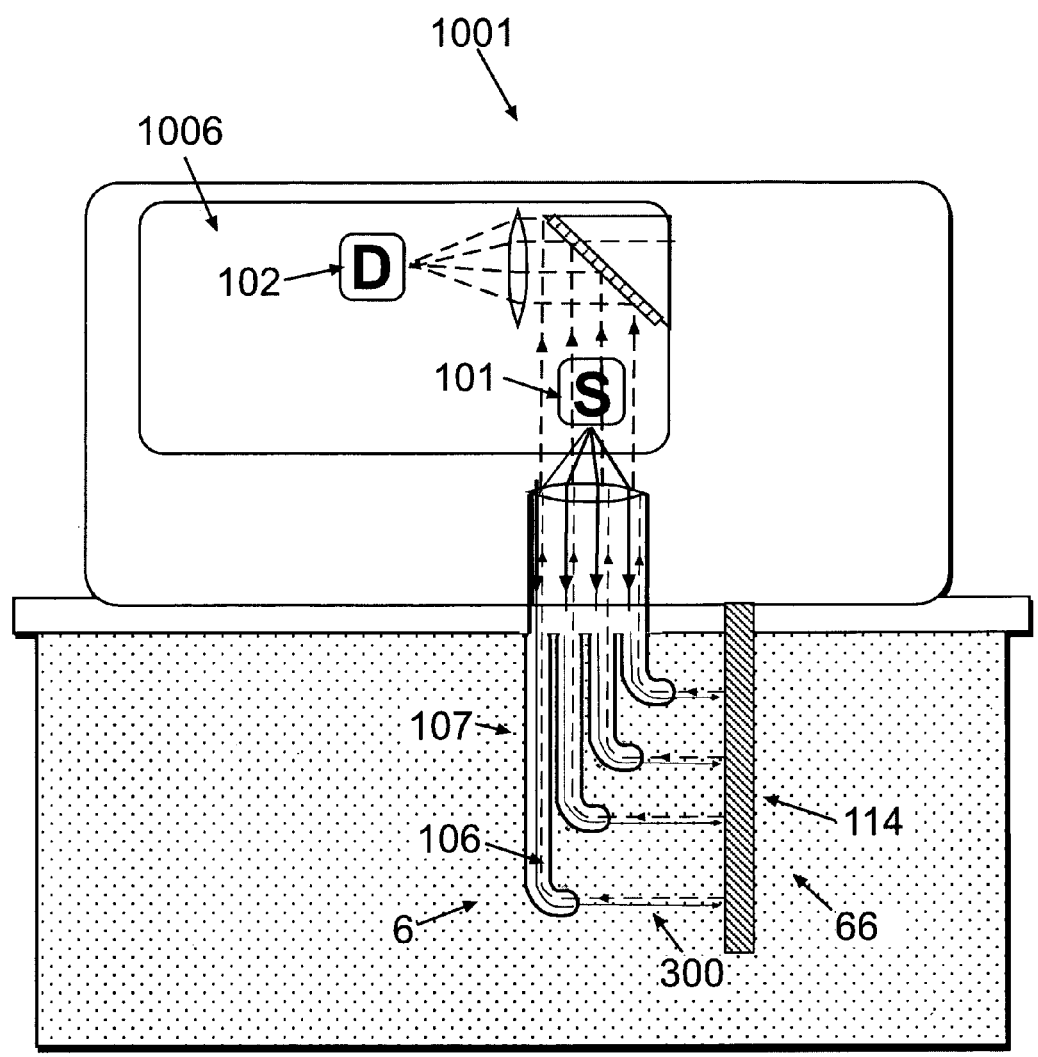

FIGS. 30a-f show embodiments in which the patch unit (1001) comprises two probes (6, 66), one probe (6) comprising an optical fiber (106) or optical fiber bundle (107), and the other probe (66) comprising a reflector rod (114). FIGS. 30a and 30b show an embodiment with a probe (6) comprising an optical fiber bundle (107) or fiber (106), respectively. The fiber (106) or bundle (107) may transmit light in both directions—from a light-emitting source to the body and from the body towards a detector. FIG. 30c shows an embodiment in which the patch unit (1001) contains a probe (6) having a bundle (107). The probe (6) may also contain one or more optical fibers (not shown). Light (300) emitted from the light-emitting source (101) passes through the bundle (107) or fiber (106), and is transmitted through the analyte-containing ISF towards the reflector rod (114). The reflector rod (114) transmits the light (300) back towards the optical fiber bundle (107) or fiber (106), which transmits the light back to the detector (102), in the monitoring apparatus (1006) in the patch unit (1001). In one embodiment, light (300) is emitted through lateral openings (600) in the bundle (107) or fiber (106), and through which the returned light enters the fiber bundle (107). FIG. 30d shows an embodiment in which the patch unit (1001) contains a probe (6) having a bundle (107). The probe (6) may also contain one or more optical fibers (not shown). In this embodiment, light (300) is emitted through the bottom of the bundle (107) or fiber (106), and is transmitted to the opposing reflector rod (114) via a reflector (807) at the bottom of the bundle (107). The light (300) from the reflector rod (114) enters the bundle (107) or fiber (106) through the reflector (807), and is transmitted to the detector (102). FIG. 30e shows an embodiment having an optical fiber bundle (107) in which the optical fibers (106) within the bundle (107) have varying lengths with reflectors (807) located at the end of each optical fiber (106). Light (300) passes through each fiber (106) within the bundle (107) and comes out of the bottom of each fiber (106), where reflectors (807) transmit the light towards the opposing reflector rod (114). The returned light (300) from the reflector rod (114) enters the bundle (107) through the bottom reflectors (807) and is transmitted to the detector (102). FIG. 30f shows an embodiment, in which the optical fibers (106) within the fiber bundle (107) are bent and directed towards the opposing reflector rod (114). Light (300) is emitted through the end of the bent fibers (106) towards the opposing reflector rod (114). The light (300) from the reflector rod (114) enters the bundle (107) through the bent fibers (106) and is transmitted to the detector (102).

Figure 31:
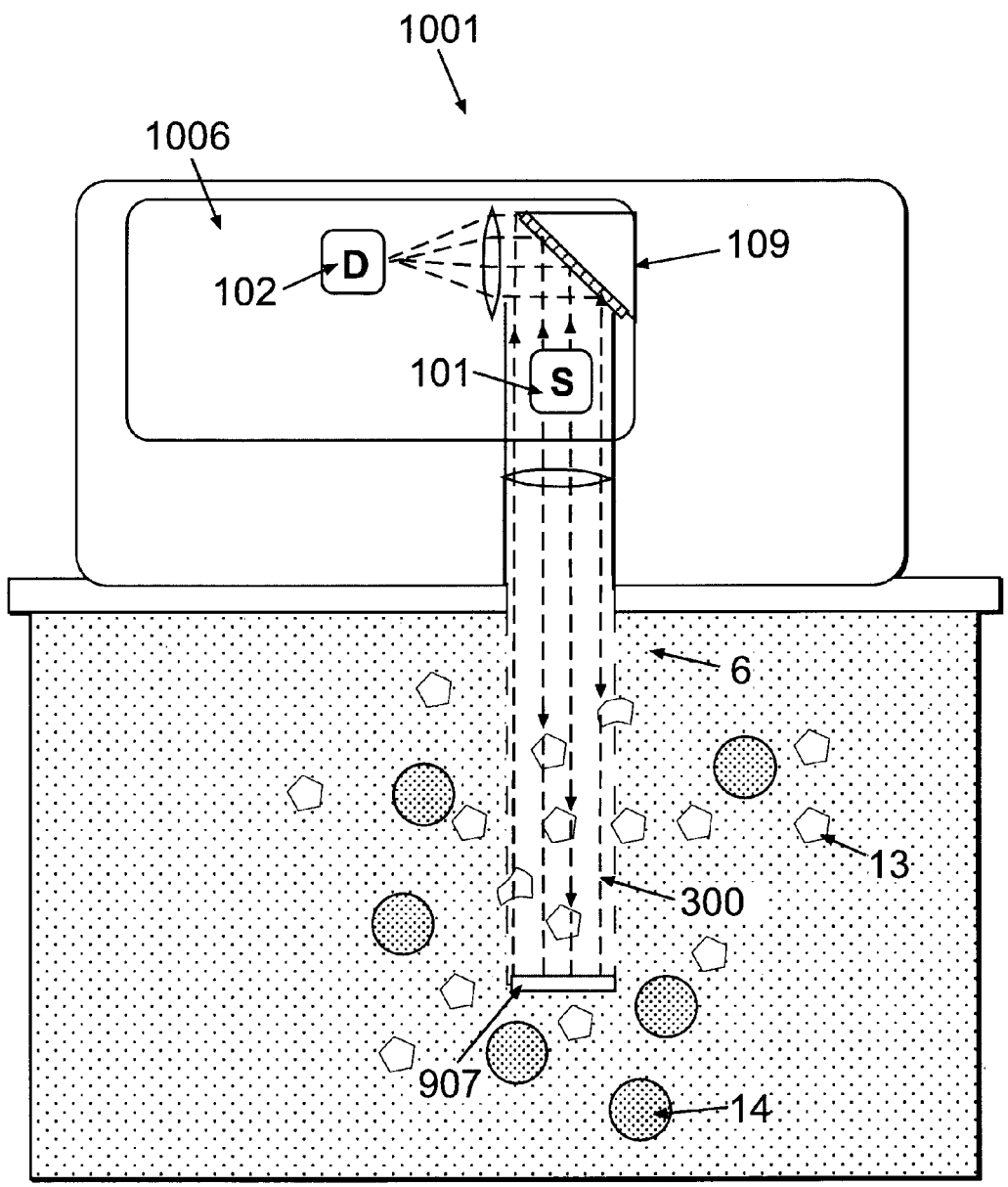
FIG. 31 shows a monitoring device that contains a permeable or semi-permeable probe.

FIG. 31 shows an embodiment in which the patch unit (1001) contains probe (6) composed of a permeable or semi-permeable membrane enabling diffusion and allowing entry of ISF with analyte molecules into the probe (6). The diffusion process, which occurs across the permeable or semi-permeable membrane, allows analyte molecules to move according to the concentration gradient, resulting in analyte-rich ISF within the probe (6). In one embodiment, the probe (6) is semi-permeable allowing substances of low molecular weight and particularly, the desired analyte (13) to pass through pores of the probe's semi-permeable membrane, while substances (14) of higher molecular weight do not pass through the pores. In another embodiment, the probe is permeable in such a manner that in addition to the diffusion of analyte molecules from the ISF into the probe, additional analytes contained in the ISF (14) also can diffuse into the probe through its membrane.

In these embodiments, light (300) is emitted from the light-emitting source (101) through the optical system (109), which transmits the light (300) to the permeable or semi-permeable probe (6). The emitted light passes through the analyte-enriched ISF within the probe (6) and hits the bottom of the probe (6), where a reflecting plate (907) is located. The reflecting plate (907) transmits the light (300) towards the optical system (109) and back to the detector (102) in the monitoring apparatus (1006) of the patch unit (1001). The walls of the probe (6) can be made of a material that does not absorb the light with wavelengths corresponding to the light emitted from the light-emitting source (101). This allows the light to pass into the probe (6).

Figure 32A:
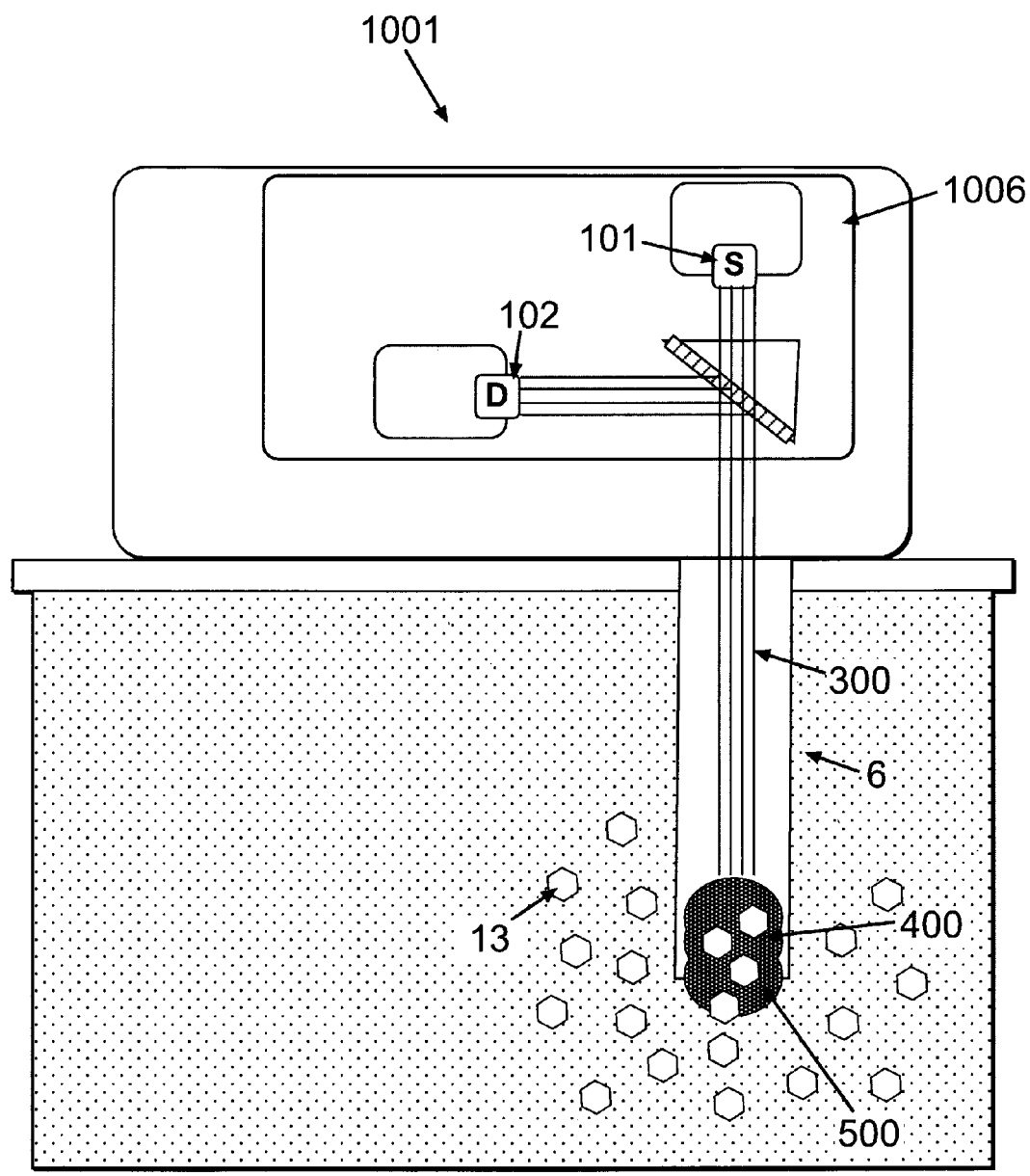
FIG. 32a-b shows a patch unit that includes a monitoring apparatus based on fluoroscopic means, with a configuration in which the fluorescent complex resides inside a hollow probe, at its distal end (FIG. 32a) and the fluorescent complex resides on the outer walls of the probe (FIG. 32b).
Figure 32B:
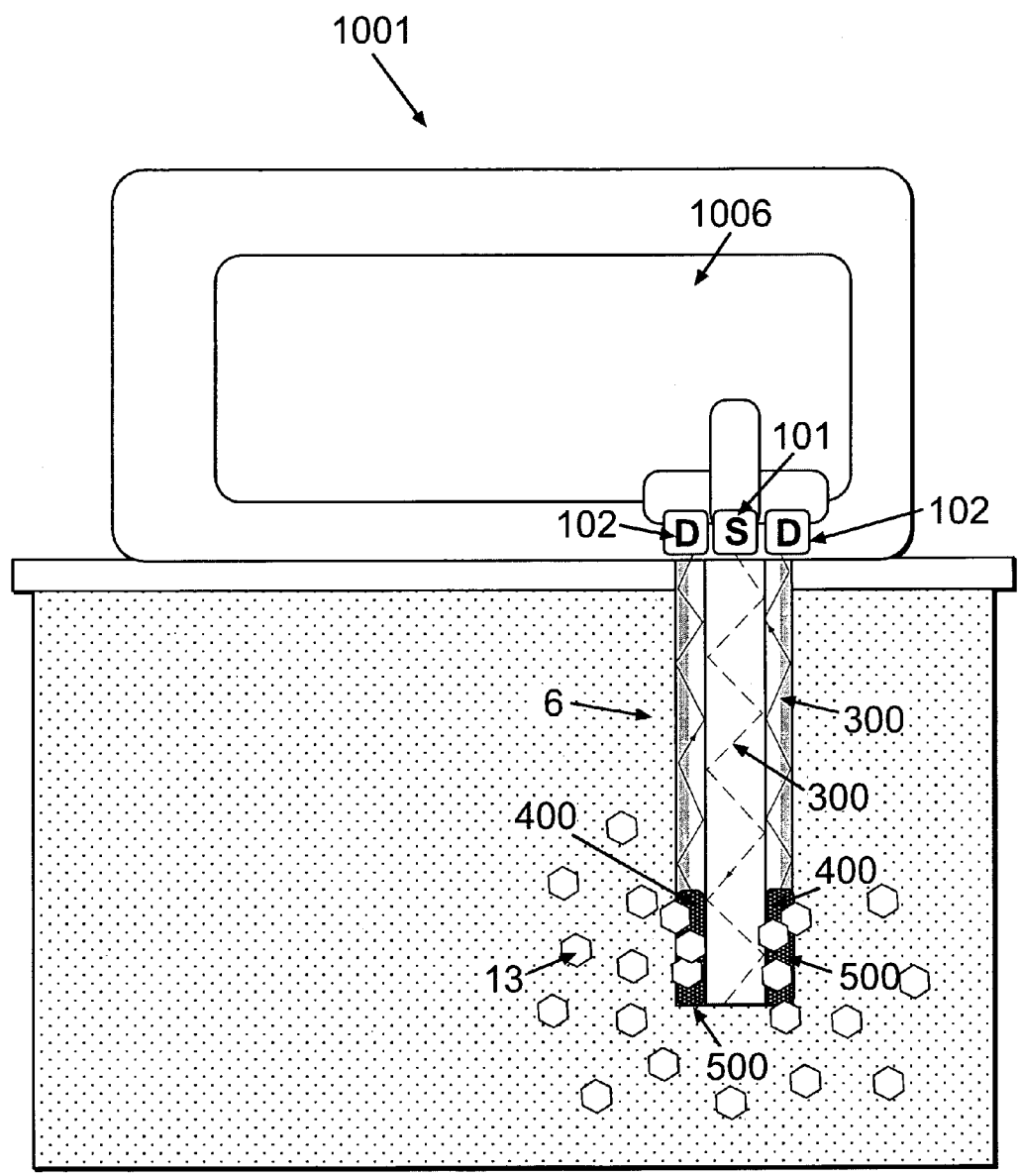

FIGS. 32a-b show embodiments in which the monitoring apparatus (1006) in the patch unit (1001) is based on fluoroscopic means. A fluorescent chemical complex is immobilized in a "thin-film hydrogel," which, in turn, is permeable to analyte molecules (13). The monitoring system has two components: a fluorescent dye (400) and a "quencher" (500), based on boronic acid, that is responsive to analyte molecules (13). In the absence of analyte molecules (13), the quencher (500) binds to the dye and prevents fluorescence, while the interaction of analyte molecules (13) with the quencher (500) leads to dissociation of the complex and an increase in fluorescence. (Diab Tech Ther, 2006, Vol. 8, No. 3:279-287; Angew Chem Int Ed 2003, 42, 5857-59; U.S. Pub. No. 2006/0083688 to Singaram et al.). The fluorescence is stimulated by light (300) emitted from the light-emitting source (101) and can be easily measured by the detector (102) because it occurs at a distinct wavelength from the light-emitting source (101). The fluorescent dye (400) and "quencher" (500) reside on the probe (6), where they come in contact with analyte-containing ISF. In one embodiment, the fluorescent dye (400) and quencher (500) reside inside the probe (6) at its bottom, where they come in contact with analyte molecules (13) in the ISF, as shown in FIG. 32a. In another embodiment, the fluorescent dye (400) and quencher (500) reside on the outer walls of the probe (6), where they come in contact with analyte molecules (13) in the ISF, as shown in FIG. 32b.

Figure 33A:
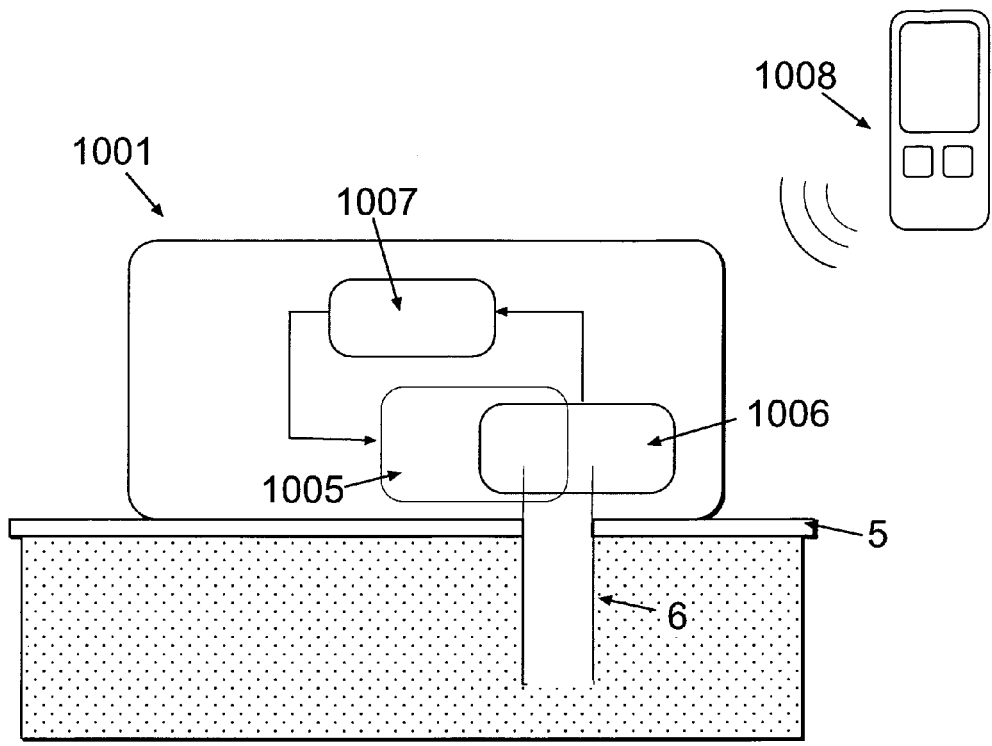
FIGS. 33a-b show a patch unit having a monitoring apparatus and a dispensing apparatus.
Figure 33B:
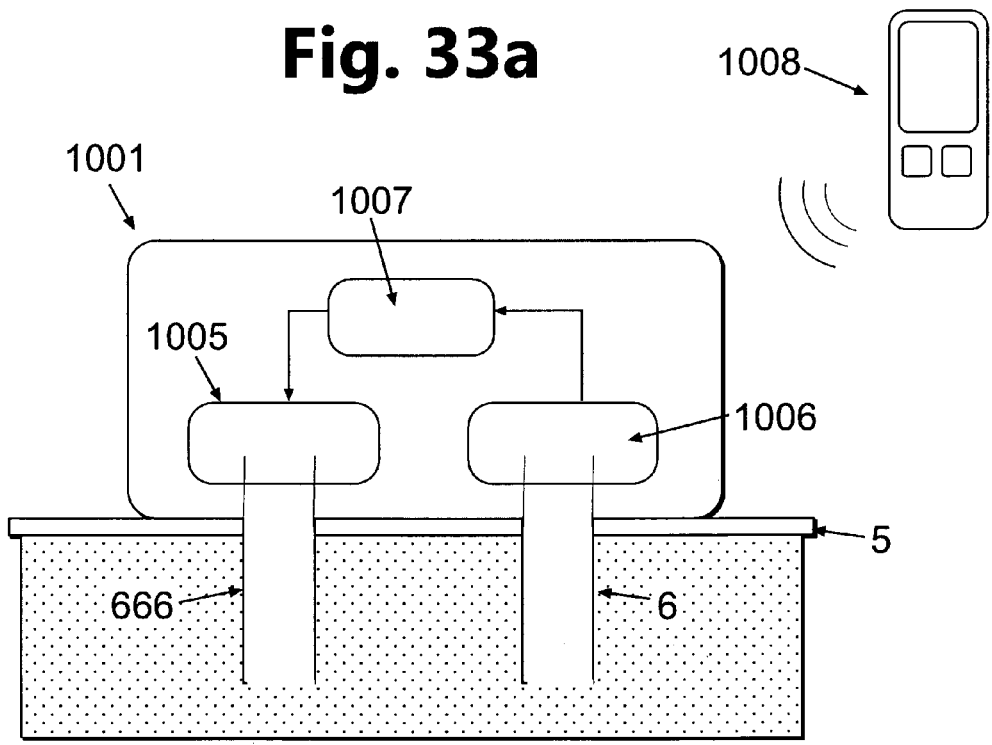

FIGS. 33a-b show embodiments in which the patch unit (1001) contains a monitoring apparatus (1006) and dispensing apparatus (1005). The monitoring apparatus (1006) monitors analyte concentration levels in the user's body and has various components, including without limitation, a light-emitting source, detector, and optical system. The dispensing apparatus (1006) delivers fluid into the body and may have features of an insulin pump, including without limitation, a reservoir, driving mechanism, and tubing. In one embodiment, the dispensing apparatus (1005) and monitoring apparatus (1006) are enclosed in a single patch unit (1001) and use a single probe (6) to perform the dispensing and monitoring operations. The monitoring and dispensing unit concomitantly monitor analyte levels and dispenses a therapeutic substance that may control analyte levels. The dispensing and monitoring apparatuses (1005, 1006) may work independently of each other. The dispensing apparatus (1005) and monitoring apparatus (1006) may work as a semi or fully closed-loop system, in which the dispensing apparatus (1005) controls the delivery of fluid to the body according to analyte concentration levels measured by the monitoring apparatus (1006).

FIG. 33a shows the patch unit (1001) with a dispensing apparatus (1005), monitoring apparatus (1006), and processor-controller (1007), a probe (6) located under the skin (5) in the subcutaneous tissue, and a remote control unit (1008). The patch unit (1001) can be adhered to the user's skin (5) by adhesives, either directly or using the cradle unit (20) (not shown). The remote control unit (1008) maintains a bidirectional or unidirectional communication channel with the patch unit (1001) allowing programming, control, data handling, display, and user input. The patch unit (1001) is connected to a single probe (6) positioned in the skin (5) and allows concomitant fluid delivery to the body and monitoring of analytes in the body. In one embodiment, the dispensing apparatus (1005) and monitoring apparatus (1006) operate independently. In another embodiment, the two apparatuses operate as a closed-loop system, in which the processor-controller (1007) receives input (e.g., analyte concentration) from the monitoring apparatus (1006) and after processing the data, authorizes the dispensing apparatus (1005) to dispense fluid accordingly. In another embodiment, the monitoring device works as a semi-closed-loop system in which the processor-controller (1007) receives input from the user through the remote control unit (1008) or any other input means known to those skilled in the art.

FIG. 33b shows an embodiment in which the monitoring apparatus (1006) uses the probe (6) and the dispensing apparatus (1005) uses a cannula (666), both inserted into the body. The monitoring apparatus (1006) uses the probe (6) for monitoring analyte concentration levels (e.g., glucose) and the dispensing apparatus (1005) uses the cannula (666) for delivering fluid (e.g., insulin). In some embodiments, the preferred pumping mechanism in the dispensing apparatus (1005) is peristaltic. In some embodiments, a pumping mechanism that contains a syringe reservoir may be used.

Figure 34A:
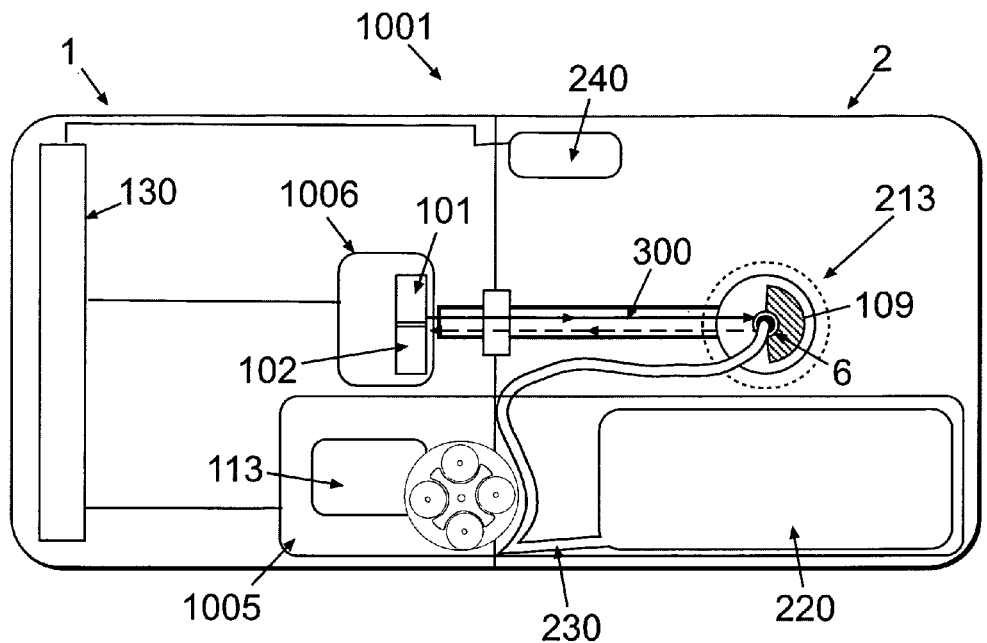
FIGS. 34a-d show in details a patch unit having a monitoring apparatus and a dispensing apparatus.
Figure 34B:
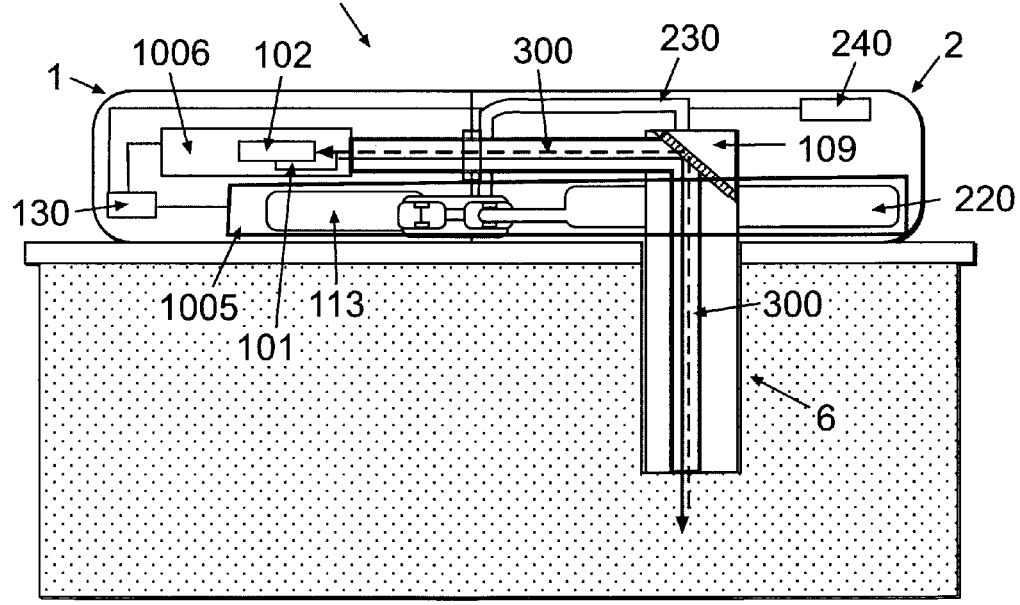
Figure 34C:
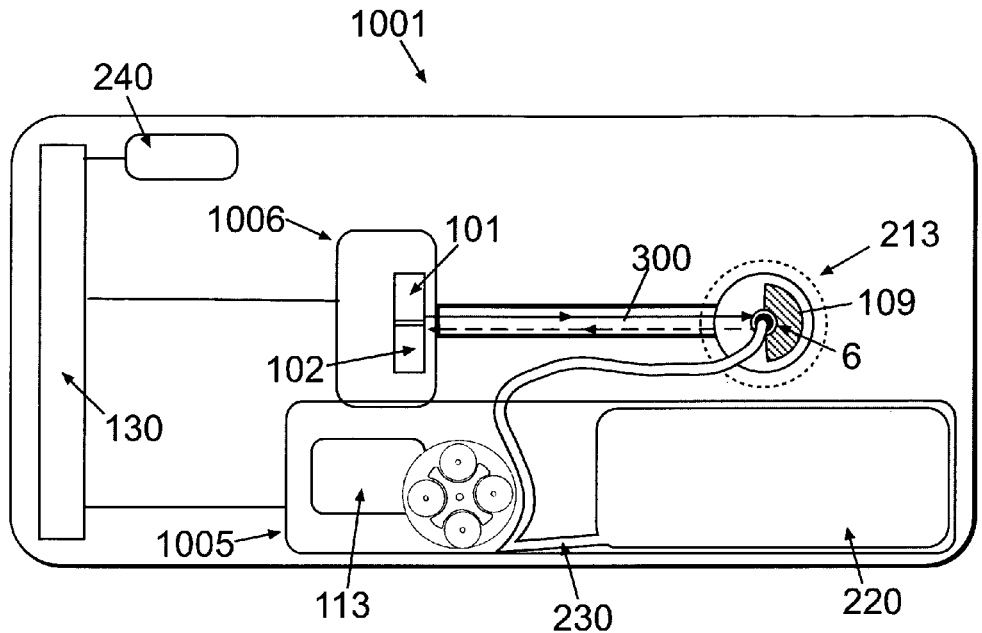
Figure 34D:
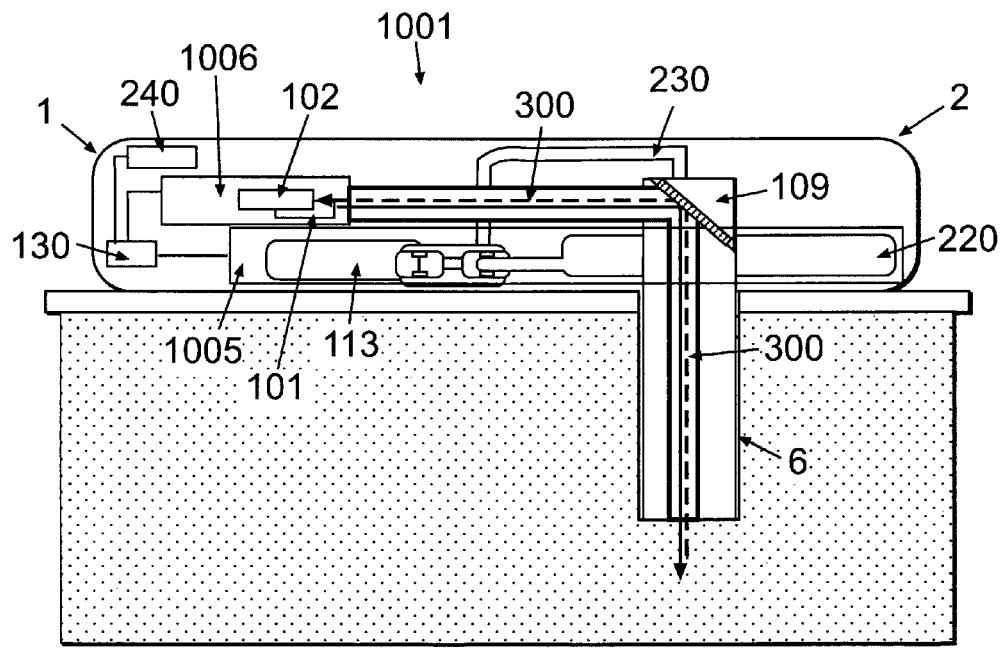

FIGS. 34a-d show an embodiment of a monitoring patch unit (1001) with its components. FIGS. 34a-b show an embodiment of a two-part patch unit (1001) having a reusable part (1) and a disposable part (2). The components of the monitoring apparatus (1006) and dispensing apparatus (1005) are located either in the reusable part (1) or the disposable part (2) of the patch unit (1001), according to their function and purpose. The dispensing apparatus (1005) may employ a peristaltic pumping mechanism. All relatively expensive, non-disposable components of the monitoring apparatus (1006) and dispensing apparatus (1005), for example, the source (101), the detector (102), rotary pump wheel (110), driving mechanism (113), and electronics (130), reside within the reusable part (1) of the patch unit (1001). Some components of the monitoring apparatus (1006) and dispensing apparatus (1005), such as parts of the optical system (109), energy supply (240), reservoir (220), delivery tube (230), and outlet port (213) may reside within the reusable part (1) or disposable part (2) of the patch unit (1001). The patch unit (1001) may be connected to a single probe (6) which is used for both dispensing and monitoring functions. Two probes (not shown) may also be used, one for dispensing fluid and another for monitoring analytes. FIG. 34a shows a top view of the patch unit (1001) with the reusable part (1) and disposable part (2). FIG. 34b shows a side view of the patch unit (1001). The passage of light (300) between the reusable part (1), the disposable part (2) and the body, is enabled via optical means within the optical system (109). FIG. 34c-d show an embodiment of a one-part patch unit (1001) having the above components of the monitoring apparatus (1006) and dispensing apparatus (1005). FIG. 34c shows a top view of the patch unit (1001) and FIG. 34d shows a side view of the patch unit (1001). A single probe (6) is used for both dispensing and monitoring functions. Alternatively, two probes may be used, one for dispensing fluid and another for monitoring analytes.

A discussion of fluid dispensing can be found in co-owned, co-pending U.S. Provisional Patent Application No. 61/123,059 titled "Systems, Devices and Methods for Fluid Delivery" filed in Apr. 9, 2008, co-owned, co-pending International Applications Nos. PCT/IL2007/000499, PCT/IL2007/000641, PCT/IL2007/000643, PCT/US2008/62928, PCT/IL2008/000915, PCT/IL2008/001057, PCT/IL2008/001058, and U.S. patent application Ser. Nos. 11/397,115, 12/082,295, and 12/116,546, the disclosures of which are incorporated herein by reference in their entireties. All references patents, patent applications, articles and any other published and non-published references referred to above are herein incorporated by reference in their entirety.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, presently unclaimed inventions are also contemplated. The inventors reserve the right to pursue such inventions in later claims.

What is claimed is:

1. A device for monitoring one or more body analytes within the body of a patient, the device comprising:
   at least one source configured to be positioned external to the body for emitting electromagnetic radiation;
   at least one detector configured to be positioned external to the body for receiving electromagnetic radiation;

a plurality of subcutaneously insertable probes comprising a first probe and a second probe, each having a proximal portion configured to be positioned external to the body after insertion of the probe, and a distal portion configured for placement within a subcutaneous tissue of the patient upon insertion of the probe;

wherein the first probe is configured to:
transmit electromagnetic radiation from the at least one source to the subcutaneous tissue and toward the second probe to enable the electromagnetic radiation to interact with the one or more analytes being monitored, and
transmit the electromagnetic radiation that has interacted with the one or more body analytes from the subcutaneous tissue to the at least one detector.

2. The device as in claim 1, further comprising a processor configured for determining the one or more body analytes concentrations levels based on a signal generated by the detector.

3. The device as in claim 1, further comprising an optical element for enabling the transmission of electromagnetic radiation, the optical element selected from a group consisting of: windows, mirrors, reflectors, lenses, optical fibers, optical bundles, and combinations thereof.

4. The device as in claim 3, wherein the optical element is a part of the first subcutaneously insertable probe.

5. The device as in claim 1, wherein the first probe includes at least one lateral electromagnetic radiation opening for electromagnetic radiation transmission between the at least one subcutaneously insertable probe and the subcutaneous tissue.

6. The device as in claim 1, wherein the second subcutaneously insertable probe comprises a reflector rod.

7. The device as in claim 1, wherein the at least one of the subcutaneously insertable probes includes a plurality of optical fibers of varying lengths.

8. The device as in claim 1, wherein the at least one of the subcutaneously insertable probes includes at least one bent optical fiber.

9. The device as in claim 1 further comprising:
a reusable part including the at least one source and the at least one detector; and
a disposable part being in mechanical contact with the proximal portion of the subcutaneously insertable probes, wherein upon connection of the reusable part and disposable part, optical communication is established therebetween.

10. The device as in claim 9, wherein optical communication is established via at least one optical element selected from a group consisting of: windows, mirrors, reflectors, lenses, optical fibers and optical bundles.

11. The device as in claim 1, further comprising a cradle, wherein the cradle includes:
an adhesive layer for adhering the cradle to the skin of the patient;
at least one opening providing a passageway for the subcutaneously insertable probes; and
one or more connectors for connecting at least one of the device and the at least one subcutaneously insertable probes to the cradle.

12. The device as in claim 1, further comprising a remote control unit for providing programming, data acquisition and displaying of information associated with the programming and/or operation of the device.

13. The device as in claim 1, further comprising a display and/or at least one operating switch.

14. The device as in claim 1, further comprising at least one housing having a pump for delivering a therapeutic fluid to the body of the patient.

15. The device as in claim 14, wherein the therapeutic fluid is delivered to the body of the patient via at least one of the subcutaneously insertable probes.

16. The device as in claim 14, wherein the second probe is configured to deliver the therapeutic fluid.

17. The device as in claim 14, wherein the pump delivers the therapeutic fluid in response to a detected concentration level of the one or more body analytes.

18. The device as in claim 1, wherein the first probe comprises at least one optical fiber having an outer layer, the outer layer of the optical fiber defining one or more openings along a longitudinal length of the fiber to allow the electromagnetic radiation to be transmitted therethrough.

19. A method for monitoring one or more body analytes concentration levels, the method comprising:
providing at least one source for emitting electromagnetic radiation, at least one detector for detecting electromagnetic radiation, and a plurality of subcutaneously insertable probes comprising a first probe and a second probe, each having a proximal portion and a distal portion, wherein the at least one source, the at least one detector, and the proximal portions of the probes are configured to be positioned external to the body, and the distal portions are configured for placement within subcutaneous tissue of a patient;
emitting electromagnetic radiation from the at least one source, via the first probe, into the subcutaneous tissue and toward the second probe to allow the electromagnetic radiation to interact with the one or more body analytes being monitored;
collecting the electromagnetic radiation that has interacted with the one or more body analytes;
transmitting the collected electromagnetic radiation, via the first probe to the at least one detector; and
determining a concentration level of the one or more body analytes based on the collected electromagnetic radiation.

20. The method as in claim 19, wherein the monitoring of the one or more body analytes is accomplished using at least one of the following optical detection methods: visible, near infrared (NIR) reflectance, mid-infrared (MIR), infrared (IR), spectroscopy, light scattering, Raman scattering, fluoroscopy, polarimetry, photoacoustic spectroscopy, and combinations thereof.

21. The method as in claim 19, further comprising delivering a therapeutic fluid to the body of the patient based on the determined concentration level of the one or more body analytes.

22. The method as in claim 19, wherein the monitoring of the one or more body analytes is continuous.

23. The method as in claim 19, wherein determining the concentration level of the one or more body analytes comprises spectral analysis of the collected electromagnetic radiation.

* * * * *